(12) United States Patent
West et al.

(10) Patent No.: US 12,404,493 B2
(45) Date of Patent: Sep. 2, 2025

(54) METHODS FOR THE RE-DERIVATION OF DIVERSE PLURIPOTENT STEM CELL-DERIVED BROWN FAT CELLS

(71) Applicant: AgeX Therapeutics, Inc., Alameda, CA (US)

(72) Inventors: Michael D. West, Mill Valley, CA (US); Hal Sternberg, Berkeley, CA (US)

(73) Assignee: AgeX Therapeutics, Inc., Alameda, CA (US)

( * ) Notice: Subject to any disclaimer, the term of this patent is extended or adjusted under 35 U.S.C. 154(b) by 0 days.

(21) Appl. No.: 15/994,302

(22) Filed: May 31, 2018

(65) Prior Publication Data

US 2020/0157505 A1    May 21, 2020

Related U.S. Application Data

(63) Continuation of application No. PCT/US2016/065366, filed on Dec. 7, 2016.

(60) Provisional application No. 62/264,311, filed on Dec. 7, 2015.

(51) Int. Cl.
C12N 5/077 (2010.01)
C12N 5/0735 (2010.01)
C12Q 1/6881 (2018.01)

(52) U.S. Cl.
CPC ......... *C12N 5/0653* (2013.01); *C12N 5/0606* (2013.01); *C12Q 1/6881* (2013.01); *C12N 2501/385* (2013.01); *C12N 2506/02* (2013.01); *C12Q 2600/158* (2013.01)

(58) Field of Classification Search
CPC ............... C12N 5/0653; C12N 5/0606; C12N 2501/385; C12N 2506/02; C12Q 2600/158
See application file for complete search history.

(56) References Cited

U.S. PATENT DOCUMENTS

| | | |
|---|---|---|
| 5,030,015 A | 7/1991 | Baker et al. |
| 5,489,508 A | 2/1996 | West et al. |
| 5,639,613 A | 6/1997 | Shay et al. |
| 5,686,306 A | 11/1997 | West et al. |
| 5,843,780 A | 12/1998 | Thomson |
| 5,922,601 A | 7/1999 | Baetscher et al. |
| 6,200,806 B1 | 3/2001 | Thomson |
| 6,248,934 B1 | 6/2001 | Tessier-Lavigne et al. |
| 6,280,718 B1 | 8/2001 | Kaufman et al. |
| 6,465,493 B1 | 10/2002 | Burgess et al. |
| 6,602,711 B1 | 8/2003 | Thomson et al. |
| 6,667,176 B1 | 12/2003 | Funk et al. |
| 6,685,911 B1 | 2/2004 | Zitvogel et al. |
| 6,887,706 B2 | 5/2005 | Zhang et al. |
| 7,176,023 B2 | 2/2007 | Kaufman et al. |
| 7,217,569 B2 | 5/2007 | Thomson |
| 7,253,334 B2 | 8/2007 | Collas et al. |
| 7,417,041 B2 | 8/2008 | Blumberg et al. |
| 7,582,479 B2 | 9/2009 | Thomson |
| 7,585,622 B1 | 9/2009 | Cech et al. |
| 7,625,573 B2 | 12/2009 | Zitvogel et al. |
| 7,736,895 B2 | 6/2010 | Collas et al. |
| 7,928,069 B2 | 4/2011 | Prestwich et al. |
| 7,951,591 B2 | 5/2011 | Robl et al. |
| 7,981,871 B2 | 7/2011 | Prestwich et al. |
| 8,021,847 B2 | 9/2011 | Pietrzkowski |
| 8,058,065 B2 | 11/2011 | Yamanaka et al. |
| 8,090,542 B2 | 1/2012 | Khvorova et al. |
| 8,236,774 B2 | 8/2012 | Cech et al. |
| 8,247,384 B2 | 8/2012 | Green et al. |
| 8,324,184 B2 | 12/2012 | Prestwich et al. |
| 8,476,017 B2 | 7/2013 | Pietrzkowski |
| 8,685,386 B2 | 4/2014 | West et al. |
| 9,175,263 B2 | 11/2015 | Larocca et al. |
| 10,227,561 B2 | 3/2019 | Larocca et al. |
| 10,240,127 B2 | 3/2019 | Larocca et al. |
| 10,688,136 B2 | 6/2020 | Quarta et al. |
| 10,716,591 B2 | 7/2020 | Anderson et al. |
| 2001/0039316 A1 | 11/2001 | Campbell et al. |
| 2002/0001842 A1 | 1/2002 | Chapman |
| 2002/0051762 A1 | 5/2002 | Rafii et al. |
| 2002/0069484 A1 | 6/2002 | Creel |
| 2002/0142397 A1 | 10/2002 | Collas et al. |
| 2003/0046722 A1 | 3/2003 | Collas et al. |
| 2003/0129745 A1 | 7/2003 | Robl et al. |
| 2003/0149277 A1 | 8/2003 | Gaster et al. |

(Continued)

FOREIGN PATENT DOCUMENTS

| | | |
|---|---|---|
| CN | 102105789 A | 6/2011 |
| CN | 104114693 A | 10/2014 |

(Continued)

OTHER PUBLICATIONS

Ohno et al. PPAR agonists induce a white-to-brown fat conversion through stabilization of PRDM16 protein. Cell Metab. Mar. 7, 2012; 15(3): 395-404 (Year: 2012).*
Nedergaard et al. PPAR in the control of brown adipocyte differentiation. Biochimica et Biophysica Acta 1740 (2005) 293-304. (Year: 2005).*
Abad et al., Reprogramming in vivo produces teratomas and iPS cells with totipotency features. Nature. 2013;502(7471):340-345.
Bodnar et al., Extension of life-span by introduction of telomerase into normal human cells. Science. 1998;279(5349):349-352.
Chuang et al., The fission yeast homologue of Orc4p binds to replication origin DNA via multiple AT-hooks. Proc Natl Acad Sci U S A. 1999;96(6):2656-2661.
Crisan et al., A perivascular origin for mesenchymal stem cells in multiple human organs. Cell Stem Cell. Sep. 11, 2008;3(3):301-13.

(Continued)

*Primary Examiner* — Taeyoon Kim
(74) *Attorney, Agent, or Firm* — McCarter & English, LLP; Jonathan M. Sparks

(57) ABSTRACT

Aspects of the present invention include methods and compositions related to the production and use of pluripotent stem cell-derived clonal embryonic progenitor cell types useful in the generation of cellular components of brown adipocyte tissue for research and therapy relating to applications in obesity, diabetes, and cardiovascular disease.

12 Claims, 9 Drawing Sheets

Specification includes a Sequence Listing.

(56) References Cited

U.S. PATENT DOCUMENTS

| | | |
|---|---|---|
| 2003/0161817 A1 | 8/2003 | Young et al. |
| 2003/0166633 A1 | 9/2003 | Gaster et al. |
| 2003/0180268 A1 | 9/2003 | Atala |
| 2003/0232430 A1 | 12/2003 | Cibelli et al. |
| 2004/0001807 A1 | 1/2004 | Edelberg et al. |
| 2004/0039198 A1 | 2/2004 | Bender et al. |
| 2004/0063745 A1 | 4/2004 | Gellibert et al. |
| 2004/0152738 A1 | 8/2004 | Gaster et al. |
| 2004/0199935 A1 | 10/2004 | Chapman |
| 2004/0219563 A1 | 11/2004 | West et al. |
| 2004/0220230 A1 | 11/2004 | Gaster et al. |
| 2004/0228847 A1 | 11/2004 | Goldschmidt-Clermont et al. |
| 2004/0247567 A1 | 12/2004 | Gurtner |
| 2004/0266842 A1 | 12/2004 | Gaster et al. |
| 2005/0014258 A1 | 1/2005 | Collas et al. |
| 2005/0014938 A1 | 1/2005 | Gaster et al. |
| 2005/0165011 A1 | 7/2005 | Gellibert et al. |
| 2005/0250727 A1 | 11/2005 | Tasken et al. |
| 2006/0003446 A1 | 1/2006 | Keller et al. |
| 2006/0171930 A1 | 8/2006 | Seyda et al. |
| 2006/0212952 A1 | 9/2006 | Collas et al. |
| 2007/0072901 A1 | 3/2007 | Washio |
| 2007/0116684 A1 | 5/2007 | Atala et al. |
| 2007/0154428 A1 | 7/2007 | Sato et al. |
| 2007/0154474 A1 | 7/2007 | Soppet et al. |
| 2007/0155013 A1 | 7/2007 | Akaike et al. |
| 2008/0070303 A1 | 3/2008 | West et al. |
| 2008/0233610 A1 | 9/2008 | Thomson |
| 2009/0047263 A1 | 2/2009 | Yamanaka |
| 2009/0104159 A1 | 4/2009 | Prosper et al. |
| 2009/0148423 A1 | 6/2009 | Sumitran-Holgersson |
| 2009/0220450 A1 | 9/2009 | Green et al. |
| 2009/0269314 A1 | 10/2009 | Keller et al. |
| 2010/0003757 A1 | 1/2010 | Mack |
| 2010/0055678 A1 | 3/2010 | Jaatinen et al. |
| 2010/0111914 A1 | 5/2010 | Zhang et al. |
| 2010/0158872 A1 | 6/2010 | Keller et al. |
| 2010/0166713 A1 | 7/2010 | Dalton et al. |
| 2010/0167404 A1 | 7/2010 | West et al. |
| 2010/0183620 A1 | 7/2010 | Bhawe et al. |
| 2010/0184033 A1 | 7/2010 | West et al. |
| 2010/0203021 A1 | 8/2010 | Goumans et al. |
| 2010/0255580 A1 | 10/2010 | Rezania |
| 2010/0267135 A1 | 10/2010 | Sakurada et al. |
| 2010/0330063 A1 | 12/2010 | Weinstein |
| 2011/0038791 A1 | 2/2011 | Ford et al. |
| 2011/0064701 A1 | 3/2011 | Young et al. |
| 2011/0104133 A1* | 5/2011 | Tseng .................. C12N 5/0667 424/93.21 |
| 2011/0143441 A1 | 6/2011 | West et al. |
| 2011/0218143 A1 | 9/2011 | Kaushal et al. |
| 2011/0223669 A1 | 9/2011 | Yamanaka et al. |
| 2011/0312881 A1 | 12/2011 | Silverman et al. |
| 2012/0060232 A1 | 3/2012 | Stan |
| 2012/0093885 A1 | 4/2012 | Sahoo et al. |
| 2012/0148546 A1 | 6/2012 | Dar-Oaknin et al. |
| 2012/0171171 A1 | 7/2012 | West et al. |
| 2012/0295347 A1 | 11/2012 | Kessler |
| 2012/0301443 A1 | 11/2012 | Raffi et al. |
| 2013/0015622 A1 | 1/2013 | Hata |
| 2013/0115609 A1 | 5/2013 | Ho |
| 2013/0115673 A1 | 5/2013 | West et al. |
| 2013/0196865 A1 | 8/2013 | Hochedlinger et al. |
| 2013/0202564 A1 | 8/2013 | Han et al. |
| 2013/0236961 A1 | 9/2013 | Amit et al. |
| 2014/0010801 A1 | 1/2014 | Niedernhofer et al. |
| 2014/0178988 A1 | 6/2014 | West et al. |
| 2014/0349396 A1 | 11/2014 | West et al. |
| 2015/0004144 A1* | 1/2015 | Cowan .................. A61K 35/35 424/93.7 |
| 2015/0017718 A1 | 1/2015 | Nakatsuji et al. |
| 2015/0079110 A1 | 3/2015 | Burns et al. |
| 2015/0232808 A1 | 8/2015 | West et al. |
| 2015/0275177 A1 | 10/2015 | West et al. |
| 2015/0368609 A1 | 12/2015 | Yang et al. |
| 2016/0002597 A1 | 1/2016 | Sinden et al. |
| 2016/0108368 A1 | 4/2016 | Larocca et al. |
| 2016/0186170 A1 | 6/2016 | West et al. |
| 2016/0193252 A1 | 7/2016 | Hicks et al. |
| 2016/0369237 A1 | 12/2016 | West et al. |
| 2017/0108503 A1 | 4/2017 | Klass et al. |
| 2017/0146529 A1 | 5/2017 | Nagrath et al. |
| 2017/0239320 A1 | 8/2017 | Conboy et al. |
| 2018/0170982 A1 | 6/2018 | West et al. |
| 2018/0273906 A1 | 9/2018 | Ashraf |
| 2018/0280443 A1 | 10/2018 | Glicksman et al. |
| 2019/0151372 A1 | 5/2019 | Larocca et al. |
| 2019/0175691 A1 | 6/2019 | West et al. |
| 2019/0218511 A1 | 7/2019 | Larocca et al. |
| 2019/0241873 A1 | 8/2019 | Larocca et al. |
| 2022/0088137 A1 | 3/2022 | West et al. |
| 2022/0088138 A1 | 3/2022 | West et al. |
| 2022/0090078 A1 | 3/2022 | West et al. |
| 2022/0098554 A1 | 3/2022 | Yang et al. |
| 2022/0112492 A1 | 4/2022 | West et al. |
| 2022/0160833 A1 | 5/2022 | West et al. |
| 2022/0401494 A1 | 12/2022 | Larocca et al. |
| 2022/0403341 A1 | 12/2022 | Larocca et al. |
| 2023/0093399 A1 | 3/2023 | West et al. |

FOREIGN PATENT DOCUMENTS

| | | |
|---|---|---|
| CN | 104350146 A | 2/2015 |
| CN | 105435244 A | 3/2016 |
| EP | 1001806 A1 | 5/2000 |
| EP | 1523990 A1 | 4/2005 |
| EP | 1860180 A1 | 11/2007 |
| EP | 2254586 A1 | 12/2010 |
| EP | 2496711 A2 | 9/2012 |
| EP | 3387112 A1 | 10/2018 |
| EP | 3463391 A1 | 4/2019 |
| JP | 2013-151437 A | 8/2013 |
| JP | 2016-518393 A | 6/2016 |
| JP | 2019-517538 A | 6/2019 |
| WO | WO-1998/30679 A1 | 7/1998 |
| WO | WO-1999/003499 A1 | 1/1999 |
| WO | WO-1999/20741 A1 | 4/1999 |
| WO | WO-2001/00650 A1 | 1/2001 |
| WO | WO-2001/30978 A1 | 5/2001 |
| WO | WO-2001/51616 A2 | 7/2001 |
| WO | WO-2003/046141 A2 | 6/2003 |
| WO | WO-2003/074654 A2 | 9/2003 |
| WO | WO-2003/076603 A2 | 9/2003 |
| WO | WO-2005/068610 A1 | 7/2005 |
| WO | WO-2005/121369 A2 | 12/2005 |
| WO | 2006/054262 A2 | 5/2006 |
| WO | WO-2006/130504 A2 | 12/2006 |
| WO | WO-2007/019398 A1 | 2/2007 |
| WO | WO-2007/047894 A2 | 4/2007 |
| WO | 2007/062198 A1 | 5/2007 |
| WO | WO-2007/058671 A1 | 5/2007 |
| WO | WO-2008/089448 A2 | 7/2008 |
| WO | WO-2008/148938 A1 | 12/2008 |
| WO | WO-2009/052211 A1 | 4/2009 |
| WO | WO-2009/105044 A1 | 8/2009 |
| WO | WO-2010/021993 A1 | 2/2010 |
| WO | WO-2011/053257 A2 | 5/2011 |
| WO | WO-2011/150105 A2 | 12/2011 |
| WO | WO-2012/020308 A2 | 2/2012 |
| WO | 2012/065065 A1 | 5/2012 |
| WO | WO-2012/125471 A1 | 9/2012 |
| WO | 2012/147470 A1 | 11/2012 |
| WO | WO-2013/003595 A1 | 1/2013 |
| WO | WO-2013/014691 A1 | 1/2013 |
| WO | WO-2013/036969 A1 | 3/2013 |
| WO | 2013/082268 A1 | 6/2013 |
| WO | 2013/084000 A2 | 6/2013 |
| WO | WO-2013/150303 A1 | 10/2013 |
| WO | WO-2013/172793 A1 | 11/2013 |
| WO | WO-2014/013258 A1 | 1/2014 |
| WO | WO-2014/022852 A1 | 2/2014 |
| WO | WO-2014/028493 A2 | 2/2014 |
| WO | WO-2014/091373 A1 | 6/2014 |
| WO | WO-2014/125276 A1 | 8/2014 |

(56) References Cited

FOREIGN PATENT DOCUMENTS

| WO | WO-2014/125277 A1 | 8/2014 |
|---|---|---|
| WO | WO-2014/197421 A1 | 12/2014 |
| WO | WO-2015/052526 A1 | 4/2015 |
| WO | WO-2015/052527 A1 | 4/2015 |
| WO | 2017/100313 A1 | 6/2017 |
| WO | 2017/214342 A1 | 12/2017 |
| WO | 2019/178296 A1 | 9/2019 |
| WO | 2019/209892 A1 | 10/2019 |
| WO | 2020/069373 A1 | 4/2020 |

OTHER PUBLICATIONS

Cruz et al., Extracellular Vesicles: Decoding a New Language for Cellular Communication in Early Embryonic Development. Front Cell Dev Biol. Aug. 28, 2018;6:94.
French et al., What is a Conservative Substitution? J Mol Evol. 1983;19:171-175.
Greenwood-Goodwin et al., A novel lineage restricted, pericyte-like cell line isolated from human embryonic stem cells. Sci Rep. Apr. 25, 2016;6:24403, 10 pages.
Horvath, DNA methylation age of human tissues and cell types. Genome Biol. 2013;14(10):R115, 20 pages.
Kaczkowski et al., Transcriptome Analysis of Recurrently Deregulated Genes across Multiple Cancers Identifies New Pan-Cancer Biomarkers. Cancer Res. 2016;76(2):216-226.
Kashyap et al., Regulation of stem cell pluripotency and differentiation involves a mutual regulatory circuit of the Nanog, OCT4, and SOX2 pluripotency transcription factors with polycomb repressive complexes and stem cell microRNAs. Stem Cells Dev. Sep. 2009;18(7):1093-108.
Kim et al., Specific association of human telomerase activity with immortal cells and cancer. Science. 1994;266(5193):2011-2015.
Lanza et al., Extension of cell life-span and telomere length in animals cloned from senescent somatic cells. Science. 2000;288(5466):665-669.
Lu et al., Reversal of ageing-and injury-induced vision loss by Tet-dependent epigenetic reprogramming. bioRxiv, retrieved nline at: https://www.biorxiv.org/content/10.1101/710210v1.full.pdf. 51 pages, Jul. 31, 2019.
Marion et al., Common Telomere Changes during In Vivo Reprogramming and Early Stages of Tumorigenesis. Stem Cell Reports. 2017;8(2):460-475.
Ocampo et al., In Vivo Amelioration of Age-Associated Hallmarks by Partial Reprogramming. Cell. 2016; 167(7):1719-1733.e12.
Olova et al., Partial reprogramming induces a steady decline in epigenetic age before loss of somatic identity. Aging Cell. 2019;18(1):e12877, 7 pages.
Roth et al., Telomerase levels control the lifespan of human T lymphocytes. Blood. 2003;102(3):849-857.
Shyh-Chang et al., Lin28 enhances tissue repair by reprogramming cellular metabolism. Cell. 2013;155(4):778-792.
Vaziri et al., Spontaneous reversal of the developmental aging of normal human cells following transcriptional reprogramming. Regen Med. 2010;5(3):345-363.
West et al., Use of deep neural network ensembles to identify embryonic-fetal transition markers: repression of COX7A1 in embryonic and cancer cells. Oncotarget. Dec. 28, 2017;9(8):7796-7811.
Yuan et al., Exosomes Derived From Pericytes Improve Microcirculation and Protect Blood-Spinal Cord Barrier After Spinal Cord Injury in Mice. Front Neurosci. 2019;13:319, 14 pages.
Ahfeldt et al., Programming human pluripotent stem cells into white and brown adipocytes. Nat Cell Biol. Jan. 15, 2012;14(2):209-19.
Amieux et al., Cyclic nucleotides converge on brown adipose tissue differentiation. Sci Signal. Jan. 12, 2010;3(104):pe2. 3 pages.
Ancey et al., Secretion of IL-6, IL-11 and LIF by human cardiomyocytes in primary culture. Cytokine. May 21, 2002;18(4):199-205.
Armulik et al., Pericytes regulate the blood-brain barrier. Nature. Nov. 25, 2010;468(7323):557-61.
Armulik et al., Pericytes: developmental, physiological, and pathological perspectives, problems, and promises. Dev Cell. Aug. 16, 2011;21(2):193-215.
Bai et al., BMP4 regulates vascular progenitor development in human embryonic stem cells through a Smad-dependent pathway. J Cell Biochem. Feb. 1, 2010;109(2):363-74.
Beranger et al., In vitro brown and "brite"/"beige" adipogenesis: human cellular models and molecular aspects. Biochim Biophys Acta. May 2013;1831(5):905-14.
Bergers et al., The role of pericytes in blood-vessel formation and maintenance. Neuro Oncol. Oct. 2005;7(4):452-64.
Bian et al., Extracellular vesicles derived from human bone marrow mesenchymal stem cells promote angiogenesis in a rat myocardial infarction model. J Mol Med (Berl). Apr. 2014;92(4):387-97.
Bignone et al., Identification of human embryonic progenitor cell targeting peptides using phage display. PLoS One. 2013;8(3):e58200. 12 pages.
Birbrair et al., Role of pericytes in skeletal muscle regeneration and fat accumulation. Stem Cells Dev. Aug. 15, 2013;22(16):2298-314.
Birbrair et al., Type-2 pericytes participate in normal and tumoral angiogenesis. Am J Physiol Cell Physiol. Jul. 1, 2014;307(1):C25-38.
Blanpain et al., Stem cells assessed. Nat Rev Mol Cell Biol. Jun. 8, 2012;13(7):471-6.
Blocki et al., Not all MSCs can act as pericytes: functional in vitro assays to distinguish pericytes from other mesenchymal stem cells in angiogenesis. Stem Cells Dev. Sep. 1, 2013;22(17):2347-55.
Bloom et al., Disodium (R,R)-5-[2-[[2-(3-chlorophenyl)-2-hydroxyethyl]-amino] propyl]-1,3-benzodioxole-2,2-dicarboxylate (CL 316,243). A potent beta-adrenergic agonist virtually specific for beta 3 receptors. A promising antidiabetic and antiobesity agent. J Med Chem. Aug. 7, 1992;35(16):3081-4.
Blum et al., The tumorigenicity of diploid and aneuploid human pluripotent stem cells. Cell Cycle. Dec. 2009;8(23):3822-30.
Bogos et al., VEGFR-3-positive circulating lymphatic/vascular endothelial progenitor cell level is associated with poor prognosis in human small cell lung cancer. Clin Cancer Res. Mar. 1, 2009;15(5):1741-6.
Bongso et al., Improved quality of human embryos when co-cultured with human ampullary cells. Hum Reprod. Aug. 1989;4(6):706-13.
Bongso et al., Isolation and culture of inner cell mass cells from human blastocysts. Hum Reprod. Nov. 1994;9(11):2110-7.
Bruno et al., Mesenchymal stem cell-derived microvesicles protect against acute tubular injury. J Am Soc Nephrol. May 2009;20(5):1053-67.
Camussi et al., Exosomes/microvesicles as a mechanism of cell-to-cell communication. Kidney Int. Nov. 2010;78(9):838-48.
Cannon et al., Brown adipose tissue: function and physiological significance. Physiol Rev. Jan. 2004;84(1):277-359.
Cannon et al., Cultures of adipose precursor cells from brown adipose tissue and of clonal brown-adipocyte-like cell lines. Methods Mol Biol. 2001;155:213-24.
Carmeliet, Angiogenesis in life, disease and medicine. Nature. Dec. 15, 2005;438(7070):932-6.
Cheema et al., Regulation and guidance of cell behavior for tissue regeneration via the siRNA mechanism. Wound Repair Regen. May-Jun. 2007;15(3):286-95.
Chen et al., A model of focal ischemic stroke in the rat: reproducible extensive cortical infarction. Stroke. Jul.-Aug. 1986;17(4):738-43.
Chen et al., Enabling a robust scalable manufacturing process for therapeutic exosomes through oncogenic immortalization of human ESC-derived MSCs. J Transl Med. Apr. 25, 2011;9:47. 10 pages.
Chen et al., Human myocardial pericytes: multipotent mesodermal precursors exhibiting cardiac specificity. Stem Cells. Feb. 2015;33(2):557-73.
Chen et al., Human pericytes for ischemic heart repair. Stem Cells. Feb. 2013;31(2):305-16.
Chung et al., Human embryonic stem cell lines generated without embryo destruction. Cell Stem Cell. Feb. 7, 2008;2(2):113-7.
Cibelli et al., Transgenic bovine chimeric offspring produced from somatic cell-derived stem-like cells. Nat Biotechnol. Jul. 1998;16(7):642-6.

(56) References Cited

OTHER PUBLICATIONS

Climent et al., TGFbeta Triggers miR-143/145 Transfer From Smooth Muscle Cells to Endothelial Cells, Thereby Modulating Vessel Stabilization. Circ Res. May 22, 2015;116(11):1753-64.

Cohen et al., Turning straw into gold: directing cell fate for regenerative medicine. Nat Rev Genet. Apr. 2011;12(4):243-52.

Conley et al., BMPs regulate differentiation of a putative visceral endoderm layer within human embryonic stem-cell-derived embryoid bodies. Biochem Cell Biol. Feb. 2007;85(1):121-32.

Cooper et al., Modulation of PGC-1 coactivator pathways in brown fat differentiation through LRP130. J Biol Chem. Nov. 14, 2008;283(46):31960-7.

Corselli et al., Identification of perivascular mesenchymal stromal/stem cells by flow cytometry. Cytometry A. Aug. 2013;83(8):714-20.

Costa et al., The hESC line Envy expresses high levels of GFP in all differentiated progeny. Nat Methods. Apr. 2005;2(4):259-60.

Costa et al., The hESC line Envy expresses high levels of GFP in all differentiated progeny. Nat Methods. Apr. 2005;2(4):259-60. Advance online publication.

Crook et al., The generation of six clinical-grade human embryonic stem cell lines. Cell Stem Cell. Nov. 2007;1(5):490-4.

Dai et al., MicroRNA-223-3p inhibits the angiogenesis of ischemic cardiac microvascular endothelial cells via affecting RPS6KB1/hif-1a signal pathway. PLoS One. Oct. 14, 2014;9(10):e108468. 14 pages.

Daneman et al., Pericytes are required for blood-brain barrier integrity during embryogenesis. Nature. Nov. 25, 2010;468(7323):562-6.

Dar et al., Multipotent vasculogenic pericytes from human pluripotent stem cells promote recovery of murine ischemic limb. Circulation. Jan. 3, 2012;125(1):87-99.

De Souza Batista et al., Omentin plasma levels and gene expression are decreased in obesity. Diabetes. Jun. 2007;56(6):1655-61.

Dechesne et al., Stem Cells from Human Adipose Tissue: A New Tool for Pharmacological Studies and for Clinical Applications. Adipose Stem Cells and Regenerative Medicine. Y.-G. Illouz (Ed.), Springer-Verlag Berlin Heidelberg. Chapter 12, pp. 121-132, (2011).

Deregibus et al., Endothelial progenitor cell derived microvesicles activate an angiogenic program in endothelial cells by a horizontal transfer of mRNA. Blood. Oct. 1, 2007;110(7):2440-8.

Desandro et al., Associations and interactions between bare lymphocyte syndrome factors. Mol Cell Biol. Sep. 2000;20(17):6587-99.

Dore-Duffy et al., Morphology and properties of pericytes. Methods Mol Biol. 2011;686:49-68.

Dubois et al., SIRPA is a specific cell-surface marker for isolating cardiomyocytes derived from human pluripotent stem cells. Nat Biotechnol. Oct. 23, 2011;29(11):1011-8.

Durick et al., Hunting with traps: genome-wide strategies for gene discovery and functional analysis. Genome Res. Nov. 1999;9(11):1019-25.

Díez et al., Endothelial progenitor cells undergo an endothelial-to-mesenchymal transition-like process mediated by TGFbetaRI. Cardiovasc Res. Dec. 1, 2010;88(3):502-11.

Elabd et al., Human multipotent adipose-derived stem cells differentiate into functional brown adipocytes. Stem Cells. Nov. 2009;27(11):2753-60.

Elali et al., The role of pericytes in neurovascular unit remodeling in brain disorders. Int J Mol Sci. Apr. 16, 2014;15(4):6453-74.

Espandar et al., Adipose-derived stem cells on hyaluronic acid-derived scaffold: a new horizon in bioengineered cornea. Arch Ophthalmol. Feb. 2012;130(2):202-8.

Fedorenko et al., Mechanism of fatty-acid-dependent UCP1 uncoupling in brown fat mitochondria. Cell. Oct. 12, 2012;151(2):400-13.

Ferrari et al., Transforming growth factor-beta 1 (TGF-beta1) induces angiogenesis through vascular endothelial growth factor (VEGF)-mediated apoptosis. J Cell Physiol. May 2009;219(2):449-58.

Fish et al., miR-126 regulates angiogenic signaling and vascular integrity. Dev Cell. Aug. 2008;15(2):272-84.

Follenzi et al., Gene transfer by lentiviral vectors is limited by nuclear translocation and rescued by HIV-1 pol sequences. Nat Genet. Jun. 2000;25(2):217-22.

Forte et al., MicroRNA-mediated transformation by the Kaposi's sarcoma-associated herpesvirus Kaposin locus. J Virol. Feb. 2015;89(4):2333-41.

Francavilla et al., Transient GFER knockdown in vivo impairs liver regeneration after partial hepatectomy. Int J Biochem Cell Biol. Aug. 2014;53:343-51.

Fu et al., Endothelial cell O-glycan deficiency causes blood/lymphatic misconnections and consequent fatty liver disease in mice. J Clin Invest. Nov. 2008;118(11):3725-37.

Funk et al., Evaluating the genomic and sequence integrity of human ES cell lines; comparison to normal genomes. Stem Cell Res. Mar. 2012;8(2):154-64.

Gao et al., Endothelial progenitor cells control the angiogenic switch in mouse lung metastasis. Science. Jan. 11, 2008;319(5860):195-8.

Garbuzova-Davis et al., Blood-CNS Barrier Impairment in ALS patients versus an animal model. Front Cell Neurosci. Feb. 3, 2014;8:21. 10 pages.

Garcia et al., Glucose Starvation in Cardiomyocytes Enhances Exosome Secretion and Promotes Angiogenesis in Endothelial Cells. PLoS One. Sep. 22, 2015;10(9):e0138849. 23 pages.

Gardner et al., Culture and transfer of human blastocysts increases implantation rates and reduces the need for multiple embryo transfers. Fertil Steril. Jan. 1998;69(1):84-8.

Gehling et al., In vitro differentiation of endothelial cells from AC133-positive progenitor cells. Blood. May 15, 2000;95(10):3106-12.

George et al., Isolation of human platelet membrane microparticles from plasma and serum. Blood. Oct. 1982;60(4):834-40.

Goldman et al., A boost of BMP4 accelerates the commitment of human embryonic stem cells to the endothelial lineage. Stem Cells. Aug. 2009;27(8):1750-9.

Golozoubova et al., Only UCP1 can mediate adaptive nonshivering thermogenesis in the cold. FASEB J. Sep. 2001;15(11):2048-50.

Goumans et al., TGF-beta signaling in vascular biology and dysfunction. Cell Res. Jan. 2009;19(1):116-27.

Grigolo et al., Transplantation of chondrocytes seeded on a hyaluronan derivative (hyaff-11) into cartilage defects in rabbits. Biomaterials. Sep. 2001;22(17):2417-24.

Grützkau et al., Small but mighty: how the MACS-technology based on nanosized superparamagnetic particles has helped to analyze the immune system within the last 20 years. Cytometry A. Jul. 2010;77(7):643-7.

Guduric-Fuchs et al., Selective extracellular vesicle-mediated export of an overlapping set of microRNAs from multiple cell types. BMC Genomics. Aug. 1, 2012;13:357. 14 pages.

Haflidadóttir et al., Upregulation of miR-96 enhances cellular proliferation of prostate cancer cells through FOXO1. PLoS One. Aug. 12, 2013;8(8):e72400. 11 pages.

Harms et al., Brown and beige fat: development, function and therapeutic potential. Nat Med. Oct. 2013;19(10):1252-63.

Hassan et al., Encapsulation and 3D culture of human adipose-derived stem cells in an in-situ crosslinked hybrid hydrogel composed of PEG-based hyperbranched copolymer and hyaluronic acid. Stem Cell Res Ther. Mar. 21, 2013;4(2):32. 11 pages.

Hedman et al., Isolation of the pericellular matrix of human fibroblast cultures. J Cell Biol. Apr. 1979;81(1):83-91.

Hemmrich et al., Implantation of preadipocyte-loaded hyaluronic acid-based scaffolds into nude mice to evaluate potential for soft tissue engineering. Biomaterials. Dec. 2005;26(34):7025-37.

Heo et al., Spontaneous differentiation of mouse embryonic stem cells in vitro: characterization by global gene expression profiles. Biochem Biophys Res Commun. Jul. 15, 2005;332(4):1061-9.

Herrera et al., Human liver stem cell-derived microvesicles accelerate hepatic regeneration in hepatectomized rats. J Cell Mol Med. Jun. 2010;14(6B):1605-18.

Ho et al., Synthetic protein transduction domains: enhanced transduction potential in vitro and in vivo. Cancer Res. Jan. 15, 2001;61(2):474-7.

(56) References Cited

OTHER PUBLICATIONS

Honda et al., Cartilage formation by cultured chondrocytes in a new scaffold made of poly(L-lactide-epsilon-caprolactone) sponge. J Oral Maxillofac Surg. Jul. 2000;58(7):767-75.
Huber et al., Haemangioblast commitment is initiated in the primitive streak of the mouse embryo. Nature. Dec. 2, 2004;432(7017):625-30.
Hynes et al., Micropatterning of 3D Microenvironments for Living Biosensor Applications. Biosensors (Basel). Mar. 2014;4(1):28-44.
Hölig et al., Novel RGD lipopeptides for the targeting of liposomes to integrin-expressing endothelial and melanoma cells. Protein Eng Des Sel. May 2004;17(5):433-41.
Hüttemann et al., Mice deleted for heart-type cytochrome c oxidase subunit 7a1 develop dilated cardiomyopathy. Mitochondrion. Mar. 2012;12(2):294-304.
Ibrahim et al., Exosomes as critical agents of cardiac regeneration triggered by cell therapy. Stem Cell Reports. May 8, 2014;2(5):606-19.
Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.
Jackson et al., Recognizing and avoiding siRNA off-target effects for target identification and therapeutic application. Nat Rev Drug Discov. Jan. 2010;9(1):57-67.
Jaiswal et al., Long-term multiple color imaging of live cells using quantum dot bioconjugates. Nat Biotechnol. Jan. 2003;21(1):47-51.
Jakob et al., Role of microRNAs in stem/progenitor cells and cardiovascular repair. Cardiovasc Res. Mar. 15, 2012;93(4):614-22.
James et al., An abundant perivascular source of stem cells for bone tissue engineering. Stem Cells Transl Med. Sep. 2012;1(9):673-84.
James et al., Contribution of human embryonic stem cells to mouse blastocysts. Dev Biol. Jul. 1, 2006;295(1):90-102.
James et al., Expansion and maintenance of human embryonic stem cell-derived endothelial cells by TGFbeta inhibition is Id1 dependent. Nat Biotechnol. Feb. 2010;28(2):161-6.
Jankovic et al., Id1 restrains myeloid commitment, maintaining the self-renewal capacity of hematopoietic stem cells. Proc Natl Acad Sci U S A. Jan. 23, 2007;104(4):1260-5.
Jeong et al., Nanovesicles engineered from ES cells for enhanced cell proliferation. Biomaterials. Nov. 2014;35(34):9302-10.
Kane et al., Derivation of endothelial cells from human embryonic stem cells by directed differentiation: analysis of microRNA and angiogenesis in vitro and in vivo. Arterioscler Thromb Vasc Biol. Jul. 2010;30(7):1389-97.
Kang et al., A self-enabling TGFbeta response coupled to stress signaling: Smad engages stress response factor ATF3 for Id1 repression in epithelial cells. Mol Cell. Apr. 2003;11(4):915-26.
Karamanlidis et al., C/EBPbeta reprograms white 3T3-L1 preadipocytes to a Brown adipocyte pattern of gene expression. J Biol Chem. Aug. 24, 2007;282(34):24660-9.
Kawamoto et al., Role of progenitor endothelial cells in cardiovascular disease and upcoming therapies. Catheter Cardiovasc Interv. Oct. 1, 2007;70(4):477-84.
Kawasaki et al., Vascular Repair by Tissue-Resident Endothelial Progenitor Cells in Endotoxin-Induced Lung Injury. Am J Respir Cell Mol Biol. Oct. 2015;53(4):500-12.
Kazantzis et al., PAZ6 cells constitute a representative model for human brown pre-adipocytes. Front Endocrinol (Lausanne). Feb. 2, 2012;3:13.
Keller et al., Exosomes: from biogenesis and secretion to biological function. Immunol Lett. Nov. 15, 2006;107(2):102-8.
Kelly et al., Signaling hierarchy regulating human endothelial cell development. Arterioscler Thromb Vasc Biol. May 2009;29(5):718-24.
Khakoo et al., Endothelial progenitor cells. Annu Rev Med. 2005;56:79-101.
Kim et al., Extracellular membrane vesicles from tumor cells promote angiogenesis via sphingomyelin. Cancer Res. Nov. 1, 2002;62(21):6312-7.
King et al., Hypoxic enhancement of exosome release by breast cancer cells. BMC Cancer. Sep. 24, 2012;12:421. 10 pages.
Korchagin, Neoplastic Diseases Reviews, Stem Cells. CancerLink.ru. 26 pages, (2011).
Krosl et al., In vitro expansion of hematopoietic stem cells by recombinant TAT-HOXB4 protein. Nat Med. Nov. 2003;9(11):1428-32.
Kucharzewska et al., Exosomes reflect the hypoxic status of glioma cells and mediate hypoxia-dependent activation of vascular cells during tumor development. PNAS. Apr. 30, 2013;110(18):7312-7317.
Lai et al., Animal models of diabetic retinopathy: summary and comparison. J Diabetes Res. 2013;2013:106594. 29 pages.
Laine et al., MicroRNAs miR-96, miR-124, and miR-199a regulate gene expression in human bone marrow-derived mesenchymal stem cells. J Cell Biochem. Aug. 2012;113(8):2687-95.
Lanza et al., Human therapeutic cloning. Nat Med. Sep. 1999;5(9):975-7.
Laping et al., Inhibition of transforming growth factor (TGF)-beta1-induced extracellular matrix with a novel inhibitor of the TGF-beta type I receptor kinase activity: SB-431542. Mol Pharmacol. Jul. 2002;62(1):58-64.
Laposa, Stem cells for drug screening. J Cardiovasc Pharmacol. Sep. 2011;58(3):240-5.
Le Grand et al., Six1 regulates stem cell repair potential and self-renewal during skeletal muscle regeneration. J Cell Biol. Sep. 3, 2012;198(5):815-32.
Lee et al., Deletion of heart-type cytochrome c oxidase subunit 7a1 impairs skeletal muscle angiogenesis and oxidative phosphorylation. J Physiol. Oct. 15, 2012;590(20):5231-43.
Lee et al., Exosomes mediate the cytoprotective action of mesenchymal stromal cells on hypoxia-induced pulmonary hypertension. Circulation. Nov. 27, 2012;126(22):2601-11.
Lee et al., HLA-E is a major ligand for the natural killer inhibitory receptor CD94/NKG2A. Proc Natl Acad Sci U S A. Apr. 28, 1998;95(9):5199-204.
Levenberg et al., Endothelial cells derived from human embryonic stem cells. Proc Natl Acad Sci U S A. Apr. 2, 2002;99(7):4391-6.
Levenberg et al., Endothelial potential of human embryonic stem cells. Blood. Aug. 1, 2007;110(3):806-14.
Li et al., Comparison of reporter gene and iron particle labeling for tracking fate of human embryonic stem cells and differentiated endothelial cells in living subjects. Stem Cells. Apr. 2008;26(4):864-73.
Limbourg et al., Evaluation of postnatal arteriogenesis and angiogenesis in a mouse model of hind-limb ischemia. Nat Protoc. 2009;4(12):1737-48.
Lin et al., Quantum dot imaging for embryonic stem cells. BMC Biotechnol. Oct. 9, 2007;7:67. 10 pages.
Lin et al., Unregulated miR-96 induces cell proliferation in human breast cancer by downregulating transcriptional factor FOXO3a. PLoS One. Dec. 23, 2010;5(12):e15797. 10 pages.
Liu et al., MiR-106b and MiR-15b modulate apoptosis and angiogenesis in myocardial infarction. Cell Physiol Biochem. 2012;29(5-6):851-62.
Lopatina et al., Platelet-derived growth factor regulates the secretion of extracellular vesicles by adipose mesenchymal stem cells and enhances their angiogenic potential. Cell Commun Signal. Apr. 11, 2014;12:26. 12 pages.
Lu et al., Generation of functional hemangioblasts from human embryonic stem cells. Nat Methods. Jun. 2007;4(6):501-9.
Lu et al., Targeting of embryonic stem cells by peptide-conjugated quantum dots. PLoS One. Aug. 10, 2010;5(8):e12075. 10 pages.
Lyden et al., Impaired recruitment of bone-marrow-derived endothelial and hematopoietic precursor cells blocks tumor angiogenesis and growth. Nat Med. Nov. 2001;7(11):1194-201.
Mali et al., Improved efficiency and pace of generating induced pluripotent stem cells from human adult and fetal fibroblasts. Stem Cells. Aug. 2008;26(8):1998-2005.
Martinez et al., Shed membrane microparticles from circulating and vascular cells in regulating vascular function. Am J Physiol Heart Circ Physiol. Mar. 2005;288(3):H1004-9.

(56) References Cited

OTHER PUBLICATIONS

Molek et al., Peptide phage display as a tool for drug discovery: targeting membrane receptors. Molecules. Jan. 21, 2011;16(1):857-87.
Nakagawa et al., Reprogramming of somatic cells to pluripotency. Adv Exp Med Biol. 2010;695:215-24.
Nakashiba et al., Netrin-G1: a novel glycosyl phosphatidylinositol-linked mammalian netrin that is functionally divergent from classical netrins. J Neurosci. Sep. 1, 2000;20(17):6540-50.
Naldini et al., In vivo gene delivery and stable transduction of nondividing cells by a lentiviral vector. Science. Apr. 12, 1996;272(5259):263-7.
Nelson et al., Induced pluripotent stem cells: advances to applications. Stem Cells Cloning. Jan. 1, 2010;3:29-37.
Nicoli et al., MicroRNA-mediated integration of haemodynamics and Vegf signalling during angiogenesis. Nature. Apr. 22, 2010;464(7292):1196-200.
Niemelä et al., Molecular identification of PAL-E, a widely used endothelial-cell marker. Blood. Nov. 15, 2005;106(10):3405-9.
Nishio et al., Production of functional classical brown adipocytes from human pluripotent stem cells using specific hemopoietin cocktail without gene transfer. Cell Metab. Sep. 5, 2012;16(3):394-406.
Nonaka et al., Development of stabilin2+ endothelial cells from mouse embryonic stem cells by inhibition of TGFbeta/activin signaling. Biochem Biophys Res Commun. Oct. 17, 2008;375(2):256-60.
Nourse et al., VEGF induces differentiation of functional endothelium from human embryonic stem cells: implications for tissue engineering. Arterioscler Thromb Vasc Biol. Jan. 2010;30(1):80-9.
Odaka, Localization of mesenchymal cells in adult mouse thymus: their abnormal distribution in mice with disorganization of thymic medullary epithelium. J Histochem Cytochem. Apr. 2009;57(4):373-82.
Ohshima et al., Let-7 microRNA family is selectively secreted into the extracellular environment via exosomes in a metastatic gastric cancer cell line. PLoS One. Oct. 8, 2010;5(10):e13247. 10 pages.
Ong et al., Cross talk of combined gene and cell therapy in ischemic heart disease: role of exosomal microRNA transfer. Circulation. Sep. 9, 2014;130(11 Suppl 1):S60-9.
Orlova et al., Functionality of endothelial cells and pericytes from human pluripotent stem cells demonstrated in cultured vascular plexus and zebrafish xenografts. Arterioscler Thromb Vasc Biol. Jan. 2014;34(1):177-86.
Pankratz et al., MicroRNA-155 Exerts Cell-Specific Antiangiogenic but Proarteriogenic Effects During Adaptive Neovascularization. Circulation. May 5, 2015;131(18):1575-89.
Patel et al., Poly(ethylene glycol) hydrogel system supports preadipocyte viability, adhesion, and proliferation. Tissue Eng. Sep.-Oct. 2005;11(9-10):1498-505.
Peichev et al., Expression of VEGFR-2 and AC133 by circulating human CD34(+) cells identifies a population of functional endothelial precursors. Blood. Feb. 1, 2000;95(3):952-8.
Perka et al., Joint cartilage repair with transplantation of embryonic chondrocytes embedded in collagen-fibrin matrices. Clin Exp Rheumatol. Jan.-Feb. 2000;18(1):13-22.
Prestwich et al., The translational imperative: making cell therapy simple and effective. Acta Biomater. Dec. 2012;8(12):4200-7.
Rafii et al., Cancer. A few to flip the angiogenic switch. Science. Jan. 11, 2008;319(5860):163-4.
Ragni et al., Adipogenic potential in human mesenchymal stem cells strictly depends on adult or foetal tissue harvest. Int J Biochem Cell Biol. Nov. 2013;45(11):2456-66.
Ramskold et al., An abundance of ubiquitously expressed genes revealed by tissue transcriptome sequence data. PLoS Comput Biol. 2009;5(12):e1000598, 11 pages.
Rasmussen et al., TNFerade Biologic: preclinical toxicology of a novel adenovector with a radiation-inducible promoter, carrying the human tumor necrosis factor alpha gene. Cancer Gene Ther. Nov. 2002;9(11):951-7.
Religa et al., Presence of bone marrow-derived circulating progenitor endothelial cells in the newly formed lymphatic vessels. Blood. Dec. 15, 2005;106(13):4184-90.
Reubinoff et al., Embryonic stem cell lines from human blastocysts: somatic differentiation in vitro. Nat Biotechnol. Apr. 2000;18(4):399-404.
Rhie et al., Implantation of Cultured Preadipocyte Using Chitosan/Alginate Sponge. Key Engineering Materials. 2007;342-343;349-352.
Riolobos et al., HLA engineering of human pluripotent stem cells. Mol Ther. Jun. 2013;21(6):1232-41.
Rong et al., A scalable approach to prevent teratoma formation of human embryonic stem cells. J Biol Chem. Sep. 21, 2012;287(39):32338-45.
Rong et al., An effective approach to prevent immune rejection of human ESC-derived allografts. Cell Stem Cell. Jan. 2, 2014;14(1):121-30.
Rosensteel et al., COL1A1 oligodeoxynucleotides decoy: biochemical and morphologic effects in an acute wound repair model. Exp Mol Pathol. Dec. 2010;89(3):307-13.
Rosler et al., Long-term culture of human embryonic stem cells in feeder-free conditions. Dev Dyn. Feb. 2004;229(2):259-74.
Rossig et al., Histone deacetylase activity is essential for the expression of HoxA9 and for endothelial commitment of progenitor cells. J Exp Med. Jun. 6, 2005;201(11):1825-35.
Rudert et al., Bioartificial Cartilage. Cells Tissues Organs. 2000;167:95-105.
Ruzinova et al., Id proteins in development, cell cycle and cancer. Trends Cell Biol. Aug. 2003;13(8):410-8.
Sagare et al., Pericyte loss influences Alzheimer-like neurodegeneration in mice. Nat Commun. 2013;4:2932. 14 pages.
Sahoo et al., Exosomes from human CD34(+) stem cells mediate their proangiogenic paracrine activity. Circ Res. Sep. 16, 2011;109(7):724-8.
Salven et al., VEGFR-3 and CD133 identify a population of CD34+ lymphatic/vascular endothelial precursor cells. Blood. Jan. 1, 2003;101(1):168-72.
Schnerch et al., Distinguishing between mouse and human pluripotent stem cell regulation: the best laid plans of mice and men. Stem Cells. Mar. 31, 2010;28(3):419-30.
Schniedermann et al., Mouse lung contains endothelial progenitors with high capacity to form blood and lymphatic vessels. BMC Cell Biology. 2010;11(50):1-13.
Schulz et al., Identification of inducible brown adipocyte progenitors residing in skeletal muscle and white fat. Proc Natl Acad Sci U S A. Jan. 4, 2011;108(1):143-8.
Schwarze et al., In vivo protein transduction: intracellular delivery of biologically active proteins, compounds and DNA. Trends Pharmacol Sci. Feb. 2000;21(2):45-8.
Scott et al., Current methods of adipogenic differentiation of mesenchymal stem cells. Stem Cells Dev. Oct. 2011;20(10):1793-804.
Seale et al., PRDM16 controls a brown fat/skeletal muscle switch. Nature. Aug. 21, 2008;454(7207):961-7.
Seandel et al., Generation of a functional and durable vascular niche by the adenoviral E4ORF1 gene. Proc Natl Acad Sci U S A. Dec. 9, 2008;105(49):19288-93.
Semo et al., The 106b~25 microRNA cluster is essential for neovascularization after hindlimb ischaemia in mice. Eur Heart J. Dec. 1, 2014;35(45):3212-23.
Shah et al., Labeling of mesenchymal stem cells by bioconjugated quantum dots. Nano Lett. Oct. 2007;7(10):3071-9.
Shehzad et al., Adiponectin: regulation of its production and its role in human diseases. Hormones (Athens). Jan.-Mar. 2012;11(1):8-20.
Slotkin et al., In vivo quantum dot labeling of mammalian stem and progenitor cells. Dev Dyn. Dec. 2007;236(12):3393-401.
Sobrino et al., The increase of circulating endothelial progenitor cells after acute ischemic stroke is associated with good outcome. Stroke. Oct. 2007;38(10):2759-64.
Solter et al., Immunosurgery of mouse blastocyst. Proc Natl Acad Sci U S A. Dec. 1975;72(12):5099-102.

(56) References Cited

OTHER PUBLICATIONS

Sone et al., Pathway for differentiation of human embryonic stem cells to vascular cell components and their potential for vascular regeneration. Arterioscler Thromb Vasc Biol. Oct. 2007;27(10):2127-34.

Song et al., Modeling disease in human ESCs using an efficient BAC-based homologous recombination system. Cell Stem Cell. Jan. 8, 2010;6(1):80-9.

Spear et al., Isolation, characterization, and recovery of small peptide phage display epitopes selected against viable malignant glioma cells. Cancer Gene Ther. Jul. 2001;8(7):506-11.

Spinetti et al., MicroRNA-15a and microRNA-16 impair human circulating proangiogenic cell functions and are increased in the proangiogenic cells and serum of patients with critical limb ischemia. Circ Res. Jan. 18, 2013;112(2):335-46.

Sternberg et al., A human embryonic stem cell-derived clonal progenitor cell line with chondrogenic potential and markers of craniofacial mesenchyme. Regen Med. Jul. 2012;7(4):481-501.

Stojkovic et al., An autogeneic feeder cell system that efficiently supports growth of undifferentiated human embryonic stem cells. Stem Cells. Mar. 2005;23(3):306-14.

Suzuki et al., BMPs promote proliferation and migration of endothelial cells via stimulation of VEGF-A/VEGFR2 and angiopoietin-1/Tie2 signalling. J Biochem. Feb. 2008;143(2):199-206.

Suárez et al., MicroRNAs as novel regulators of angiogenesis. Circ Res. Feb. 27, 2009;104(4):442-54.

Svensson et al., Gene expression in human brown adipose tissue. Int J Mol Med. Feb. 2011;27(2):227-32.

Tadokoro et al., Exosomes derived from hypoxic leukemia cells enhance tube formation in endothelial cells. J Biol Chem. Nov. 29, 2013;288(48):34343-51.

Takahashi et al., Induction of pluripotent stem cells from adult human fibroblasts by defined factors. Cell. Nov. 30, 2007;131(5):861-72.

Tchkonia et al., Fat depot origin affects adipogenesis in primary cultured and cloned human preadipocytes. Am J Physiol Regul Integr Comp Physiol. May 2002;282(5):R1286-96.

Tchkonia et al., Identification of depot-specific human fat cell progenitors through distinct expression profiles and development gene patterns. Am J Physiol Endocrinol Metab. 2007;292:E298-E307.

Teesalu et al., Mapping of vascular ZIP codes by phage display. Methods Enzymol. 2012;503:35-56.

Thomson et al., Embryonic stem cell lines derived from human blastocysts. Science. Nov. 6, 1998;282(5391):1145-7.

Thomson et al., Isolation of a primate embryonic stem cell line. Proc Natl Acad Sci U S A. Aug. 15, 1995;92(17):7844-8.

Thomson et al., Primate embryonic stem cells. Curr Top Dev Biol. 1998;38:133-65.

Thumser et al., Fatty acid binding proteins: tissue-specific functions in health and disease. Curr Opin Clin Nutr Metab Care. Mar. 2014;17(2):124-9.

Tiscornia et al., Diseases in a dish: modeling human genetic disorders using induced pluripotent cells. Nat Med. Dec. 2011;17(12):1570-6.

Tsuchida et al., Inhibitors of the TGF-beta superfamily and their clinical applications. Mini Rev Med Chem. Nov. 2006;6(11):1255-61.

Van Der Lans et al., Cold-activated brown adipose tissue in human adults: methodological issues. Am J Physiol Regul Integr Comp Physiol. Jul. 15, 2014;307(2):R103-13.

Wagner et al., Replicative senescence of mesenchymal stem cells: a continuous and organized process. PLoS One. May 21, 2008;3(5):e2213. 12 pages.

Wang et al., Endothelial cells derived from human embryonic stem cells form durable blood vessels in vivo. Nat Biotechnol. Mar. 2007;25(3):317-8.

Wanjare et al., Defining differences among perivascular cells derived from human pluripotent stem cells. Stem Cell Reports. Apr. 17, 2014;2(5):561-75.

Watabe et al., TGF-beta receptor kinase inhibitor enhances growth and integrity of embryonic stem cell-derived endothelial cells. J Cell Biol. Dec. 22, 2003;163(6):1303-11.

Watabe et al., TGF-beta Signaling in Embryonic Stem Cell-Derived Endothelial Cells. Methods in Molecular Biology, vol. 330: Embryonic Stem Cell Protocols, 2nd Edition: vol. 2. K. Turksen (Ed.) Humana Press Inc., Totowa, NJ. Chapter 23, pp. 341-351, (2006).

Watt et al., Human endothelial stem/progenitor cells, angiogenic factors and vascular repair. J R Soc Interface. Dec. 6, 2010;7 Suppl 6:S731-51.

West et al., Clonal derivation of white and brown adipocyte progenitor cell lines from human pluripotent stem cells. Stem Cell Res Ther. Jan. 8, 2019;10(1):7, 18 pages.

West et al., The ACTCellerate initiative: large-scale combinatorial cloning of novel human embryonic stem cell derivatives. Regen Med. May 2008;3(3):287-308.

Wilcock et al., Vascular amyloid alters astrocytic water and potassium channels in mouse models and humans with Alzheimer's disease. Neuroscience. Mar. 31, 2009:159(3):1055-69.

Winkler et al., Blood-spinal cord barrier breakdown and pericyte reductions in amyotrophic lateral sclerosis. Acta Neuropathol. Jan. 2013;125(1):111-20.

Wong et al., Pericytes, mesenchymal stem cells and their contributions to tissue repair. Pharmacol Ther. Jul. 2015;151:107-20.

Wu et al., Beige adipocytes are a distinct type of thermogenic fat cell in mouse and human. Cell. Jul. 20, 2012;150(2):366-76.

Wu et al., Molecular characterization, expression patterns and polymorphism analysis of porcine Six1 gene. Mol Biol Rep. Apr. 2011;38(4):2619-32.

Xin et al., Systemic administration of exosomes released from mesenchymal stromal cells promote functional recovery and neurovascular plasticity after stroke in rats. J Cereb Blood Flow Metab. Nov. 2013;33(11):1711-5.

Xu et al., BMP4 initiates human embryonic stem cell differentiation to trophoblast. Nat Biotechnol. Dec. 2002;20(12):1261-4.

Xu et al., Feeder-free growth of undifferentiated human embryonic stem cells. Nat Biotechnol. Oct. 2001;19(10):971-4.

Yamahara et al., Augmentation of neovascularization in hindlimb ischemia by combined transplantation of human embryonic stem cells-derived endothelial and mural cells. PLoS One. Feb. 27, 2008;3(2):e1666. 11 pages.

Yamamoto et al., Circulating adiponectin levels and risk of type 2 diabetes in the Japanese. Nutr Diabetes. Aug. 18, 2014;4:e130. 5 pages.

Yamashita et al., Flk1-positive cells derived from embryonic stem cells serve as vascular progenitors. Nature. Nov. 2, 2000;408(6808):92-6.

Yang et al., Human cardiovascular progenitor cells develop from a KDR+ embryonic-stem-cell-derived population. Nature. May 22, 2008;453(7194):524-8.

Yemisci et al., Pericyte contraction induced by oxidative-nitrative stress impairs capillary reflow despite successful opening of an occluded cerebral artery. Nat Med. Sep. 2009;15(9):1031-7.

Yingling et al., Development of TGF-beta signalling inhibitors for cancer therapy. Nat Rev Drug Discov. Dec. 2004;3(12):1011-22.

Yoder, Human endothelial progenitor cells. Cold Spring Harb Perspect Med. Jul. 2012;2(7):a006692, 14 pages.

Yuan et al., Cell-surface marker signatures for the isolation of neural stem cells, glia and neurons derived from human pluripotent stem cells. PLoS One. Mar. 2, 2011;6(3):e17540. 16 pages.

Zaragoza et al., Animal models of cardiovascular diseases. J Biomed Biotechnol. 2011;2011:497841. 13 pages.

Zernecke et al., Delivery of microRNA-126 by apoptotic bodies induces CXCL12-dependent vascular protection. Sci Signal. Dec. 8, 2009;2(100):ra81.

Zhang et al., Microvesicles derived from human umbilical cord mesenchymal stem cells stimulated by hypoxia promote angiogenesis both in vitro and in vivo. Stem Cells Dev. Dec. 10, 2012;21(18):3289-97.

Zhao et al., Isolation and initial application of a novel peptide that specifically recognizes the neural stem cells derived from rhesus monkey embryonic stem cells. J Biomol Screen. Jul. 2010;15(6):687-94.

(56) References Cited

OTHER PUBLICATIONS

Zhao et al., Novel peptide ligands that bind specifically to mouse embryonic stem cells. Peptides. Nov. 2010;31(11):2027-34.
Zhong et al., Association of serum omentin-1 levels with coronary artery disease. Acta Pharmacol Sin. Jul. 2011;32(7):873-8.
Zilberfarb et al., Human immortalized brown adipocytes express functional beta3- adrenoceptor coupled to lipolysis. J Cell Sci. Apr. 1997;110 ( Pt 7):801-7.
Zou et al., Two functional microRNA-126s repress a novel target gene p21-activated kinase 1 to regulate vascular integrity in zebrafish. Circ Res. Jan. 21, 2011;108(2):201-9.
Zwaka et al., A germ cell origin of embryonic stem cells? Development. Jan. 2005;132(2):227-33.
Chen et al., Advances in the developmental origin of brown adipocyte. Chinese Bulletin of Life Sciences. 2013;25(7):661-668.
Genecards, ADIPOQ Gene. Retrieved online at: https://www.genecards.org/cgi-bin/carddisp.p?gene=ADIPOQ#protein_expression. 27 pages, 2021.
Liu et al., CD31: beyond a marker for endothelial cells. Cardiovasc Res. Apr. 1, 2012;94(1):3-5.
Nowakowski et al., Genetic engineering of stem cells for enhanced therapy. Acta Neurobiol Exp (Wars). 2013;73(1):1-18.
Thery et al., Isolation and characterization of exosomes from cell culture supernatants and biological fluids. Curr Protoc Cell Biol. Apr. 2006; Chapter 3:Unit 3.22.1-3.22.29.
Alle et al., A single short reprogramming early in life improves fitness and increases lifespan in old age. bioRxiv, https://doi.org/10.1101/2021.05.13.443979. 56 pages, May 14, 2021.
Beyret et al., Elixir of Life: Thwarting Aging With Regenerative Reprogramming. Circ Res. Jan. 5, 2018;122(1):128-141.
Chakritbudsabong et al., Exogenous LIN28 Is Required for the Maintenance of Self-Renewal and Pluripotency in Presumptive Porcine-Induced Pluripotent Stem Cells. Front Cell Dev Biol. Jul. 20, 2021;9:709286, 16 pages.
Chiavellini et al., Aging and rejuvenation—a modular epigenome model. Aging (Albany NY). Feb. 24, 2021;13(4):4734-4746.
Chiche et al., Injury-Induced Senescence Enables In Vivo Reprogramming in Skeletal Muscle. Cell Stem Cell. Mar. 2, 2017;20(3):407-414.e4.
Doeser et al., Reduction of Fibrosis and Scar Formation by Partial Reprogramming In Vivo. Stem Cells. Aug. 2018;36(8):1216-1225.
Ghaedi et al., Human Pluripotent Stem Cells (iPSC) Generation, Culture, and Differentiation to Lung Progenitor Cells. Methods Mol Biol. 2019;1576:55-92.
Gill et al., Multi-omic rejuvenation of human cells by maturation phase transient reprogramming. bioRxiv, https://doi.org/10.1101/2021.01.15.426786. 25 pages, Jan. 17, 2021.
Han et al., Induced pluripotent stem cells: emerging techniques for nuclear reprogramming. Antioxid Redox Signal. Oct. 1, 2011;15(7):1799-820.
Jun-Hao et al., Lin28 and let-7 in the Metabolic Physiology of Aging. Trends Endocrinol Metab. Mar. 2016;27(3):132-141.
Kane et al., Epigenetic changes during aging and their reprogramming potential. Crit Rev Biochem Mol Biol. Feb. 2019;54(1):61-83.
Kidder et al., Examination of transcriptional networks reveals an important role for TCFAP2C, SMARCA4, and EOMES in trophoblast stem cell maintenance. Genome Res. Apr. 2010;20(4):458-72.
Ledford, Reversal of biological clock restores vision in old mice. Nature. Dec. 2020;588(7837):209.
Lu et al., Reprogramming to recover youthful epigenetic information and restore vision. Nature. Dec. 2020;588(7836):124-129.
Martinez-Redondo et al., Tailored chromatin modulation to promote tissue regeneration. Semin Cell Dev Biol. Jan. 2020;97:3-15, pre-publication edition.
Menendez et al., Metabolic control of cancer cell stemness: Lessons from iPS cells. Cell Cycle. 2015;14(24):3801-11.
Mosteiro et al., Tissue damage and senescence provide critical signals for cellular reprogramming in vivo. Science. Nov. 25, 2016;354(6315):aaf4445, 12 pages.
Nguyen et al., Lin28 and let-7 in cell metabolism and cancer. Transl Pediatr. Jan. 2015;4(1):4-11.
Ofenbauer et al., Strategies for in vivo reprogramming. Curr Opin Cell Biol. Dec. 2019;61:9-15.
Parisi et al., Identification of RNA-binding proteins that partner with Lin28a to regulate Dnmt3a expression. Sci Rep. Jan. 27, 2021;11(1):2345, 13 pages.
Rando et al., Aging, rejuvenation, and epigenetic reprogramming: resetting the aging clock. Cell. Jan. 20, 2012;148(1-2):46-57.
Richardson et al., Endothelial progenitor cells: quo vadis? J Mol Cell Cardiol. Feb. 2011;50(2):266-72.
Romer-Seibert et al., The RNA-binding protein LIN28 controls progenitor and neuronal cell fate during postnatal neurogenesis. FASEB J. Mar. 2019;33(3):3291-3303, pre-publication edition.
Roux et al., Partial reprogramming restores youthful gene expression through transient suppression of cell identity. bioRxiv. https://doi.org/10.1101/2021.05.21.444556. 29 pages, May 23, 2021.
Sarkar et al., Transient non-integrative expression of nuclear reprogramming factors promotes multifaceted amelioration of aging in human cells. Nat Commun. Mar. 24, 2020;11(1):1545, 12 pages.
Suva et al., Epigenetic reprogramming in cancer. Science. Mar. 29, 2013;339(6127):1567-70.
Takahashi et al., Induction of pluripotent stem cells from mouse embryonic and adult fibroblast cultures by defined factors. Cell. Aug. 25, 2006;126(4):663-76.
Tsialikas et al., LIN28: roles and regulation in development and beyond. Development. Jul. 15, 2015;142(14):2397-404.
Vadla, lin-28 controls the succession of cell fate choices via two distinct activities. PLoS Genet. 2012;8(3):e1002588, 11 pages.
Mswanathan et al., Lin28 enhances tumorigenesis and is associated with advanced human malignancies. Nat Genet. Jul. 2009;41(7):843-8.
Viswanathan et al., Lin28: A microRNA regulator with a macro role. Cell. Feb. 19, 2010;140(4):445-9.
Wang et al., Lin28 Signaling Supports Mammalian PNS and CNS Axon Regeneration. Cell Rep. Sep. 4, 2018;24(10):2540-2552.
West et al., Toward a unified theory of aging and regeneration. Regen Med. Sep. 2019;14(9):867-886.
Wilbert et al., LIN28 binds messenger RNAs at GGAGA motifs and regulates splicing factor abundance. Mol Cell. Oct. 26, 2012;48(2):195-206.
Yilmazer et al., In vivo reprogramming of adult somatic cells to pluripotency by overexpression of Yamanaka factors. J Vis Exp. Dec. 17, 2013;(82):e50837, 9 pages.
Yoshitsugu et al., Importance of the structuration of cells in the differentiation process of human induced pluripotent stem(hiPS) cells. Effect of the size of embryoid body on cardionyocyte differentiation of hiPS cells. The Chemical Times. 2016;241:12-16.
Yu et al., Induced pluripotent stem cell lines derived from human somatic cells. Science. Dec. 21, 2007;318(5858):1917-20.
Zhang et al., LIN28 Regulates Stem Cell Metabolism and Conversion to Primed Pluripotency. Cell Stem Cell. Jul. 7, 2016;19(1):66-80.
Zhu et al., The Lin28/let-7 axis regulates glucose metabolism. Cell. Sep. 30, 2011;147(1):81-94.
Japanese Office Action for Application No. 2018-549142, dated Jan. 23, 2024, 16 pages.

\* cited by examiner

METHODS FOR THE RE-DERIVATION OF DIVERSE PLURIPOTENT STEM CELL-DERIVED BROWN FAT CELLS

RELATED APPLICATIONS

This Application is a Continuation of International Application No. PCT/US2016/065366, filed Dec. 7, 2016, which claims benefit of United States Provisional Application No. 62/264,311, filed Dec. 7, 2015. The entire contents of each of the aforementioned applications are hereby incorporated by reference.

FIELD OF THE INVENTION

The invention relates to the field of stem cell biology.

BACKGROUND OF THE INVENTION

Advances in stem cell technology, such as that associated with the isolation and propagation in vitro of primordial stem cells, including embryonic stem cells ("ES" cells including human ES cells ("hES" cells)) and related pluripotent or totipotent stem cells including but not limited to, iPS, EG, EC, ICM, epiblast, comparable cells derived from parthenogentically activated oocytes or ED cells (including said cells from the human species), constitute an important new area of medical research and therapeutic product development. While there are differences in the aforementioned pluripotent cell types, the present invention applies to the use of any of them capable of differentiating into diverse mesodermal cell types. Many of these primordial stem cells are naturally telomerase positive in the undifferentiated state, thereby allowing the cells to be expanded indefinitely and subsequently genetically modified and clonally expanded after said genetic modification prior to differentiation. Telomere length in many of the primordial cells lines is comparable to that observed in sperm DNA (approximately 10-18 kb TRF length) through in part the expression of the catalytic component of telomerase (TERT). Therefore, while differentiated progeny of the primordial stem cells are typically mortal due to the repression of TERT expression and telomere length shortens with cell doubling, their long initial telomere lengths provide the cells with a long replicative capacity compared to fetal or adult-derived cells and allows the manufacture of relatively young cells for transplantation.

Human ES cells have a demonstrated potential to be propagated in the undifferentiated state and then to be subsequently induced to differentiate into any and all of the cell types in the human body, including complex tissues. The pluripotency of hES cells has led to the suggestion that many diseases resulting from dysfunction of cells may be amenable to treatment by the administration of hES-derived cells of various differentiated types (Thomson et aL., *Science* 282:1145-1147 (1998)), and the long proliferative lifespan of hES-derived progenitor lines has allowed the clonal expansion and initial characterization of hES cell-derived embryonic progenitor cell lines (West et al, *Regen Med* (2008) 3(3), 287-308).

Pluripotent stem cells may also be derived from somatic cells through diverse reprogramming technologies. One such reprogramming technology is somatic cell nuclear transfer (SCNT). SCNT studies have demonstrated that it is possible to transform a somatic differentiated cell back to a primordial stem cell state such as that of embryonic stem ("ES") cells (Cibelli, et al., *Nature Biotech* 16:642-646 (1998)) or embryo-derived ("ED") cells. Alternatively, somatic cells may be reprogrammed to totipotency or pluripotency through analytical reprogramming technology (more commonly designated induced pluripotent stem (iPS) cell technology) wherein somatic cells are reprogrammed using transcriptional regulators (see PCT application Ser. No. PCT/US2006/030632 filed on Aug. 3, 2006 and titled "Improved Methods of Reprogramming Animal Somatic Cells") have been described. These methods offer potential strategies to transplant primordial-derived somatic cells with a nuclear genotype of the patient (Lanza et al., *Nature Medicine* 5:975-977 (1999)).

In addition to SCNT and analytical reprogramming technologies, other techniques exist to address the problem of transplant rejection, including the use of gynogenesis and androgenesis (see U.S. application nos. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US00/29551, filed Oct. 27, 2000). In the case of a type of gynogenesis designated parthenogenesis, pluripotent stem cells may be manufactured without antigens foreign to the gamete donor and therefore useful in manufacturing cells that can be transplanted without rejection into the gamete donor. In addition, parthenogenic stem cell lines can be assembled into a bank of cell lines homozygous in the HLA region (or corresponding MHC region of nonhuman animals) to reduce the complexity of a stem cell bank in regard to HLA haplotypes.

Totipotent or pluripotent cell lines or a bank of said cell lines such as those produced to be cGMP compliant can be produced that are selected or genetically-modified to escape immune surveillance. Various modalities are known in the art, including the isolation of said cells that are hemizygous in the region of the chromatin containing the HLA genes (or corresponding MHC region of nonhuman animals; see PCT application Ser. No. PCT/US2006/040985 filed Oct. 20, 2006 entitled "Totipotent, Nearly Totipotent or Pluripotent Mammalian Cells Homozygous or Hemizygous for One or More Histocompatibility Antigen Genes"). A bank of hemizygous cell lines provides the advantage of not only reducing the complexity inherent in the normal mammalian MHC gene pool simplifying the process of matching said antigens to patients, but it also reduces the gene dosage of the antigens to reduce the expression of said antigens without eliminating their expression entirely, thus avoiding stimulation of a natural killer response directed toward cells with no HLA class I expression.

In addition to reprogramming by SCNT or analytical reprogramming technologies such as iPS cell generation to obtain histocompatible cell grafts, the pluripotent stem cells may be genetically modified to reduce immunogenicity through the modulation of expression of certain genes such as the knockout of HLA genes, one of both alleles of beta 2 microglobulin (B2M), increased expression of HLA-G or HLA-H, or CTLA4-Ig and PD-L1 (Z. Rong, et al, An Effective Approach to Prevent Immune Rejection of Human ESC-Derived Allografts, *Cell Stem Cell,* 14: 121-130 (2014) incorporated herein by reference, as well as other modifications known in the art and subsequently used to generate differentiated cells for research and therapeutic applications. Such genetically-modified primordial stem cells designed to produce cells with reduced immunogenicity are designated "universal donor cells" herein.

The potential to isolate human pluripotent stem cell-derived clonal embryonic progenitor cell lines provides a means to propagate novel highly purified cell lineages with a prenatal pattern of gene expression including those with a pre-fetal pattern of gene expression such as those that lack the expression of COX7A1 useful for regenerating tissues. Such cell types have important applications in research, and for the manufacture of cell-based therapies (see PCT application Ser. No. PCT/US2006/013519 filed on Apr. 11, 2006 and entitled "Novel Uses of Cells With Prenatal Patterns of Gene Expression"; U.S. patent application Ser. No. 11/604,047 filed on Nov. 21, 2006 and entitled "Methods to Accelerate the Isolation of Novel Cell Strains from Pluripotent Stem Cells and Cells Obtained Thereby"; and U.S. patent application Ser. No. 12/504,630 filed on Jul. 16, 2009 and entitled "Methods to Accelerate the Isolation of Novel Cell Strains from Pluripotent Stem Cells and Cells Obtained Thereby"); U.S. patent application Ser. No. 14/048,910 entitled "Differentiated Progeny of Clonal Progenitor Cell Lines," incorporated herein by reference. Clonal, oligoclonal, and pooled populations of clonal and oligoclonal embryonic progenitors capable of forming embryonic cutaneous adipocyte progenitor cells (ECAPCs) expressing EYA4, wherein said progenitor cells are capable of differentiating into certain cellular components of brown adipose tissue (BAT) have also been disclosed (see WO2011/150105 entitled "Improved Methods of Screening Embryonic Progenitor Cell Lines,") as well as (U.S. patent application Ser. No. 13/683,241, entitled "Methods of Screening Embryonic Progenitor Cell Lines") as well as (US Patent Publication Serial No. 2015/0275177, entitled "Methods for Generating Pluripotent Stem Cell-Derived Brown Fat Cells") all of which are incorporated herein by reference.

Despite of the advances described above, there remains a need to improve methods for screening pluripotent stem cell-derived cells for potential of differentiation into desired cell types, including the cellular components of brown adipose tissue (BAT). Said BAT progenitors when transplanted in vivo have the potential to generate a therapeutic response in patients afflicted with symptoms of the metabolic syndrome, said symptoms including diabetes, coronary disease, obesity, dyslipidemia, hypertension, and complications of diabetes such as renal and retinal disease.

There also remains a need for means to effectively differentiate pluripotent stem cells into site-specific progenitor and terminally differentiated cell types including site-specific BAT cell types. Moreover, there is a growing need for improved methods for generating progenitor cell types from pluripotent stem cells that display and maintain a uniform differentiated state and exhibit site-specific differences in gene expression while expressing a prenatal or pre-fetal pattern of gene expression as evidenced by an absence of expression of COX7A1. Adult or fetal-derived adipocytes or adipocyte progenitors have reduced capacity for BAT or subcutaneous adipose tissue (SAT) regeneration, and express COX7A1. In contrast, BAT or SAT progenitors capable of robust tissue regeneration have a prefetal (i.e. prenatal) pattern of gene expression as evidenced by a lack of COX7A1 expression.

Adipocytes are an example of a cell type with important site-specific differences in gene expression, with diverse types of adipocytes within the human body each having unique roles in maintaining physiological homeostasis. While SAT cells in general provide a physiological function of storing energy for future metabolic needs, BAT cells regulate energy expenditure or thermogenesis and synthesize adipokines such as lipasin and adiponectin. BAT cells are progressively lost in the development and aging of humans, consequently their loss leads to an increasing age-dependent risk of disorders where BAT cells play a critical role (such as in regulating fat metabolism in the body, blood pressure, blood glucose regulation, pancreatic beta cell numbers in the pancreas, and HDL and LDL lipoprotein and triglyceride metabolism) in the populations with less BAT. Thus, a need exists for generating purified adipocyte progenitors capable of differentiating into site-specific adipocytes of diverse tissue types, including BAT cells.

Surprisingly, the methods of the present invention demonstrate that distinct pluripotent stem cell-derived clonal embryonic progenitor cell lines can be isolated which when cultured and expanded in the undifferentiated state do not express high levels of adipocyte markers until they are actively differentiated through the administration of the defined factors of the present invention and do not express detectable levels of markers of BAT adipocytes such as the gene UCP1 or the adipokine ADIPOQ, until differentiated, but nevertheless, when differentiated using the conditions disclosed herein, are capable of differentiating into either: 1) UCP1-expressing brown adipose tissue (BAT) cells that express low to undetectable adipokines such as C19orf80 (also known betatrophin or ANGPTL8, encoded in humans by the C19orf80 gene), and adiponectin (also known as AdipoQ or GBP-28, encoded in humans by the ADIPOQ gene) or 2) clonal embryonic progenitors capable of making adipocytes that express abundant mRNA for C19orf80 and adiponectin, but low levels of UCP1. In addition, surprisingly, clonal progenitor cell lines can be isolated and expanded in cell number using the methods of the present invention that have diverse site-specific markers and differ from one another in regard to mitochondrial function. For example, the methods of the present invention demonstrate that the pluripotent stem cell-derived clonal embryonic progenitor cell line ESI EP004 NP 88SM (also referred to as NP 88SM or NP88SM or NP88) which can be cultured and expanded in a relatively undifferentiated state that does not express pluripotency markers or express high levels of adipocyte markers and does not express detectable levels of markers of BAT adipocytes such as C19orf80, adiponectin or UCP1, nevertheless, when differentiated using the methods of the present invention, is capable of simultaneously expressing levels of UCP1, C19orf80, and ADIPOQ at levels comparable or higher to cultured fetal-tissue derived BAT cells but unlike the previously-disclosed clonal progenitor line NP110SM (also referred to as NP 110SM or NP110) (US Patent Application Publication No. 2015/0275177, entitled "Methods for Generating Pluripotent Stem Cell-Derived Brown Fat Cells," which is incorporated herein by reference), NP88SM does not express the site-specific marker HOXA5, and shows an increased oxygen consumption rate compared to the NP110SM cell line when differentiated into brown adipocytes.

There is a need for additional methods that permit the directed differentiation of pluripotent stem cells into particular progenitor cell types capable of making the cellular components of brown fat that can be effectively and reproducibly dosed in cell therapy regimens that result in the engraftment of viable and functional BAT cells useful in the treatment of the symptoms of adiposity, Type I and Type II diabetes, hypertension, and diseases associated with endothelial cell dysfunction including coronary disease syndromes where many of these disorders occur simultaneously in a patient (such as metabolic syndrome X and related disorders as described herein). Moreover, there is a need for progenitor cell types and terminally differentiated cell types produced from said progenitor cell types with expression of physiologically-beneficial genes including, but not limited to, uncoupling protein 1 (UCP1), angiopoietin like 8 (ANGPTL8 also known as C19orf80), adiponectin (ADIPOQ), and formulating said cells such that they may be stably engrafted subcutaneously and may deliver such adipokines and beneficial factors systemically to increase insulin sensitivity, decrease total body fat, decrease symptoms of Type I and Type II diabetes, favorably impact the course of coronary disease, and treat metabolic syndrome X. Lastly, there exists a need for a biocompatible matrix that facilitates the differentiation of embryonic progenitors into adipocytes, to promote the permanent engraftment of said cells in suitable sites in the body, and limit the undesired migration of said brown fat cellular components sites when injected in vivo. Various embodiments of the invention described infra meet these needs and other needs in the field.

SUMMARY

The present invention provides compounds, compositions, kits, reagents and methods useful for the differentiation and use of human embryonic progenitor cell types. The present invention incorporates by reference U.S. patent application Ser. No. 14/554,019 (published as No. 2015/0275177).

In one embodiment, the invention provides methods of generating novel pluripotent stem cell-derived cellular components of brown adipose tissue, compositions comprising the same, and methods of using the same. In further embodiments the invention provides isolated clonal progenitor cell lines that give rise to diverse clonally-purified site-specific types of brown adipose cells. The isolated clonal progenitor cell lines may give rise to brown adipose cells in vitro. The isolated clonal progenitor cell lines may also give rise to brown adipose cells in vivo.

In certain embodiments the invention provides an isolated pluripotent stem cell-derived clonal progenitor cell line capable of differentiating into a cellular component of BAT, wherein said differentiated cell, derived from a relatively undifferentiated progenitor cell, expresses one or more markers chosen from FABP4, C19orf80, ADIPQ, UCP1, PCK1, NNAT, THRSP, CEBPA, or CIDEA after being differentiated as described herein, but unlike fetal or adult-derived BAT cells, said pluripotent stem cell-derived clonal progenitor cell line does not express the gene COX7A1 when cultured and differentiated in vitro prior to in vivo administration. The isolated clonal progenitor cell line may give rise to brown adipose cells in vitro. The isolated clonal progenitor cell line may give rise to brown adipose cells in vivo.

In certain embodiments the invention provides an isolated pluripotent stem cell-derived clonal progenitor cell line capable of differentiating into a cellular component of brown adipose tissue (BAT), e.g, a brown adipocyte expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from DIO3, DLK1, ZIC2, SLC1A3 and SBSN but does not express COX7A1 and does not express one or more of HOXA5, IL13RA2, DLX5, CRABP1, NEFM, PRG4, and RBP1. The present invention also provides methods of making said pluripotent stem cell-derived clonal progenitor cell line similar in a pattern of gene expression to the isolated cell line NP88 SM.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, HOXB2, HOXA5, DLK1, NEFM, and RBP1 but does not express COX7A1 and does not express one or more of ZIC2, DLX5, PRG4, IL13RA2, CRABP1, and SBSN. The present invention also provides methods of making said pluripotent stem cell-derived clonal progenitor cell line similar in a pattern of gene expression to the isolated cell line NPCC SM19.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, RBP1, and ZIC2, but does not express COX7A1 and does not express one or more of HOXB2, HOXA5, NEFM, PRG4, DLX5, IL13RA2, CRABP1, and SBSN. The present invention also provides methods of making said pluripotent stem cell-derived clonal progenitor cell line similar in a pattern of gene expression to the isolated cell line NPCC SM36.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, HOXB2, DLX5, and ZIC2, but does not express COX7A1 and does not express one or more of HOXA5, NEFM, PRG4, and RBP1. The present invention also provides methods of making said pluripotent stem cell-derived clonal progenitor cell line similar in a pattern of gene expression to the isolated cell line NPCC SM28.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, DLK1, DLX5, PRG4, and ZIC2 but does not express COX7A1 and does not express one or more of HOXB2, HOXA5, GPC4, NEFM, IL13RA2, NTNG1 and SBSN. The present invention also provides methods of making said pluripotent stem cell-derived clonal progenitor cell line similar in a pattern of gene expression to the isolated cell line NPCC SM31.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from CRABP1, SNAP25, PPP1R1B, PRG4, DLK1, ZIC2 and PAPLN but does not express COX7A1 and does not express one or more of HOXA2, HOXB2, HOXA5, DLX5, RBP1, and IL13RA2. The present invention also provides methods of making said pluripotent stem cell-derived clonal progenitor cell lines similar in a pattern of gene expression to the isolated cell lines NP111 SM, NP77 EN, NPBO EN, and NP85 EN.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, ZIC2, THY1 and EFNB2 but does not express COX7A1 and does not express one or more of DLK1, PPP1R1B, and GPC4. The present invention also provides methods of making said pluripotent stem cell-derived clonal progenitor cell line similar in a pattern of gene expression to the isolated cell line NPCC SM23.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA2, ZIC2, CD24, and RBP1 but does not express COX7A1 and does not express one or more of DLK1, PPP1R1B, NEFM, and GPC4. The present invention also provides methods of making said pluripotent stem cell-derived clonal progenitor cell line similar in a pattern of gene expression to the isolated cell line NPCC SM27.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXA5, SNAP25, THY1, PAPLN, ZIC2, and DLK1 but does not express COX7A1 and does not express one or more of RBP1, NEFM, and DLX5. The present invention also provides methods of making said pluripotent stem cell-derived clonal progenitor cell line similar in a pattern of gene expression to the isolated cell line NP78 EN.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from HOXC6, PAPLN, THY1, RBP1 and EFNB2 but does not express COX7A1 and does not express one or more of HOXA5, ZIC2, and NEFM. The present invention also provides methods of making said pluripotent stem cell-derived clonal progenitor cell line similar in a pattern of gene expression to the isolated cell line SK1.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from DLK1, DLX5, GPC4, and THY1 but does not express COX7A1 and does not express one or more of HOXA2, HOXB2, HOXA5, and SNAP25. The present invention also provides methods of making said pluripotent stem cell-derived clonal progenitor cell line similar in a pattern of gene expression to the isolated cell line NP92 SM.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from BARX1, EPDR1, GPC4, EFNB2, and DLK1 but does not express COX7A1 and does not express one or more of HOXA2, HOXB2, HOXA5, ZIC2, CRABP1, and DLX5. The present invention also provides methods of making said pluripotent stem cell-derived clonal progenitor cell line similar in a pattern of gene expression to the isolated cell line NP91 SM.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from, SNAP25, PRG4, SBSN, GPC4, and DLK1 but does not express COX7A1 and does not express one or more of HOXA2, HOXA5, HOXB2, and CRABP1. The present invention also provides methods of making said pluripotent stem cell-derived clonal progenitor cell line similar in a pattern of gene expression to the isolated cell line NP93 SM.

In certain embodiments the invention provides an isolated pluripotent stem cell-derived clonal progenitor cell line capable of differentiating into a cellular component of BAT expressing UCP1, wherein said pluripotent stem cell-derived clonal progenitor cell line is isolated from pluripotent stem cells differentiated in the presence of noggin, expanded as a line of clonal embryonic progenitors where said progenitors prior to differentiation express one or more markers chosen from ALDH1A2, SBSN, CPVL, ZIC2, and THY1 but does not express COX7A1 and does not express one or more of HOXA2, HOXA5, HOXB2, RBP1 and CRABP1. The present invention also provides methods of making said pluripotent stem cell-derived clonal progenitor cell line similar in a pattern of gene expression to the isolated cell line NP113 SM.

In another embodiment the invention provides isolated pluripotent stem cell-derived clonal, or pooled clonal progenitor cell lines wherein said cell lines are isolated from pluripotent stem cells differentiated in the presence of an inactivator of the TGF-beta family of growth factors such as noggin, expanded as a line of clonal embryonic progenitors where said progenitors are capable of differentiating into purified populations of UCP1-expressing brown adipocyte cells.

In another embodiment the invention provides isolated pluripotent stem cell-derived clonal, or pooled clonal progenitor cell lines wherein said cell lines are isolated from pluripotent stem cells differentiated in the presence of media conducive to the growth of skeletal muscle myoblasts such as a MCDB 120 medium supplemented with EGF, Insulin, Dexamethasone, FCS or FBS, bFGF, bovine Fetuin (bovine, expanded as a line of clonal embryonic progenitors where said progenitors are capable of differentiating into purified populations of UCP1-expressing brown adipocyte cells.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from DIO3, DLK1, ZIC2, SLC1A3 and SBSN but does not express COX7A1 and does not express one or more of HOXA5, IL13RA2, DLX5, CRABP1, NEFM, PRG4, and RBP1. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, HOXB2, HOXA5, DLK1, NEFM, and RBP1 but does not express COX7A1 and does not express one or more of ZIC2, DLX5, PRG4, IL13RA2, CRABP1, and SBSN. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, RBP1, and ZIC2, but does not express COX7A1 and does not express one or more of HOXB2, HOXA5, NEFM, PRG4, DLX5, IL13RA2, CRABP1, and SBSN. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, HOXB2, DLX5, and ZIC2, but does not express COX7A1 and does not express one or more of HOXA5, NEFM, PRG4, and RBP1. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, DLK1, DLX5, PRG4, and ZIC2 but does not express COX7A1 and does not express one or more of HOXB2, HOXA5, GPC4, NEFM, IL13RA2, NTNG1 and SBSN. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from CRABP1, SNAP25, PPP1R1B, PRG4, DLK1, ZIC2 and PAPLN but does not express COX7A1 and does not express one or more of HOXA2, HOXB2, HOXA5, DLX5, RBP1, and IL13RA2. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, ZIC2, THY1 and EFNB2 but does not express COX7A1 and does not express one or more of DLK1, PPP1R1B, and GPC4. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, ZIC2, CD24, and RBP1 but does not express COX7A1 and does not express one or more of DLK1, PPP1R1B, NEFM, and GPC4. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA5, SNAP25, THY1, PAPLN, ZIC2, and DLK1 but does not express COX7A1 and does not express one or more of RBP1, NEFM, and DLX5. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXC6, PAPLN, THY1, RBP1 and EFNB2 but does not express COX7A1 and does not express one or more of HOXA5, ZIC2, and NEFM. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from DLK1, DLX5, GPC4, and THY1 but does not express COX7A1 and does not express one or more of HOXA2, HOXB2, HOXA5, and SNAP25. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from BARX1, EPDR1, GPC4, EFNB2, and DLK1 but does not express COX7A1 and does not express one or more of HOXA2, HOXB2, HOXA5, ZIC2, CRABP1, and DLX5. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from SNAP25, PRG4, SBSN, GPC4, and DLK1 but does not express COX7A1 and does not express one or more of HOXA2, HOXA5, HOXB2, and CRABP1. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from ALDH1A2, SBSN, CPVL, ZIC2, and THY1 but does not express COX7A1 and does not express one or more of HOXA2, HOXA5, HOXB2, RBP1 and CRABP1. Said isolated clonal progenitor cell line may give rise to brown adipose cells that secrete the protein encoded by the gene C19orf80 also designated angiopoietin like 8 (ANGPTL8) or lipasin or betatrophin in vitro. The isolated clonal progenitor cell line may give rise to brown adipose cells that secrete lipasin in vivo for therapeutic effect in patients with low circulating levels of lipasin or where the administration of lipasin is therapeutic such as diabetes, heart disease, dyslipidemia and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from DIO3, DLK1, ZIC2, SLC1A3 and SBSN but does not express COX7A1 and does not express one or more of HOXA5, IL13RA2, DLX5, CRABP1, NEFM, PRG4, and RBP1. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, HOXB2, HOXA5, DLK1, NEFM, and RBP1 but does not express COX7A1 and does not express one or more of ZIC2, DLX5, PRG4, IL13RA2, CRABP1, and SBSN. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, RBP1, and ZIC2, but does not express COX7A1 and does not express one or more of HOXB2, HOXA5, NEFM, PRG4, DLX5, IL13RA2, CRABP1, and SBSN. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, HOXB2, DLX5, and ZIC2, but does not express COX7A1 and does not express one or more of HOXA5, NEFM, PRG4, and RBP1. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, DLK1, DLX5, PRG4, and ZIC2 but does not express COX7A1 and does not express one or more of HOXB2, HOXA5, GPC4, NEFM, IL13RA2, NTNG1 and SBSN. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from CRABP1, SNAP25, PPP1R1B, PRG4, DLK1, ZIC2 and PAPLN but does not express COX7A1 and does not express one or more of HOXA2, HOXB2, HOXA5, DLX5, RBP1, and IL13RA2. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, ZIC2, THY1 and EFNB2 but does not express COX7A1 and does not express one or more of DLK1, PPP1R1B, and GPC4. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA2, ZIC2, CD24, and RBP1 but does not express COX7A1 and does not express one or more of DLK1, PPP1R1B, NEFM, and GPC4. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXA5, SNAP25, THY1, PAPLN, ZIC2, and DLK1 but does not express COX7A1 and does not express one or more of RBP1, NEFM, and DLX5. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from HOXC6, PAPLN, THY1, RBP1 and EFNB2 but does not express COX7A1 and does not express one or more of HOXA5, ZIC2, and NEFM. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from DLK1, DLX5, GPC4, and THY1 but does not express COX7A1 and does not express one or more of HOXA2, HOXB2, HOXA5, and SNAP25. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from BARX1, EPDR1, GPC4, EFNB2, and DLK1 but does not express COX7A1 and does not express one or more of HOXA2, HOXB2, HOXA5, ZIC2, CRABP1, and DLX5. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from SNAP25, PRG4, SBSN, GPC4, and DLK1 but does not express COX7A1 and does not express one or more of HOXA2, HOXA5, HOXB2, and CRABP1. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments the invention provides an isolated pluripotent stem cell-derived clonal progenitor cell line wherein said cell line is isolated from pluripotent stem cells differentiated in the presence of an inactivator of the TGF-beta family of growth factors such as noggin, expanded as a line of clonal embryonic progenitors where said progenitors prior to differentiation express one or more markers chosen from ALDH1A2, SBSN, CPVL, ZIC2, and THY1 but does not express COX7A1 and does not express one or more of HOXA2, HOXA5, HOXB2, RBP1 and CRABP1. Said isolated clonal progenitor cell line may give rise to brown adipose cells that secrete the protein encoded by the gene ADIPOQ designated adiponectin in vitro. The isolated clonal progenitor cell line may give rise to brown adipose cells that secrete adiponectin in vivo for therapeutic effect in patients with hypoadiponectinemia or where the administration of adiponectin is therapeutic such as diabetes, heart disease, dyslipidemia, osteoporosis, Alzheimer's disease, and metabolic syndrome.

In other embodiments, the invention provides methods of maximizing the expression of desired genes in said brown fat cells, compositions regarding the same and methods of using the same.

In still other embodiments the invention provides a method of differentiation of isolated pluripotent stem cell-derived clonal embryonic progenitor cell lines into UCP1-expressing cells comprising the steps of: 1) partially differentiating said pluripotent stem cells in the presence of an inactivator of the TGF-beta family of growth factors such as noggin; 2) Clonally isolating and propagating embryonic progenitor cell lines in vitro; 3) Exposing said clonal or pooled clones of embryonic progenitors to a PPARy agonist including but not limited to a small molecule in the thiazolidinedione class such as rosiglitazone, optionally in addition with one or more of the following: a hydrogel such as that containing Type I collagen and hyaluronic acid, triiodothyronine (T3), a β3-adrenoceptor agonist such as CL-316,243, and BMP4 or BMP7; 4) measuring the expression of UCP1 to detect lines capable of expressing a desired site-specific type of brown adipocytes.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from DIO3, DLK1, ZIC2, SLC1A3 and SBSN but does not express COX7A1 and does not express one or more of HOXA5, IL13RA2, DLX5, CRABP1, NEFM, PRG4, and RBP1; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, HOXB2, HOXA5, DLK1, NEFM, and RBP1 but does not express COX7A1 and does not express one or more of ZIC2, DLX5, PRG4, IL13RA2, CRABP1, and SBSN; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, RBP1, and ZIC2, but does not express COX7A1 and does not express one or more of HOXB2, HOXA5, NEFM, PRG4, DLX5, IL13RA2, CRABP1, and SBSN; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, HOXB2, DLX5, and ZIC2, but does not express COX7A1 and does not express one or more of HOXA5, NEFM, PRG4, and RBP1; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, DLK1, DLX5, PRG4, and ZIC2 but does not express COX7A1 and does not express one or more of HOXB2, HOXA5, GPC4, NEFM, IL13RA2, NTNG1 and SBSN; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from CRABP1, SNAP25, PPP1R1B, PRG4, DLK1, ZIC2 and PAPLN but does not express COX7A1 and does not express one or more of HOXA2, HOXB2, HOXA5, DLX5, RBP1, and IL13RA2; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, ZIC2, THY1 and EFNB2 but does not express COX7A1 and does not express one or more of DLK1, PPP1R1B, and GPC4; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA2, ZIC2, CD24, and RBP1 but does not express COX7A1 and does not express one or more of DLK1, PPP1R1B, NEFM, and GPC4; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXA5, SNAP25, THY1, PAPLN, ZIC2, and DLK1 but does not express COX7A1 and does not express one or more of RBP1, NEFM, and DLX5; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from HOXC6, PAPLN, THY1, RBP1 and EFNB2 but does not express COX7A1 and does not express one or more of HOXA5, ZIC2, and NEFM; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from DLK1, DLX5, GPC4, and THY1 but does not express COX7A1 and does not express one or more of HOXA2, HOXB2, HOXA5, and SNAP25; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from BARX1, EPDR1, GPC4, EFNB2, and DLK1 but does not express COX7A1 and does not express one or more of HOXA2, HOXB2, HOXA5, ZIC2, CRABP1, and DLX5; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from SNAP25, PRG4, SBSN, GPC4, and DLK1 but does not express COX7A1 and does not express one or more of HOXA2, HOXA5, HOXB2, and CRABP1; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

In other embodiments the invention provides a method for treating obesity, diabetes, hypertension, coronary disease, or Alzheimer's disease, and metabolic syndrome comprised of the following steps: 1) isolating a pluripotent stem cell-derived clonal progenitor cell line wherein said cell line is isolated from pluripotent stem cells; 2) differentiated in the presence of an inactivator of the TGF-beta family of growth factors such as noggin, expanded as a line of clonal embryonic progenitors where said progenitors prior to differentiation express one or more markers chosen from ALDH1A2, SBSN, CPVL, ZIC2, and THY1 but does not express COX7A1 and does not express one or more of HOXA2, HOXA5, HOXB2, RBP1 and CRABP1; and 3) Administering said progenitor cells or UCP1-expressing cells differentiated in the presence of a PPARy agonist including but not limited to a small molecule in the thiazolidinedione class such as rosiglitazone to the patient in combination with a hydrogel such as one comprised of thiolated hyaluronate, thiolated gelatin and/or both thiolated hyaluronate and thiolated gelatin with a crosslinker.

The clonal or pooled clonal embryonic progenitor cells of the present invention unlike fetal or adult-derived BAT progenitors do not express COX7A1 or ADIRF. The clonal progenitor cell lines may be grown on or encased in a hydrogel, e.g. a hydrogel such as one comprised of thiolated hyaluronate, thiolated gelatin and/or both thiolated hyaluronate and thiolated gelatin with a crosslinker.

In further embodiments the invention provides a method of obtaining a cell expressing UCP1 comprising contacting a clonal progenitor cell line with a PPARy agonist including but not limited to a small molecule in the thiazolidinedione class such as rosiglitazone, optionally in addition with one or more of the following: a hydrogel such as that containing Type I collagen and hyaluronic acid, triiodothyronine (T3), a β3-adrenoceptor agonist such as CL-316,243, and BMP4 or BMP7, thereby obtaining a cell expressing UCP1. Suitable TGFβ family members include members of the BMP family, such as BMP4, BMP6 or BMP7. In some embodiments the TGFβ family member may be TGFβ. The clonal progenitor cell line may be grown on or encased in a hydrogel, e.g. a hydrogel comprising thiolated hyaluronate, thiolated gelatin and/or both thiolated hyaluronate and thiolated gelatin.

In further embodiments the invention provides a method of obtaining a cell expressing C19orf80 comprising contacting a clonal progenitor cell line with one or more TGFβ family members thereby obtaining a cell expressing C19orf80. Suitable TGFβ family members include members of the BMP family, such as BMP4, BMP6, or BMP7. The clonal progenitor cell line may be grown on or encased in a hydrogel, e.g. a hydrogel comprising thiolated hyaluronate, thiolated gelatin and/or both thiolated hyaluronate and thiolated gelatin.

In still other embodiments the invention provides a method of obtaining a cell expressing one or more gene expression markers chosen from FABP4, C19orf80, ADIPOQ, or UCP1, comprising contacting a clonal progenitor cell line disclosed herein with a thiolated hyaluronate and thiolated gelatin-based hydrogel supplemented with 100 ng/ml BMP7, and 1.0 µM Rosiglitazone for 14 days wherein the cells are incubated for a period of time at lower than physiological temperature such as 28C.

In still other embodiments the invention provides a method of obtaining a cell expressing one or more gene expression markers chosen from FABP4, C19orf80, ADIPOQ, or UCP1, comprising contacting a clonal progenitor cell line disclosed herein with a thiolated hyaluronate and thiolated gelatin-based hydrogel supplemented with 10 ng/ml BMP4, 1.0 µM rosiglitazone, 2.0 nM triiodothyronine (T3), and for the last 4 hours prior to use, 10 µM CL316243.

In yet other embodiments the invention provides a method of obtaining a cell expressing one or more gene expression markers chosen from FABP4, C19orf80, ADIPOQ, or UCP1, comprising contacting a clonal progenitor cell line disclosed herein with a thiolated hyaluronate and thiolated gelatin-based hydrogel supplemented with 100 ng/ml BMP7, and 5.0 µM Rosiglitazone for 14 days wherein the cells are incubated at a physiological temperature.

In yet other embodiments the invention provides a method of obtaining a cell expressing one or more gene expression markers chosen from FABP4, C19orf80, ADIPOQ, or UCP1, comprising contacting a clonal progenitor cell line disclosed herein with a thiolated hyaluronate and thiolated gelatin-based hydrogel supplemented with 1-50 ng/ml BMP4, and 1.0-5.0 µM Rosiglitazone for 14 days wherein the cells are incubated at a physiological temperature.

In yet other embodiments the invention provides a method of obtaining a cell expressing one or more gene expression markers chosen from FABP4, C19orf80, ADIPOQ, or UCP1, comprising contacting a clonal progenitor cell line disclosed herein with a thiolated hyaluronate and thiolated gelatin-based hydrogel supplemented with 100 ng/ml BMP7, and 1.0-5.0 µM Rosiglitazone for 14 days wherein the cells are incubated for a final four hours in the presence of an added β3-specific adrenoceptor agonist (10 µM CL-316243).

In other embodiments the invention provides a method of treating metabolic and vascular disease in a subject comprising administering to the subject one or more of the cells described infra. The metabolic or vascular disease may include Type I or Type II diabetes, syndrome X, obesity, hypertension, and atherosclerosis. The cells may be administered to the subject in a formulation comprised of cells in suspension in a physiologically-compatible salt solution or preferably in a matrix, most preferably a collagen and hyaluronic acid-based hydrogel as described infra.

Still other embodiments of the invention include kits and reagents comprising cells described herein and reagents useful for obtaining and/or growing the cells described herein.

DEFINITIONS AND ABBREVIATIONS

Definitions

Figure 1:
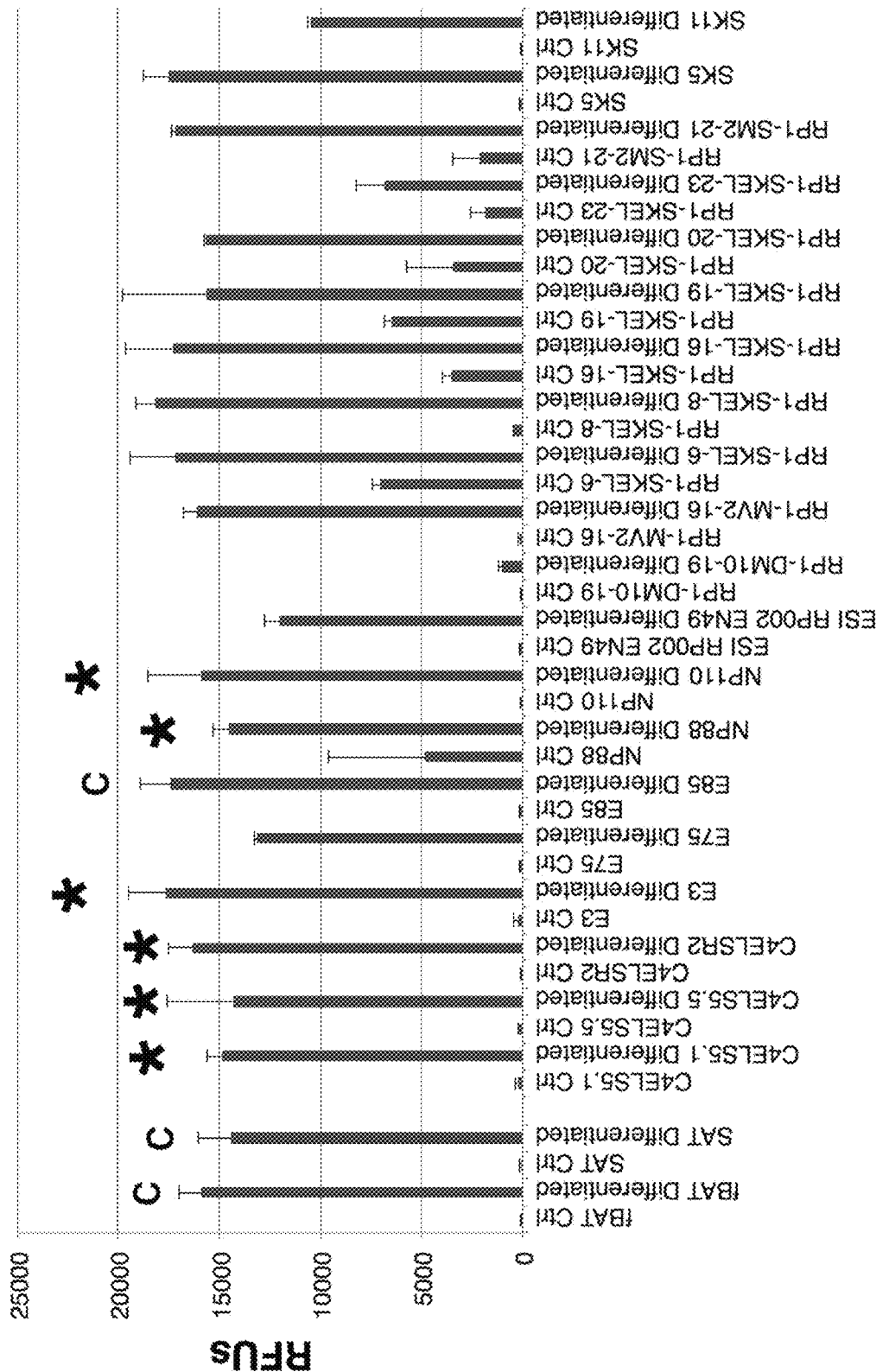
FIG. 1 shows a graph showing Illumina microarray RFU values for the expression of FABP4 in selected cells in the progenitor state (Ctrl) samples and those exposed to differentiation in BMP4, Rosiglitazone, T3, and CL-CL-316243 (Differentiated). (RFU values>130RFU being considered positive) ("*" Identifies CITED1 positive definitive adipocytes).

The term "adipose-derived SVF" refers to stromal vascular fraction cells from adipose tissue sources. Generally, these are liposuction material that is centrifuged to separate a pellet of cellular material (SVF) from less dense adipocytes. The adipose-derived SVF may also refer to such pelleted or otherwise liposuction-derived cells that are resuspended in liquid to be used in combination with the cells of the present invention as described herein.

The term "adult stem cells" refers to stem cells obtained from tissue originating from a mammal in stages of development after embryonic development is complete (in humans, this would refer to tissues of greater than eight weeks of gestational development). The tissue derived from the mammal may include tissue derived from a fetal or from an adult mammal and may include mesenchymal stem cells, neuronal stem cells, and bone marrow-derived stem cells.

The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte (see U.S. application nos. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006).

The term "blastomere/morula cells" refers to blastomere or morula cells in a mammalian embryo, a mammalian in vitro fertilized egg, or blastomere or morula cells cultured in vitro with or without additional cells including differentiated derivatives of those cells. For purposes of this disclosure, unless otherwise specified, the term "brown adipose cell" or "brown adipocyte" or "cellular component of brown adipose tissue (BAT)" refers to any cell that expresses adipocyte markers in conjunction with one or more of the genes UCP1, ADIPOQ or C19orf80 (also known as ANGPTL8 or LOC55908 [accession number NM_018687.3, identified on Illumina gene expression microarrays as probe ID 1430689], encoding for the protein LIPASIN, (also known as BETA-TROPHIN). The term includes mature cells present in fetal or adult brown adipose tissue that express COX7A1, while the cells of the present invention do not express the mature marker COX7A1 but otherwise are functional brown adipose cells and are desirable for therapeutic use compared to fetal or adult-derived brown adipose cells due to a higher level of expression of neurite outgrowth promoting factors such as Netrin G1 expression (promoting innervation of the tissue by the sympathetic nervous system) in the BAT cells produced from embryonic progenitor cells. The term also includes cells that are partially differentiated into brown adipocytes that express highest levels of Netrin G1 to promote said innervation.

The term "candidate culture" refers to a pluripotent stem cell-derived heterogeneous mixture of diverse embryonic progenitor cell types from which clonal, oligoclonal, or pooled clonal cells can be isolated and propagated as described (Regen. Med. (2008) 3(3), 287-308). Said candidate culture may, at the election of the user, be cryopreserved for the continuous re-isolation of new clonal, oligoclonal, or pooled clonal cells.

The term "cell expressing gene X", "gene X is expressed in a cell" (or cell population), or equivalents thereof, means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "clonal" refers to a population of cells obtained the expansion of a single cell into a population of cells all derived from that original single cells and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "differentiated cells" when used in reference to cells made by methods of this invention from pluripotent stem cells refer to cells having reduced potential to differentiate all somatic cell types when compared to the parent pluripotent stem cells. By way of non-limiting example, human pluripotent stem cells such as hES cells are less differentiated than the hES-derived clonal embryonic progenitor cells of the present invention, which in turn are less differentiated than the in vitro produced brown fat progenitors of the present invention, which are less differentiated than fetal or adult-derived brown fat cells in that fetal or adult-derived brown fat cells that express COX7A1, a marker of cells in fetal or later stages of differentiation, and wherein the cells of the present invention do not yet express COX7A1. The differentiated cells of this invention comprise cells that may differentiate further (i.e., they may not be terminally differentiated).

The term "direct differentiation" refers to process of differentiating: blastomere cells, morula cells, ICM cells, ED cells, or somatic cells reprogrammed to an undifferentiated state (such as in the process of making iPS cells but before such cells have been purified in an undifferentiated state) directly without the intermediate state of propagating isolated undifferentiated stem cells such as hES cells as undifferentiated cell lines. A nonlimiting example of direct differentiation would be the culture of an intact human blastocyst into culture and the derivation of ED cells without the generation of a human ES cell line as was described (Bongos, et al, 1994. *Human Reproduction* 9:2110).

The term "embryoid bodies" is a term of art synonymous with "aggregate bodies", referring to aggregates of differentiated and undifferentiated cells that appear when pluripotent stem cells overgrow in monolayer cultures, or are maintained in suspension cultures. Embryoid bodies are a mixture of different cell types, typically from several germ layers, distinguishable by morphological criteria and cell markers detectable by immunocytochemistry. The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The blastocysts, blastomeres, morulae and the like may be obtained from an in vitro fertilized egg. The ES cells may be derived from the in vitro fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, have a more flattened appearance in culture and typically do not contribute to germ line differentiation, and are therefore called "ES-like cells." It is commonly believed that human ES cells are in reality "ES-like", however, in this application we will use the term ES cells to refer to both ES and ES-like cell lines.

"Feeder cells" or "feeders" are terms used to describe cells of one type that are cocultured with cells of another type, to provide an environment in which the cells of the second type can grow. Certain types of pluripotent stem cells can be supported by primary mouse embryonic fibroblasts, immortalized mouse embryonic fibroblasts, embryonic avian fibroblasts, or human fibroblast-like cells differentiated from hES cell. Pluripotent stem cell populations are said to be "essentially free" of feeder cells if the cells have been grown through at least one round after splitting in which fresh feeder cells are not added to support the growth of the cells.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and U.S. Pat. No. 5,843,780 to Thomson). The hED cells may be derived from preimplantation embryos produced by the in vitro fertilization of an egg cell with sperm or DNA, nuclear transfer, or chromatin transfer, an egg cell induced to form a parthenote through parthenogenesis, or analytical reprogramming technology.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application nos. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000).

The term "human embryonic stem cells" (hES cells) refers to human ES cells which are lines of pluripotent stem cells generated from preimplantation human embryos, such as those discarded in the routine production of blastocysts in IVF procedures.

The term "human iPS cells" refers to cells with properties similar to hES cells, including the ability to form at least one cell type from all three germ layers (mesoderm, ectoderm and endoderm) when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. Application Ser. No. 09/736,268 filed on Dec. 15, 2000; U.S. application Ser. No. 10/831,599, filed Apr. 23, 2004; and U.S. Patent Publication 20020142397 (App. Ser. No. 10/015,824, entitled "Methods for Altering Cell Fate"); U.S. Patent Publication 20050014258 (App. Ser. No. 10/910,156, entitled "Methods for Altering Cell Fate"); U.S. Patent Publication 20030046722 (App. Ser. No. 10/032,191, entitled "Methods for cloning mammals using reprogrammed donor chromatin or donor cells"); and U.S. Patent Publication 20060212952 (App. Ser. No. 11/439,788, entitled "Methods for cloning mammals using reprogrammed donor chromatin or donor cells").

It will be appreciated that embryonic stem cells (such as hES cells), embryonic stem-cell like cells (such as iPS cells) and other pluripotent stem cells as well as progenitor cells derived from the cell types described infra may all be used according to the methods of the invention. The term "ICM cells" refers to the cells of the inner cell mass of a mammalian embryo or the cells of the inner cell mass cultured in vitro with or without the surrounding trophectodermal cells. The ICM cells may be derived from an in vitro fertilized egg.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "pluripotent stem cells" refers to mammalian cells capable of differentiating into more than one differentiated cell type of any of the three primary germ layers endoderm, mesoderm, and ectoderm including neural crest. Such cells include hES cells, blastomere/morula cells and their derived hED cells, hiPS cells, hEG cells, hEC cells. Pluripotent stem cells may be genetically modified or not genetically modified. By way on nonlimiting example, genetically modified cells may include markers such as fluorescent proteins to facilitate their identification when mixed with other cell types, or modifications of genes relating to immune surveillance to allow the cells to be tolerated allogeneically without rejection.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" which in this invention is used synonymously with "pluripotent stem cells" refers collectively to cells capable of differentiating into cells of all three primary germ layers: endoderm, mesoderm, and ectoderm, as well as neural crest. Human primordial stem cells therefore express stage-specific embryonic antigens (SSEA) SSEA3 and SSEA4, and markers detectable using antibodies designated Tra-1-60 and Tra-1-81. (Thomson et al., Science 282:1145, 1998) Therefore, examples of primordial stem cells would include but not be limited by human or non-human mammalian ES cells or cell lines, blastomere/morula cells and their derived ED cells, iPS, and EG cells, or the corresponding cells derived from parthenogenetic, gynogenetic, or nuclear transfer-derived embryos.

The term "universal donor cells" refers to cells derived from primordial stem cells that have been genetically modified to reduce immunogenicity through the modulation of expression of certain genes such as the knockout of one of both alleles of beta 2 microglobulin (B2M), knockout of HAL genes, or increased expression of HLA-G or HLA-H, or CTLA4-Ig and PD-L1, as well as other modifications enclosed herein or known in the art and subsequently used to generate differentiated cells for research and therapeutic applications wherein said cells have reduced immunogenicity "Subject" as used herein includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term "subject," "patient" or "animal" refers to a male. In some embodiments, the term "subject," "patient" or "animal" refers to a female.

The terms "treat," "treated," or "treating" as used herein can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "tissue regeneration" refers to at least partial regeneration, replacement, restoration, or regrowth of a tissue, organ, or other body structure, or portion thereof, following loss, damage, or degeneration, where said tissue regeneration but for the methods described in the present invention would not take place. Examples of tissue regeneration include the regrowth of severed digits or limbs including the regrowth of cartilage, bone, muscle, tendons, and ligaments, the scarless regrowth of bone, cartilage, skin, or muscle that has been lost due to injury or disease, with an increase in size and cell number of an injured or diseased organ such that the tissue or organ approximates the normal size of the tissue or organ or its size prior to injury or disease. Depending on the tissue type, tissue regeneration can occur via a variety of different mechanisms such as, for example, the rearrangement of pre-existing cells and/or tissue (e.g., through cell migration), the division of adult somatic stem cells or other progenitor cells and differentiation of at least some of their descendants, and/or the dedifferentiation, transdifferentiation, and/or proliferation of cells.

"Adiponectin" or "ADIPOQ", also known as AdipoQ, GBP-28, or apM1, is a protein that in humans is encoded by the ADIPOQ gene. Adiponectin modulates a number of metabolic processes, including glucose regulation and fatty acid oxidation. Adiponectin is secreted from adipose tissue into the bloodstream, where levels of the hormone are inversely correlated with body fat percentage, type II diabetes, and coronary disease. (Yamamoto et al, "Circulating adiponectin levels and risk of type 2 diabetes in the Japanese", *Nutr Diabetes*. 2014 Aug. 18; 4: e130).

"FABP4 (fatty acid binding protein 4)", also known as aP2 or AFABP, is a carrier protein for fatty acids that is primarily expressed in adipocytes and macrophages and encoded by the FABP4 gene in humans. Fatty acid binding proteins are a family of small, highly conserved, cytoplasmic proteins that bind long-chain fatty acids and other hydrophobic ligands. It is thought that FABPs roles include fatty acid uptake, transport, and metabolism. (Thumser et al, "Fatty acid binding proteins: tissue-specific functions in health and disease", *Curr Opin Clin Nutr Metab Care*. 2014 March; 17(2):124-9).

"Lipasin", also known as betatrophin or ANGPTL8, is a protein that in humans is encoded by the C19orf80 gene also known as LOC55908, LIPASIN, or BETATROPHIN (accession number NM_018687.3, identified on Illumina gene expression microarrays as probe ID 1430689). C19orf80 is a putative peptide hormone that was found to increase the rate at which pancreatic beta cells undergo cell division in mice (Yi et al, Betatrophin: a hormone that controls pancreatic beta cell proliferation, *Cell*. 2013 May 9; 153(4): 747-58). Injection of mice with betatrophin cDNA resulted in lowered blood sugar levels, presumably due to action at the pancreatic islet cells. (Yi et al, Betatrophin: a hormone that controls pancreatic β cell proliferation, *Cell*. 2013 May 9; 153(4): 747-58).

"UCP1 (uncoupling protein 1)", also known as thermogenin or SLC25A7, is an uncoupling protein found in the mitochondria of brown adipose tissue and encoded by the UCP1 gene in humans. UCP1 is involved in heat generation heat by non-shivering thermogenesis (Golozoubova et al, Only UCP1 can mediate adaptive nonshivering thermogenesis in the cold, *FASEB J.* 2001, September 15 (11): 2048-50). UCP-1 uncouples oxidative phosphorylation from electron transport, yielding heat instead of ATP, as occurs in mitochondria without UCP-1 (Fedorenko, et al, "Mechanism of fatty-acid dependent UCP1 uncoupling in brown fat mitochondria" *Cell* 2012 October 12; 151(2) 400-13). UCP1 is activated in brown fat cells by a signaling cascade initiated by release of norepinephrine by the sympathetic nervous system onto the Beta-3 adrenergic receptor on the plasma membrane (Cannon et al, "Brown adipose tissue function and physiological significance" *Physiol Rev.*2004, 84, 277-359).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

ABBREVIATIONS

BAT—Brown Adipose Tissue
bFGF—basic Fibroblast Growth Factor
BMP—Bone Morphogenetic Protein
cGMP—Current Good Manufacturing Processes
CNS—Central Nervous System
CT—Computed Tomography
CTLA4-Ig—Cytotoxic T lymphocyte antigen 4-immunoglobulin fusion protein
DMEM—Dulbecco's modified Eagle's medium
DMSO—Dimethyl sulphoxide
DPBS—Dulbecco's Phosphate Buffered Saline
EC—Embryonal carcinoma
EC Cells—Embryonal carcinoma cells; hEC cells are human embryonal carcinoma cells ECAPCs—Embryonic Cutaneous Adipocyte Progenitor Cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells
EGF—Epidermal Growth Factor
ES Cells—Embryonic stem cells; hES cells are human ES cells. ES cells, including hES cells for the purposes of this invention may be in a naïve state corresponding to ICM cells of the human blastocyst, or the primed state corresponding to flattened epiblast cells (sometimes referred to as "ES-like" cells).
FACS—Fluorescence activated cell sorting
fBAT—fetal-derived brown adipose tissue
FBS—Fetal bovine serum
FCS—Fetal Calf Serum
FDG—F18-fluorodeoxyglucose
GMP—Good Manufacturing Practices
hED Cells—Human embryo-derived cells
hEG Cells—Human embryonic germ cells are stem cells derived from the primordial germ cells of fetal tissue.
hEP Cells—Human embryonic progenitor cells hiPS Cells—Human induced pluripotent stem cells are cells with properties similar to hES cells obtained from somatic cells after exposure to hES-specific transcription factors such as SOX2, KLF4, OCT4, MYC, or the genes, RNAs, or proteins encoded by NANOG, LIN28, OCT4, and SOX2.
hES—human Embryonic Stem
hESC—human Embryonic Stem Cells
ICM—Inner cell mass of the mammalian blastocyst-stage embryo.
iPS Cells—Induced pluripotent stem cells are cells with properties similar to hES cells obtained from somatic cells after exposure to ES-specific transcription factors such as SOX2, KLF4, OCT4, MYC, or NANOG, LIN28, OCT4, and SOX2.
ITS—Insulin, transferrin, selenium
IVF—In vitro fertilization
MEM—Minimal essential medium
MSCs—Mesenchymal Stem Cells
NHACs—Normal human articular chondrocytes
NT—Nuclear Transfer
PBS—Phosphate buffered saline
PCR—Polymerase Chain Reaction
PD-L1—Programmed death ligand-1
PEGDA—Polyethylene glycol diacrylate
PET—Positron Emission Tomography
PNS—Peripheral Nervous System
qRT-PCR—quantitative real-time polymerase chain reaction
RFU—Relative Fluorescence Units
SCNT—Somatic Cell Nuclear Transfer
SFM—Serum-Free Medium
SVF—Stromal Vascular Fraction
TRF—Terminal Restriction Fragment; products of the digestion of telomeres following digestion with restriction endonucleases
WAT cells—White adipose tissue cells

DETAILED DESCRIPTION

This invention solves the problem of generating large populations of highly purified cellular components of human brown adipose tissue by showing how to efficiently differentiate them from pluripotent stem cells.

Pluripotent stem (pPS) cells such as human induced pluripotent stem cells (hiPS) cells, human embryonic stem (hES) cells, and human parthenogenetic pluripotent stem cells (hPPS) cells and other cells with the potential of pluripotency, can be differentiated into normal functional cellular components of BAT on an industrial scale by first initiating general differentiation under certain defined conditions described herein, and then expanding clonal embryonic progenitor cells or pooled clonal embryonic progenitor cells, or oligoclonal embryonic progenitor cells that can simply be expanded in cell culture as adherent cells in traditional cell culture vessels or attached to beads in a slurry, cryopreserved, and expanded again, and then differentiated using the techniques described herein to generate cellular components of BAT useful for research and therapy. A strategy has been developed that helps optimize the combination of factors that are useful in the above-mentioned manufacturing technology. The techniques of this invention are oriented at producing a population of highly-enriched cells capable of differentiating into ADIPOQ, C19orf80, and UCP1-expressing BAT cells.

The development of methods to efficiently produce BAT cells from hES cells is important, because hES cells can be caused to proliferate indefinitely and can be genetically modified to allow the introduction of genetic modifications that allow the generation of off-the-shelf allogeneic cells that can then yield industrial scale manufacture of the desired therapeutically-useful differentiated cell type providing a means is known to manufacture said differentiated cell type with requisite standards of purity and identity. Accordingly, this invention provides a system that can be used to generate unbounded quantities of BAT cells.

The disclosure that follows provides a full description of how to make the BAT cells of this invention. It provides extensive illustrations of how these cells can be used in research and pharmaceutical development. The disclosure also provides pharmaceutical compositions, devices, and treatment methods for the use of pluripotent stem cell-derived BAT cells for regeneration and remodeling of BAT to restore youthful fat, lipoprotein, and glucose metabolism.

There is a growing need for improved methods of generating progenitor cell types from ES and iPS cells that display and maintain a uniform differentiated state, and exhibit site-specific homeobox gene expression. Adipocytes are an example of cell types with important site-specific differences in gene expression. The diverse types of adipocytes within the developed human body each have unique roles in maintaining physiological homeostasis. For example, subcutaneous fat differs in numerous aspects from visceral fat. In the case of subcutaneous fat, there are varieties of site-specific adipocytes that also differ from one another. While adipocytes in general provide a physiological function in storing energy for future metabolic needs, a specialized type of adipose tissue called brown adipose tissue (BAT) or simply "brown fat", commonly restricted to the dorsal aspect of mammals such as between the scapulae in young mammals, or in the superclaviclar or cervical or region, differs in several respects from the white adipocytes in subcutaneous fat elsewhere in the body. Metabolically active BAT has been reported to be detectable in adult humans as assayed by PET/CT using as an imaging agent the glucose analog F18-fluorodeoxyglucose (FDG-PET/CT) (van der Lans et al, "Cold-activated brown adipose tissue in human adults: methodological issues" Am J Physiol Regul Integr Comp Physiol, 2014, July 15; 307 (2) R103-13)).

In the last 20 years, BAT has been discovered to function as a thermogenic as well as an organ that regulates energy, lipid, and lipoprotein metabolism. Brown fat cells are highly innervated by the sympathetic nervous system (SNS) and BAT thermogenesis is almost exclusively under SNS innervation control (Cannon et al, "Brown adipose tissue function and physiological significance" Physiol Rev.2004, 84, 277-359). BAT can further function as an endocrine organ generating critical adipokines such as adiponectin (also known as AdipoQ, GBP-28 or aPM1, encoded in humans by the ADIPOQ gene,), and C19orf80 (also known betatrophin or ANGPTL8, encoded in humans by the C19orf80 gene) (Shehzad, et al, "Adiponectin:regulation of its production and its role in human diseases" *Hormone*, 2012, January-March, 11(1): 8-20). It appears that the mitochondrial membrane protein UCP1 (uncoupling protein 1, also known as thermogenin, encoded in humans by the gene UCP1), expressed in certain cells resident in brown fat, is critical in the uncoupling of oxidative phosphorylation leading to thermogenesis by BAT (Fedorenko, et al, "Mechanism of fatty-acid dependent UCP1 uncoupling in brown fat mitochondria" *Cell* 2012 October 12; 151 (2) 400-13). Furthermore, there are two distinct types of brown fat cells, commonly designated as "brown" fat cells and "beige" fat cells. Brown and beige fat cells are reported to have different embryological origins wherein the brown fat cells are reported to be derived from MYF5+ progenitors also capable of skeletal muscle differentiation (Seale P, Bjork B, Yang W, et al., PRDM16 controls a brown fat/skeletal muscle switch. *Nature* (2008); 454:961-968), and beige fat cells are reported to be derived from MYF5-progenitors (Wu et al, "Beige adipocytes are a distinct type of thermogenic fat cell in mouse and human" Cell, Jul. 20, 2012, 150(2) 366-376).

As used in the present invention, all cells of the present invention expressing UCP1 and one or more of ADIPOQ or C19orf80 are designated as "brown" fat cells. While small molecule drugs such as the thiazolidinedione class of compounds (rosiglitazone, also known as Avandia) have shown usefulness as antidiabetic agents, such compounds can often have serious side effects. Therefore, the concept of brown fat cell transplantation as a therapeutic regimen has emerged. Reports suggest that the loss of brown or beige fat cells may correlate with obesity, cardiovascular disease, hypertension, and type II diabetes and restoration of these cells by transplantation can reverse obesity and type II diabetes in non-human animal studies. There remains, however, a need for a method for the manufacture brown fat cellular components that express UCP1 and certain adipokines expressed by brown fat tissue such as adiponectin and C19orf80 on an industrial scale suitable for transplantation in humans for the treatment of these large and growing health problems.

Techniques such as the clonal propagation of human embryonic progenitor (hEP) cell lines may facilitate the derivation of purified and scalable cell lines corresponding to regional anlagen of diverse tissue types for use in research and therapy. In addition, the standardization of research around such defined and scalable progenitors may improve the reproducibility of differentiation studies from laboratory-to-laboratory.

The present invention teaches methods and compositions for the manufacture of specific cellular components of BAT tissue, including: 1) UCP1-expressing brown adipocytes that express low to undetectable levels of the adipokines adiponectin and betatrophin; 2) adiponectin+, betatrophin+ adipocytes that express low or no levels of UCP1; 3) UCP1-expressing brown adipocytes that express ADIPOQ and C19orf80 at levels comparable to fBAT cells, and 4) vascular endothelial cells expressing ITLN1 or ITLN2; and combinations of these three cell types with collagen and hyaluronic acid-based hydrogels with or without added cells from autologous adipose-derived SVF.

Sources of Stem Cells

This invention can be practiced using stem cells of various types. Amongst the stem cells suitable for use in this invention are pluripotent stem cells derived from interchangeable sources all of which will perform as described herein. The pluripotent stem cells may be cells formed after activation of an oocyte, such as a blastocyst, or somatic cells reprogrammed by analytical reprogramming technology. Non-limiting examples are primary cultures or established lines of embryonic stem cells or embryonic germ cells, as exemplified below.

The techniques of this invention can also be implemented directly with primary embryonic or fetal tissue, deriving chondrocytes directly from primary cells that have the potential to give rise to chondrocytes without first establishing an undifferentiated cell line.

Pluripotent Stem Cells

Mammalian pluripotent stem cells are capable of differentiating into more than one differentiated cell type of any of the three primary germ layers endoderm, mesoderm, and ectoderm including neural crest. For the purposes of the present invention, such cells include human induced pluripotent stem cells, human parthenogenetic stem cells derived from a parthenegenetically-activated oocyte (i.e. an egg cell activated without fertilization by a sperm cell), human embryonic stem cells, human embryonic germ cells derived from fetal genital ridges, and some human embryonal carcinoma cells. Pluripotent stem cells may be genetically modified or not genetically modified. By way on nonlimiting example, genetically modified cells may include markers such as fluorescent proteins to facilitate their identification when mixed with other cell types, or modifications of genes relating to immune surveillance to allow the cells to be tolerated allogeneically without rejection.

Embryonic stem cells can be isolated from blastocysts of members of the primate species (U.S. Pat. No. 5,843,780; Thomson et al., Proc. Nati. Acad. Sci. USA 92:7844, 1995) as well as from morula-staged embryos, and epiblast of the embryonic disc. Human embryonic stem (hES) cells can be prepared from human blastocyst cells using the techniques described by Thomson et al. (U.S. Pat. No. 6,200,806; *Science* 282: 1145, 1998; *Curr. Top. Dev. Biol.* 38: 133 ff., 1998) and Reubinoff, et al, *Nature Biotech.* 18:399, 2000).

Briefly, excess human preimplantation embryos generated in the routine course of IVF procedures can be used, or one-cell human embryos can be expanded to the blastocyst stage (Bongso, et al., Hum Reprod 4:706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 minutes three times in DMEM, and exposed to a 1:5 dilution of Guinea pig complement (Gibco) for 3 minutes (Solter, et al., Proc. Nati. Acad. Sci. USA 72:5099, 1975). After two further washes in DMEM, lysed trophectoderm cells are removed from the intact inner cell mass (ICM) by gentle pipetting, and the ICM plated on mitotically-inactivated mouse, human, or avian fibroblast feeder layers.

After 9 to 15 days, the inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on feeder cells in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (.about. 200 U/mL; Gibco) or by selection of individual colonies by micropipette. Clump sizes of about 50 to 100 cells are optimal.

Reprogramming of Somatic Cells

Preparation of Reprogramming Medium:

Most media developed for human Embryonic Stem Cell (hESC) culture do not support RNA reprogramming, as the inclusion of cytokines from the TGFb superfamily can be inhibitory to reprogramming. Use of Pluriton Reprogramming Medium (Stemgent) is supportive of RNA reprogramming. Furthermore, conditioning the Pluriton Medium with reprogramming qualified human newborn foreskin fibroblasts (NUFFs-RQfrom Global Stem) can increase the reprogramming efficiency. One week prior to initiating reprogramming, plate 2.5 million NUFFs per T175 tissue culture treated flask in DMEM with 10% Fetal Calf Serum (DMEM 10% FCS) and culture overnight in a 5% $CO_2$ normoxic incubator. The following day, replace the medium, rinse once with PBS and remove, and then overlay 25 ml of the Pluriton Medium on the irradiated NUFFs. Collect the medium and replenish each day with 25 ml of fresh Pluriton Medium for 5 days. Store the daily fractions at 4 C, pool and then filter through a 0.5µ low adherence filter to remove cellular debris. The conditioned Pluriton Medium can then be used or stored frozen until use.

Preparation of Human Fibroblasts for Reprogramming:

Human dermal fibroblasts derived from patient biopsy samples can readily be reprogrammed into iPS cells with RNA. Prior to initiating reprogramming plate, 2.5 million dermal fibroblasts per T175 tissue culture treated flask in DMEM with 10% Fetal Calf Serum (DMEM 10% FCS) and culture overnight in a 5% $CO_2$ normoxic (21% $O_2$) incubator. Allow the culture to grow to 80% confluence and then dissociate from the plate into a single-cell solution with 0.05% Trypsin EDTA solution. Inactivate the trypsin with DMEM 10% FCS, centrifuge, aspirate and resuspend in DMEM 10% FCS medium at a density 25,000 cells per ml. Re-plate 50,000 target fibroblasts onto one well of a 6-well plate pre-coated with Matrigel (Corning) and culture overnight in a 5% $CO_2$ hypoxic (3-5% $O_2$) incubator overnight.

Transition of Human Fibroblasts to Reprogramming Medium:

Human dermal fibroblasts transfected with a cocktail of microRNAs are more receptive to subsequent reprogramming with mRNA encoding Oct4. Remove the DMEM 10% FCS medium, rinse once with PBS and then replace with 2 ml per well of conditioned Pluriton Medium supplemented with 300 ng/ml of recombinant B18R protein (eBioscience). Replace the plate in a 5% $CO_2$ hypoxic (3-5% $O_2$) incubator for at least 2 hours for the medium to equilibrate.

Transfection of Human Fibroblasts with RNAs:

Transfecting human dermal fibroblasts once with a cocktail of microRNAs prior to subsequent daily transfection with a cocktail of Oct4, Sox2, KIf4, c-Myc and Lin28 (OSKML) synthetic mRNA's can improve overall RNA reprogramming efficiency. To prepare the microRNA transfection complex, in two separate tubes add 3.5 µl of microRNA cocktail (Stemgent) to 21.5 µl of Stemfect buffer and 4 µl of Stemfect transfection reagent to 21 µl of Stemfect buffer. Combine the two and let stand for 15 minutes at room temperature. Add the 50 µl of microRNA transfection complex in a drop wise manner to one well of human fibroblasts in 2 ml of conditioned Pluriton Reprogramming Medium containing B18R. Swirl to mix and replace the plate in a 5% $CO_2$ hypoxic (3-5% $O_2$) incubator for overnight transfection. The following day, aspirate and replace with 2 ml of Reprogramming Medium containing B18R and proceed to transfect with the mRNA cocktail.

To prepare the mRNA transfection complex add 10 µl of the mRNA reprogramming cocktail (Stemgent) containing 1 µg of total mRNA from the (OSKML at a 3:1:1:1:1:1 ratio) to 15p of Stemfect buffer. In a separate tube, add 4 µl of Stemfect to 21 µl of Stemfect buffer. Combine the two and let stand for 15 minutes at room temperature. Add the 50 µl of mRNA transfection complex in a drop wise manner to one well of human fibroblasts in 2 ml of conditioned Pluriton Reprogramming Medium containing B18R. Swirl to mix and replace the plate in a 5% $CO_2$ hypoxic (3-5% $O_2$) incubator for overnight transfection.

Isolation of RNA-Reprogrammed iPS Cell Lines from Human Fibroblasts:

Repeat this daily transfection of mRNA for an additional 7 to 9 transfections. Stop once primary iPS colonies are obvious and change the medium to a defined, feeder-free medium such as E8 (LifeTechnologies). Primary colonies can be manually picked and passaged onto a feeder-free culture system such as E8 on Matrigel within 24-48 hours of the last transfection to expand clonal, stable RNA-reprogrammed iPS cell lines free of any viral or DNA contaminants. Further expansion and characterization can continue as for any human ES or IPS cell line to demonstrate karyotypic stability and retention of pluripotency.

Propagation of Human Pluripotent Stem Cells in an Undifferentiated State

Human pluripotent stem cells such as iPS cells or hES cells can be propagated continuously in culture, using culture conditions that promote proliferation without promoting differentiation. Exemplary serum-containing ES medium is made with 80% DMEM (such as Knockout DMEM, Gibco), 20% of either defined fetal bovine serum (FBS, Hyclone) or serum replacement (WO 98/30679), 1% non-essential amino acids, 1 mM L-glutamine, and 0.1 mM beta-mercaptoethanol. Just before use, human bFGF is added to 4 ng/mL (WO 99/20741, Geron Corp.).

Traditionally, ES cells are cultured on a layer of feeder cells, typically fibroblasts derived from embryonic or fetal tissue. Said feeder cells can be of human, avian, or murine origin. In the case of murine, mouse embryos are harvested from a CF1 mouse at 13 days of pregnancy, transferred to 2.0 mL trypsin/EDTA, finely minced, and incubated 5.0 minutes at 37 degrees C. 10% FBS is added, debris is allowed to settle, and the cells are transferred to a tissue culture vessel with 90% DMEM, 10% FBS, and 2 mM glutamine. To prepare a feeder cell layer, cells are irradiated to inhibit proliferation but permit synthesis of factors that support ES cells (4000 rads gamma.-irradiation). Culture plates are coated with 0.5% gelatin overnight, plated with 375,000 irradiated mouse embryonic fibroblasts per well, and used 5 hours to 4 days after plating. The medium is replaced with fresh hES medium just before seeding the human pluripotent stem cells.

Human pluripotent stem cells can also be maintained in an undifferentiated state even without feeder cells. The environment for feeder-free cultures includes a suitable culture substrate, particularly an extracellular matrix such as Matrigel, HyStem, or laminin. The pluripotent stem cells are plated at >15,000 cells/cm2 (optimally 90,000 cells/cm2 to 170,000 cells/cm2). Typically, enzymatic digestion is halted before cells become completely dispersed (approximately 5 min with collagenase IV). Clumps of about 10 to 2,000 cells are then plated directly onto the substrate without further dispersal. Alternatively, the cells can be harvested without enzymes before the plate reaches confluence by incubating the culture vessel about min in a solution of 0.5 mM EDTA in PBS or mechanically aspirating colonies containing relatively undifferentiated cells with a small cytoplasmic to nuclear area ratio. After washing from the culture vessel, the cells are plated into a new culture without further dispersal. Feeder-free cultures are supported by a nutrient medium containing factors that support proliferation of the cells without differentiation. Such factors may be introduced into the medium by conditioning the medium with cells secreting such factors, such as irradiated (about 4,000 rad) primary mouse embryonic fibroblasts, telomerized mouse fibroblasts, or fibroblast-like cells derived from pluripotent stem cells. Medium can be conditioned by plating the feeders at a density of about 5-6×104 cells/cm2 in a serum free medium such as KO DMEM supplemented with 20% serum replacement and 4.0 ng/mL bFGF. Medium that has been conditioned for 1-2 days is supplemented with further bFGF, and used to support pluripotent stem cell culture for 1-2 days. Alternatively or in addition, other factors can be added that help support proliferation without differentiation, such as ligands for the FGF-2 or FGF-4 receptor, ligands for c-kit (such as stem cell factor), ligands for receptors associated with gp130, insulin, transferrin, lipids, cholesterol, nucleosides, pyruvate, and a reducing agent such as beta-mercaptoethanol. Features of the feeder-free culture method are further discussed in International Patent Publication WO 01/51616; and Xu et al., *Nat. Biotechnol.* 19:971, 2001.

Relatively undifferentiated pluripotent stem cells are desired and under the microscope they appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-30 60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pluripotent stem cells in vitro results in the loss of SSEA-4, Tra-1-60, and Tra-1-81 expression, and increased expression of SSEA-1, which is also found on undifferentiated hEG cells.

Parental Cell Lines of the Invention and Characterization and Differentiation of the Same Throughout the present invention, data is presented for specific human ES cell-derived clonal embryonic progenitor cell lines such as those designated herein as: E3, E72, E75, C4ELS5.1, C4ELSR2, and NP110SM. Additionally, Examples 6 and 7 relate to human ES cell-derived clonal progenitor cell lines designated NP88, NPCC SM19, NPCC SM23, NPCC SM28, NPCC SM31 and NPCC SM40. Compositions, methods, and uses described herein for the cells of the present invention apply to these identical cell lines at different passage levels, as well as pluripotent stem cell-derived clonal, pooled clonal, and oligoclonal embryonic progenitors with the same patterns of gene expression described herein, including said progenitor cell lines manufactured in clinical grade GMP-compatible manufacturing conditions.

All the pluripotent stem cell-derived clonal embryonic progenitor cell lines described in the present invention with the exception of SK1 were derived from the pluripotent stem cell line Envy (Costa et al, The hESC line Envy expresses high levels of GFP in all differentiated progeny, *Nat Methods* 2(4):259-260 (2005) and was expanded by serial trypsinization and passaging in standard cell culture vessels coated with gelatin as described herein to maintain the cells in a relatively undifferentiated progenitor state. The cell line SK1 was derived in a similar manner but from the hESC line H9 (WA09). The culture medium for said expansion of the lines NP88 SM, NP111 SM, NPCC SM19, NPCC SM23, NPCC SM28, NPCC SM31, NPCC SM36, NP92 SM, NP91 SM, NP93 SM, NP95 SM, and NP113 SM was MCDB131 medium with growth supplements: 5% fetal calf serum, 0.5 ng/ml EGF, 2.0 ng/ml basic FGF, and 5.0 µg/ml insulin. The culture medium for the expansion of the lines SK1 and ESI-004-EP SK8, was basal MCDB120 medium containing glutamax 2 mM, and pen/strep 10,000 U/ml, 5% FCS, 50 µg/mL bovine fetuin, 10 ng/mL recombinant EGF, 1.0 ng/mL recombinant bFGF, 10 µg/mL recombinant Insulin, 0.4 µg/mL dexamethasone, and 2.0 mM GlutaMAX-1 supplement.

The cells were then expanded in standard cell culture vessels coated with gelatin, and induced into quiescence by changing the media from the above-described expansion medium, to the same medium with 10% of the normal growth supplements provided by the supplier for five days. Therefore, the quiescence medium was PromoCell Smooth Muscle Cell Medium 2 (Cat. No. 97064) or alternatively (MCDB131 medium) and growth supplement (Cat. No. 39267) obtained from PromoCell GmbH (Heidelberg, Germany) at 10% normal concentrations recommended by the supplier, or 0.5% fetal calf serum, 0.05 ng/ml EGF, 0.2 ng/ml basic FGF, and 0.5 µg/ml insulin. When RNA was extracted from the cells induced into quiescence for 5 days a condition sometimes referred to as "control" or "Ctrl" herein, the cells displayed the pattern of gene expression markers described for the cells in the progenitor states as opposed to the differentiated (adipocyte) state.

The BAT cell progenitors of the present invention when differentiated for 7-21 days in conditions described herein to induce differentiation of the cells into BAT cells, induces the expression of general adipocyte markers such as FABP4 (accession number NM_001442.1, Illumina Probe ID 150373), and CD36 (accession number NM_000072.2, Illumina Probe ID 3310538), as well as BAT-specific markers such as UCP1 (accession number NM_021833.3, Illumina Probe ID 4390348), LIPASIN (also known as ANGPTL8 or C19orf80 or LOC55908 (accession number NM_018687.3, Illumina Probe ID 1430689), and ADIPOQ (accession number NM_004797.2, Illumina Probe ID 4200471) at levels comparable or greater than cultured fBAT cells differentiated in the same conditions. The highest levels of the BAT markers observed in the presence of 1.0 µm rosiglitazone, 2.0 nM T3 hormone+last 4 hours 10 uM CL-316,243 and embedded in HyStem beads the latter comprised of cross-linked thiolated hyaluronic acid and gelatin, while greater levels of cell viability was observed when the cells were also cultured in the presence 10 ng/mL BMP4 or 100 ng/mL BMP7.

It is critical for BAT cells intended to be functionally engrafted in vivo is that the cells will recruit innervation by the sympathetic nervous system. For optimal innervation the engrafted cells are supplemented with Netrin G1, also known as Axon Guidance Molecule. Netrin G1 (NTNG1) belongs to a conserved family of proteins that act as axon guidance cues during vertebrate nervous system development (Nakashiba, et al., 2000 (PubMed 10964959).

Pluripotent stem cell-derived clonal embryonic progenitor cell line NP88, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP88 clonal embryonic progenitor cell line expresses DIO3, DLK1, ZIC2, SLC1A3 and SBSN but does not express COX7A1 and does not express one or more of HOXA5, IL13RA2, DLX5, CRABP1, NEFM, PRG4, and RBP1. Differentiation times for NP 88, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM 19, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM19 clonal embryonic progenitor cell line expresses HOXA2, HOXB2, HOXA5, DLK1, NEFM, and RBP1 but does not express COX7A1 and does not express one or more of ZIC2, DLX5, PRG4, IL13RA2, CRABP1, and SBSN. Differentiation times for NPCC SM19, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM23, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM23 clonal embryonic progenitor cell line expresses HOXA2, ZIC2, THY1 and EFNB2 but does not express COX7A1 and does not express one or more of DLK1, PPP1R1B, and GPC4. Differentiation times for NPCC SM23, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM28, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM28 clonal embryonic progenitor cell line expresses HOXA2, HOXB2, DLX5, and ZIC2, but does not express COX7A1 and does not express one or more of HOXA5, NEFM, PRG4, and RBP1. Differentiation times for NPCC SM28, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM31, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM31 clonal embryonic progenitor cell line expresses HOXA2, DLK1, DLX5, PRG4, and ZIC2 but does not express COX7A1 and does not express one or more of HOXB2, HOXA5, GPC4, NEFM, IL13RA2, NTNG1 and SBSN. Differentiation times for NPCC SM31, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM36, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM36 clonal embryonic progenitor cell line expresses HOXA2, RBP1, and ZIC2, but does not express COX7A1 and does not express one or more of HOXB2, HOXA5, NEFM, PRG4, DLX5, IL13RA2, CRABP1, and SBSN. Differentiation times for NPCC SM36, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM31, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM31 clonal embryonic progenitor cell line expresses HOXA2, DLK1, DLX5, PRG4, and ZIC2 but does not express COX7A1 and does not express one or more of HOXB2, HOXA5, GPC4, NEFM, IL13RA2, NTNG1 and SBSN. Differentiation times for NPCC SM31, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NPCC SM27, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NPCC SM27 clonal embryonic progenitor cell line expresses HOXA2, ZIC2, CD24, and RBP1 but does not express COX7A1 and does not express one or more of DLK1, PPP1R1B, NEFM, and GPC4. Differentiation times for NPCC SM27, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NP78 EN, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP78 EN clonal embryonic progenitor cell line expresses HOXA5, SNAP25, THY1, PAPLN, ZIC2, and DLK1 but does not express COX7A1 and does not express one or more of RBP1, NEFM, and DLX5. Differentiation times for NP78 EN, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NP92 SM, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP92 SM clonal embryonic progenitor cell line expresses DLK1, DLX5, GPC4, and THY1 but does not express COX7A1 and does not express one or more of HOXA2, HOXB2, HOXA5, and SNAP25. Differentiation times for NP92 SM, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NP93 SM, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP93 SM clonal embryonic progenitor cell line expresses SNAP25, PRG4, SBSN, GPC4, and DLK1 but does not express COX7A1 and does not express one or more of HOXA2, HOXA5, HOXB2, and CRABP1. Differentiation times for NP93 SM, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NP113 SM, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP113 SM clonal embryonic progenitor cell line expresses ALDH1A2, SBSN, CPVL, ZIC2, and THY1 but does not express COX7A1 and does not express one or more of HOXA2, HOXA5, HOXB2, RBP1 and CRABP1. Differentiation times for NP113 SM, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line NP91 SM, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The NP91 SM clonal embryonic progenitor cell line expresses BARX1, EPDR1, GPC4, EFNB2, and DLK1 but does not express COX7A1 and does not express one or more of HOXA2, HOXB2, HOXA5, ZIC2, CRABP1, and DLX5. Differentiation times for NP91 SM, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell line SK1, has been demonstrated herein to differentiate to brown adipocytes when differentiated under conditions and for a period of time sufficient for commitment of the cells to a brown adipocyte lineage in the presence of a PPARgamma agonist. The differentiated cell line expresses the UCP1 marker which identifies brown adipocytes. The SK1 clonal embryonic progenitor cell line expresses HOXC6, PAPLN, THY1, RBP1 and EFNB2 but does not express COX7A1 and does not express one or more of HOXA5, ZIC2, and NEFM. Differentiation times for SK1, as well as the other clonal embryonic progenitor cell lines discussed in Example 3, can be from about 2 days-about 21 days; from about 5 days-19 days; from about 9-about 17; or from about 11 days-15 days.

Pluripotent stem cell-derived clonal embryonic progenitor cell lines NP111 SM, NP77 EN, NPBO-EN, and NP85 EN have been demonstrated herein to differentiate to brown adipocytes when differentiated under conditions and for a period of time sufficient for commitment of the cells to a brown adipocyte lineage in the presence of a PPARgamma agonist. The differentiated cell lines express the UCP1 marker which identifies brown adipocytes. The NP111 SM, NP77 EN, NP80-EN, and NP85 EN clonal embryonic progenitor cell lines expresses HOXC6, PAPLN, THY1, RBP1 and EFNB2 but do not express COX7A1 and do not express one or more of HOXA5, ZIC2, and NEFM. Differentiation times for NP111 SM, NP77 EN, NP80-EN, and NP85 EN, as well as the other clonal embryonic progenitor cell lines discussed in Example 3, can be from about 2 days-about 21 days; from about 5 days-19 days; from about 9-about 17; or from about 11 days-15 days.

The cells may be formulated in hydrogels such as HyStem-C (BioTime, Inc. Alameda, CA) wherein the matrix is thiol-modified gelatin and thiolated hyaluronan cross-linked in vivo or in vitro with (polyethylene glycol diacrylate (PEGDA), or in alternative matrices or in solution without said matrices for research and therapeutic applications. For example for transplantation of cells for the treatment of lipid disorders, such as for the treatment of hyperlipidemia or for the induction of beta cell proliferation as a therapeutic modality for type I or type II diabetes, the cells may be formulated in HyStem-C (BioTime, Inc. Alameda, CA) and transplanted subcutaneously at dosages calculated to cause a therapeutically useful reduction in lipids or induction of beta cells and associated insulin.

Parental and Progeny Cell Lines with Reduced Immunogenicity

In various embodiments of the present invention, several methodologies for reducing immunogenicity of the parental and progeny cell lines in order to reduce allogenic rejection could be used prior or after cell differentiation. Ideally, shielding the donor line from any immune rejection could give rise to a universal donor parental cell lines, reducing or eliminating the need for toxic immune rejection prevention drugs in the recipient.

Human leukocyte antigen (HLA) molecules are cell surface proteins present in most cells. They are highly polymorphic and used to present antigens to the immune system to fight disease and eliminate foreign bodies. Class I HLA are heterodimers composed of two main subunits, the macroglobulin (B2M) which is essential for cell surface expression, and the HLA class I heavy chain subunit HLA-A, B, C, E, F, or G. Class I HLA-A, B and C are the major histocompatibility determinants and need to be matched between donors. Class I HLA molecules are important determinants presenting foreign peptides to activate cytotoxic T cells to destroy foreign cells. HLA class II proteins (HLA-DP, DQ and DR) are used by antigen-presenting cells and stimulate the production of antibodies by B Cells to eliminate foreign antigens.

Several methodologies can be used to minimize or eliminate the modulation of the recipient's immune system in response to donor cells. The first one consists in matching donor HLA types with the recipient HLA-type. In one embodiment of the present invention, a series of parental cell lines consisting in a library of pure selected HLA-types representing all or a subset of all possible HLA variants could be used. This would require the generation of a large library of clonally derived cells with representing various HLA types, each clonal line matching a group of recipients with corresponding HLA type.

An alternative approach consists in the removal of HLA alleles, which are responsible for the presentation foreign body antigens to the immune system. Individual HLA alleles could be knocked out individually, or by knocking out the Beta-2 microglobulin (B2M) which is common to all HLA class I and necessary for cell surface expression (Riolobos, L., et al. HLA engineering of human pluripotent stem cells. *Mol Ther* 21, 1232-1241 (2013). HLA class II molecules can be suppressed by knocking out the essential transcription factor gene RFXANK necessary for their expression (DeSandro, A. M., Nagarajan, U. M. and Boss, J. M. Associations and interactions between bare lymphocyte syndrome factors. *Mol Cell Biol* 20, 6587-6599 (2000). To avoid the potential destruction of class I-negative cells by Natural Killer (NK) cells, donor cells can be engineered to expressed a non-polymorphic HLA molecule (HLA-E) which has been demonstrated to inhibit NK cell activation (Lee, N., et al. HLA-E is a major ligand for the natural killer inhibitory receptor CD94/NKG2A. Proc. Nati. Acad Sci USA 95, 5199-5204 (1998).

Several techniques well-known in the art can be used for knocking out/editing various HLA allele and would be evident for people skilled in the art. They may include various DNA vectors, naked or encapsulated in a carrier virus or liposomes used to specifically replace or edit various genes by homologous recombination. Alternatively, other expression knock out approaches such as siRNA, anti-sense oligonucleotides could be used alone or in combination with other knock out approaches.

Another methodology, which could be employed to reduce immunogenicity of donor cells consists in engineering the cells to overexpressed HLA-G. HLA-G is expressed by placental cells during pregnancy and confers immusuppressive properties. HLA-G-modified cells and methods are described in the PCT/US2013/05757 patent application.

Other immune modulation strategies could also be employed in various embodiments of the present invention in order to maximize long-term engraftment of the donor cells in an allogenic recipient. Methodologies that aim at repressing the T-cell activation have been used successfully by Rong, et al (An effective approach to prevent immune rejection of human ESC-derived allografts. *Cell Stem Cell* 14, 121-132 (2008)) to reduce rejection in a mouse model of human allogenic transplantation. Their approach consists in over expressing the Cytotoxic T-Lymphocyte Antigen 4 (CTLA4) and the Programmed Cell Death Ligand 1 (PD-L1), which are known to inhibit T-Cell activation.

In certain embodiments of the present invention when long term engraftment is important to provide a long term clinical benefit, donor cells which could evade or repress immune rejection would be a distinct advantage. Moreover, in a preferred embodiment of the present invention, a universal parental pluripotent stem cell line, such as a human PS cell or ES cell line engineered by the methods described herein alleviate the need to develop multiple progeny lines matching various genetic background of different recipient, or the recourse to toxic immune suppression drugs.

Progenitor Cells that can Give Rise to Brown Fat Cells

In various embodiments described infra the invention provides progenitor cells, e.g. isolated progenitor cell lines that give rise to brown fat cell types. In some embodiments the progenitor cells are capable of differentiation into cells that express one or more markers expressed by various brown fat cells. Exemplary markers expressed by any particular brown fat cell types of the present invention include one or more of the following: FABP4, C19orf80, ADIPOQ, UCP1, PCK1, NNAT, THRSP, CEBPA, CIDEA. In fully mature cells following transplantation into humans corresponding to in vivo-derived brown fat cells from adult or fetal-sources, COX7A1 is expressed. However, COX7A1 is not expressed in the progenitor cells of the present invention or in the brown fat cellular components derived from said progenitors in vitro prior to transplantation in vivo, reflecting that the brown fat cells of the present invention are in a primitive state of differentiation corresponding to the embryonic as opposed to fetal or adult stages of differentiation and have not previously been described in the art.

In some embodiments the invention provides an isolated cell line expressing C19orf80. In some embodiments the invention provides an isolated progenitor cell line expressing UCP1. In some embodiments the invention provides a combined formulation of cells expressing C19orf80 and UCP1.

The isolated progenitor cell line, e.g. the isolated progenitor cell line that gives rise to brown fat cells may be the in vitro differentiated progeny of a pluripotent stem cell. The brown fat cells can be obtained by differentiating the isolated progenitor cell line under suitable culture conditions described infra. Accordingly, brown fat cells of the invention may have essentially the same genome as the parental cell from which it was derived. The parental cell may be the progenitor cell line described infra, or a pluripotent precursor the progenitor cell described infra. Examples of pluripotent precursors of the progenitor cells described infra include ES cells such as hES cells, iPS such as human iPS cells and the like. Thus in some embodiments the brown fat cells of the invention may have a genome that is about 95%, 96%, 97%, 98%, 99% identical to its pluripotent parental cell or cell line. In some embodiments of the invention the brown fat cells of the invention will have a genome that is greater than 90%, greater than 93%, greater than 94%, greater than 95%, greater than 96%, greater than 97%, greater than 98%, greater than 99% identical to its pluripotent parental cell or cell line.

Progenitor Cell Lines

Progenitor cells and progenitor cell lines are used interchangeably herein and refer to cultures of cells that can be propagated for at least 5 passages, but nevertheless are mortal and eventually senesce due to telomere shortening. Certain embodiments of the invention provide progenitor cell lines, methods of making progenitor cell lines and methods of using progenitor cell lines. Progenitor cell lines may, in some embodiments, be the progeny, such as the in vitro progeny, of an embryonic stem cell(s) (e.g. an ES cell(s) such as a hES cell(s)) or an iPS cell(s). The ES cell or iPS cell(s) may be obtained from a mammal, such as a primate. In one embodiment the ES or iPS cell(s) is of human origin. The progenitor cell(s) may be obtained from an established ES cell line available from cell bank, such as WiCell or BioTime, Inc. The progenitor cell may be obtained from ES cell line generated without destroying an embryo or an in vitro fertilized egg (Chung et al. *Cell Stem Cell* (2008) 2:113).

Progenitor cells may include clonal or oligo-clonal progenitor cell lines. Progenitor cells may have the ability to replicate in culture through multiple passages. In some embodiments of the invention the progenitor cells may be passaged about 1-100 times, about 5-90 times, about 10-80 times, about 20-70 times, about 30-60 times, about 40-50 times. In some embodiments the progenitor cells may be passaged about 5 times, about 10 times, about 11 times, about 12 times, about 13 times, about 14 times, about 15 times, about 16 times, about 17 times, about 18 times, about 19 times, about 20 times, about 21 times, about 22 times, about 23 times, about 24 times, about 25 times.

In certain embodiments the invention provides progenitor cell lines that have the ability to differentiate into cells found in an animal body, such as a human. Differentiation may be induced for example, by altering the culture conditions in which the progenitor cells are typically maintained. For example, growth factors, cytokines, mitogens or the like may be added or removed from the culture media.

In some embodiments the progenitor cells are multipotent cells. In some embodiments the progenitor cells are not pluripotent cells. In some embodiments the progenitor cells are not mesenchymal stem cells (MSC). In some embodiments the progenitor cells do not express one or more markers found in a mesenchymal stem cell such as CD74 or markers of cells derived from fetal or adult sources such as COX7A1. In some embodiments the progenitor cells express one or more markers found on an MSC at level that is lower than the expression level found on an MSC. In some embodiments of the invention the progenitor cells do not express CD74. In some embodiments of the invention the progenitor cells express CD74 at level that is lower than the level found on an MSC. In some embodiments the progenitor cell lines express one or more genes expressed by a chondrocyte or a chondrocyte precursor.

In certain embodiments the invention provides a progenitor cell chosen from the cell lines designated C4ELSR2, C4ELS5.1, E3, and NP110SM. In other embodiments the invention provides a progenitor cell line chosen from the cell lines designated NP88, NPCC SM19, NPCC SM23, NPCC SM28, NPCC SM31 and NPCC SM40 (see Examples 6 and 7).

In yet other embodiments the invention provides a progenitor cell line with a pattern of gene expression of the cell line NP110SM expressing one or more genes chosen from: DLK1 (accession number NM_003836.4, Illumina ID 6510259), HOXA5 (accession number NM_019102.2, Illumina ID 6620437), SLC7A14 (accession number NM_020949.1, Illumina ID 6100717), NTNG1 (accession number NM_014917.2, Illumina ID 6940053), HEPH (accession number NM_138737.1, Illumina ID 1850349), PGMS (accession number NM_021965.3, Illumina ID 4480112), IL13RA2 (accession number NM_000640.2, Illumina ID 5420386), SLC1A3 (accession number NM_004172.3, Illumina ID 4210403), and SBSN (accession number NM_198538.1, Illumina ID 4480477). In some embodiments the invention provides a progenitor cell with a pattern of gene expression of the cell line NP110SM that does not express one or more genes chosen from MKX (accession number NM_173576.1, Illumina ID 6620017), NNAT (accession number NM_181689.1, Illumina ID 4010709), HOXD11 (accession number NM_021192.2, Illumina ID 5290142), and DHRS9 (accession number NM_005771.3, Illumina ID 630315). The progenitor cell line has the potential to differentiate into a population of highly purified brown adipocytes that simultaneously express relatively high levels of the BAT gene expression marker UCP1 as well as express relatively high levels the gene expression markers LOC55908 (TD26, betatrophin, C19orf80) (accession number NM_018687.5, Illumina ID 1430689), CIDEC (accession number NM_022094.2, Illumina ID 780309), UCP2 (accession number NM_003355.2, Illumina ID 6580059), ELOVL6 (accession number NM_024090.1, Illumina ID 5670040), (accession number, Illumina ID), CKMT1A (accession number NM_001015001.1, Illumina ID 3420661), and ADIPOQ (accession number NM_004797.2, Illumina ID 4200471), similar to cultured human fetal BAT-derived cells induced to differentiate into brown adipocytes, but unlike said human fetal BAT-derived cells in the preadipocyte or differentiated adipocyte state, the brown adipocytes derived from said hES cell-derived clonal embryonic progenitor cell line designated NP110SM does not express COX7A1 in either the undifferentiated or differentiated states, and when said hES cell-derived clonal embryonic progenitor cell line designated NP110SM is differentiated for 14 days into brown adipocytes, the cells express relatively low or no detectable expression of the gene expression marker CIDEA (accession number NM_001279.2, Illumina ID 10048) unlike cultured human fetal BAT-derived cells which induce relatively high levels of expression of CIDEA when said human fetal BAT-derived cells are induced to differentiate into brown adipocytes.

In certain embodiments, adult-derived cells may be useful in the manufacture of BAT cells for research and therapy. Arterial smooth muscle cells such as coronary smooth muscle cells that are derived from individuals exposed to high levels of circulating ketone bodies such as may be present in individuals with significant long-term alcohol intake are capable of BAT cell differentiation using the methods disclosed herein. In addition, said smooth muscle cells capable of BAT cell differentiation may be transiently or permanently immortalized through the exogenous expression of the catalytic component of telomerase (TERT), thereby allowing the industrial expansion of said progenitors to BAT cells. Similarly, fetal or adult BAT tissue-derived preadipocytes may be transiently or permanently immortalized through the exogenous expression of the catalytic component of telomerase (TERT), thereby allowing the industrial expansion of said progenitors to BAT cells.

Any of the progenitor cell lines described infra may be used in the methods described infra. For example the progenitor cell lines may be contacted with a member of the TGF-beta superfamily and induced to differentiate. The progenitor cell lines described infra may be contacted with retinoic acid and induced to differentiate. The progenitor cell lines described infra may be contacted with an agonist or antagonist of PPARγ and induced to differentiate. The progenitor cell lines described infra may be contacted with a thyroid hormone such as T3 or T4 and induced to differentiate. The progenitor cell lines described infra may be contacted with an adrenergic hormone such as epinephrine or norepinephrine and induced to differentiate. The progenitor cell lines described infra may be incubated at temperatures substantially below 37 deg C. and induced to differentiate. The progenitor cell line may be cultured in a hydrogel at temperatures substantially below normal body temperature, as described infra, with or without a differentiation agent such as a member of the TGF-β superfamily, retinoic acid, agonist of PPARγ, adrenergic agonist, and thyroid hormone.

To improve the scalability of purified somatic progenitors from hPS cells, we previously reported the generation of a library of >140 diverse clonal human embryonic progenitor (hEP) cell lines as source of purified cell types with site-specific homeobox gene expression. We designated these novel cell lines "embryonic progenitors" because they show the potential to be propagated extensively in vitro and can subsequently differentiate in response to diverse growth factors and inducers. The term therefore refers to cells with an intermediate differentiated state between pluripotent cells and terminally differentiated cell types.

In certain embodiments disclosed herein, the comparative site-specific gene expression of clonal embryonic progenitor cell lines capable of differentiating into site-specific adipocytes with patterns of gene expression useful in generating brown fat cells is provided and along with the disclosure of their diverse responses when differentiated in the presence of one or more TGF-beta superfamily members, such as, TGF-beta proteins including TGFβ3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Müllerian Inhibiting Substance (MIS), Inhibins, and Nodal.

In still other embodiments the invention provides a cell culture comprising the progenitor cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein, cultured in micromass or cultured in a hydrogel. The cell culture may comprise one or more TGF-beta proteins including TGFβ3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Mulllerian Inhibiting Substance (MIS), Inhibins, and Nodal.

Therefore, the present invention describes a composition comprising a first and a second cell population, wherein the first cell population comprises the relatively undifferentiated clonal, pooled clonal, or oligoclonal embryonic progenitor cells from which the second population is derived, and the second population comprises the in vitro differentiated progeny of the first cell population, wherein the cells of the second cell population express FABP4 and either UCP1, C19orf80, or ADIPOQ at levels comparable to cultured fBAT cells.

Clonal Embryonic Vascular Endothelial Cells Expressing ITLN1 or ITLN2

In another embodiment, pluripotent stem cells such as hES or iPS cells are differentiated in vitro to generate vascular endothelial cells that express omentin 1 (ITLN1) or intelectin-2 (ITLN2) and used in combination with the SVF, hydrogels, or the brown fat progenitors of the present invention. Said ITLN1 or ITLN2-expressing endothelial cells are generated in the presence of Activin-A and WNT-3A followed by FGF-4 and BMP-2 and then cloned as monoclonal cell lineages on Matrigel, gelatin, or similar supportive culture support in the presence of media capable of supporting the growth of vascular endothelial cells. More specifically, hES or iPS cells are cultured as colonies on fibroblast feeder cells that are allowed to overgrow and differentiate in situ for 13 days in ES cell culture medium such as Invitrogen KO-DMEM with KO-serum replacement. Then, on differentiation day 0 (FIG. 6), media is changed to a basal differentiation media comprising KO-DMEM/RPMI-1640 (5/1 v/v) and said basal differentiation media is supplemented with 100 ng/mL Activin A and 25 ng/mL Wnt3A. On the beginning of day 2 (designated Day 1 in FIG. 6), and for the following two days the media is replaced with the said basal differentiation medium supplemented only with 100 ng/mL Activin A. Then on the beginning of day 4 (designated Day 3 on FIG. 6), the media is replaced with the said basal differentiation media supplemented with 30 ng/mL FGF4 and 20 ng/mL BMP2. At the beginning of Day 8 (designated Day 7 in FIG. 6), cells are rinsed twice in PBS and disaggregated with Accutase, and plated on Matrigel-coated plates in medium capable of supporting the proliferation of vascular endothelial cells supplemented with a TGFβ signaling inhibitor such as SB431542. A nonlimiting example of said endothelial media MCDB 131 supplemented with 5.0 ng/mL VEGF-A, 5.0 ng/mL FGF-2, 0.75 IU/mL heparin, 2% FBS (such as Promocell endothelial MV2 media with supplements at concentrations normally recommended by the manufacturer and sold as a complete kit (Cat #C-22022) or as cell basal medium (Cat #C-22221) and growth supplement (Cat #C-39221) and a TGFβ signaling inhibitor such as SB431542. Cells are expanded as working stocks of candidate cultures that can be expanded and cryopreserved for the purposes of deriving continuous clonal cell lines. The candidate cultures are plated at approximately 500 and 2,000 cells in 15 cm tissue culture dishes coated with Matrigel or suitable substrate for the culture of endothelial cells, and allowed to grow to visible cell colonies which are subsequently isolated by various means known in the art such as the use of cloning cylinders, and serially propagated as cell lines which are then expanded in the same media and matrix, and cryopreserved for future use.

Uses of said cells, in particular, those that have been produced in a manner such that the cells may be permanently engrafted in the host without rejection such as to produce Universal Donor Cells as described herein, including but not limited to those produced from iPS cells, that express vascular endothelial markers such as PECAM1, CDH5 (VE-Cadherin), and vWF include transplantation to increase blood flow in transplanted adipose tissue and to express ITLN1 (Omentin) or ITLN2 for therapeutic effect. Particularly useful are clonal, pooled clonal, oligoclonal, or pooled oligoclonal endothelial cell lines that express relatively high levels of ITLN1 (Omentin) or ITLN2 and are useful in imparting increased sensitivity to insulin in Type II diabetes, aged, or Syndrome X patients. Said ITLN1-expressing endothelial cell lines are may be co-injected with hydrogels, SVF and the cells of the present invention to further promote vascularization, reduce inflammatory pathways, increase insulin sensitivity in said patients. The dosage of said cells will vary from patient to patient but can be easily be determined by measuring the serum or plasma levels of Omentin in the patient. As has been reported (Zhong, et al, *Acta Pharmacol Sin* 32: 873-878) serum omentin levels approximate 254 ng/ml+/−72.9 ng/ml in normal patients and are observed to be 113 ng/ml in patients with acute coronary syndrome, and 155 ng/ml in patients with stable angina pectoris. Plasma levels in normal patients have also been reported to be 370 ng/mL (de Souza Batista et al, *Diabetes* 56: 1655-1661), differences that may be attributable to differences in assay technique. Dosages will vary based on the site of injection and disease status of the patient, but will typically be $1\times10^6$ to $1\times10^9$ cells/patient, formulated in a suitable buffer or matrix such as hydrogels composed of crosslinked hyaluronic acid and gelatin such as HyStem-C (BioTime, Alameda, CA).

Clonal Embryonic Progenitor Line Nomenclature:

Many of the human embryonic progenitor cell lines used in the work described infra have been previously described including the lines C4ELS5.1, E3, E72, E75, E163 and cells with a similar pattern of gene expression (See, e.g., US Patent Publication Nos. 20120171171 and 20100184033 both of which are incorporated by reference in their entirety). In addition, cells that express EYA4 capable of differentiating into cellular components of BAT have also been described (see WO2011/150105 entitled "Improved Methods of Screening Embryonic Progenitor Cell Lines,") as well as (U.S. patent application Ser. No. 13/683,241, entitled "Methods of Screening Embryonic Progenitor Cell Lines"). The clonal embryonic progenitor cell line NP110SM and cells with a similar pattern of gene expression are described in [US Patent Publication No. 2015/0275177]. Nomenclature of the lines includes their alternative designations along with synonyms that represent minor modifications that result from the manipulation of the names resulting from bioinformatics analysis, including the substitution of "-" for "." and vice versa, the inclusion of an "x" before cell line names beginning with an arabic number, and suffixes such as "bio1" or "bio2" that indicate biological replicates of the same line which are examples of cases where a frozen ampule of the same line was thawed, propagated, and used in a parallel analysis and "Rep1" or "Rep2" which indicate technical replicates wherein RNA isolated from a given cell line is utilized a second time for a repeat analysis without thawing or otherwise beginning with a new culture of cells. Passage number (which is the number of times the cells have been trypsinized and replated) for the cell lines is usually designated by the letter "P" followed by an arabic number, and in contrast, the population doubling number (which refers to the number of estimated doublings the cell lines have undergone in clonal expansion from one cell) is designated by the letters "PD" followed by an arabic number. The number of PDs in a passage varied from experiment to experiment but generally each trypsinization and replating was at a 1:3 to 1:4 ratio (corresponding to an increase of PDs of 1.5 and 2 respectively). In the expansion of clones, the original colonies were removed from tissue culture plates with cloning cylinders, and transferred to 24-well plates, then 12-well, and 6-well as described above. First confluent 24 well is designated P1, the first confluent 12 well culture is P2, the first 6-well culture is P3, then the six well culture was then split into a second 6 well plate (P4) and a T25 (P4). The second 6 well at P4 is utilized for RNA extraction (see U.S. Patent Publication No. 20100184033 incorporated herein by reference in its entirety) and represents about 18-21 PD of clonal expansion. Typical estimated 5 subsequent passages and PDs are the following split to a T75 flask (19.5-22.5 PD), the P6 passage of the cells to a T225 flask (21-24 PD), then P7 being the transfer of the cells to a roller bottle (850 cm$^2$, 23-26 PD), and P8 the split into 4 rollers (25-28 PD). The ranges shown above in parenthesis represent estimated ranges in cell counts due to cell sizes, attachment efficiency, and counting error.

Propagation of Clonal, Pooled Clonal, Oligoclonal, and Pooled Oligoclonal Cell Lines.

Aspects of the invention provide methods for identifying and differentiating embryonic progenitor cell lines that are derived from a single cell (clonal) or cell lines that are "pooled clonal" meaning that cell lines cloned have indistinguishable markers, such as gene expression markers, and are combined to produce a single cell culture often for the purpose of increasing the number of cells in a culture, or are oligoclonal wherein a line is produced from a small number, typically 2-1,000 similar cells and expanded as a cell line, or "pooled oligoclonal" lines which are lines produced by combining two or more oligoclonal cell lines that have indistinguishable markers such as patterns of gene expression. Said clonal, pooled clonal, oligoclonal, or pooled oligoclonal cell lines are then propagated in vitro through removal of the cells from the substrate to which they are affixed, and the re-plating of the cells at a reduced density of typically ⅓ to ¼ of the original number of cells, to facilitate further proliferation. Examples of said cell lines and their associated cell culture media is disclosed in U.S. patent application Ser. No. 12/504,630 filed on Jul. 16, 2009 and titled "Methods to Accelerate the Isolation of Novel Cell Strains from Pluripotent Stem Cells and Cells Obtained Thereby"; and West et al., 2008, *Regenerative Medicine* vol. 3(3) pp. 287-308. The compositions and methods of the present invention relate to said cell lines cultured as described but for greater than 21 doublings of clonal expansion.

Methods of Isolating Clonal Embryonic Progenitor Cell Lines with a Pattern of Gene Expression and Differentiation Potential Comparable to Fetal-Derived Brown Adipocytes Human pluripotent stem cells, such as human ES cells are maintained on mouse embryonic fibroblast feeder cells in hES cell culture medium consisting of DMEM with high glucose (Invitrogen, Cat #11960-044) supplemented with 20% FCS (Invitrogen, 16000), 1×non-essential amino acids (Invitrogen, Cat #12383-014), 2 mM L-Glutamine (Invitrogen, Cat #25030-081), 1% v/v Insulin Transferrin Selenium supplement (Invitrogen, Cat #41400-045), and 0.1 mM β-mercaptoethanol (Invitrogen, Cat #21985-023), either with or without 50 ng/ml FGF2 (Strathmann, 130-093-842) supplementation. To maintain and expand, hES cells are passaged either by manual micro-dissection or by enzymatic dissociation using 1 mg/ml Collagenase NB6 (Serva, 17458).

Initial Differentiation of hES Cells for BAT Progenitor Derivation

The cells are initially differentiated in preparation for the generation of candidate cultures which function as stock cultures from which clonal progenitor cells with the gene expression profile of the NP110SM line can be isolated. In the example provide below, the hES cell line hES3 (Envy) are incubated with 1 mg/ml Collagenase for 60 minutes after which the dish was gently tapped to release the hES cell colonies into suspension. These colonies were collected and triturated to generate small clumps which were plated into ultra-low attachment plates (CoStar, Corning, Cat #3471) for embryoid body (EB) formation. The EBs were formed in neural differentiation medium consisting of DMEM/F12 with Glutamax I (Invitrogen, Cat #10565-018) and 1× B27 supplement without Vitamin A (Invitrogen, Cat #12587-010) (referred to as "NP(−)" medium henceforth) and supplemented with 500 ng/ml recombinant human Noggin (R & D systems, Cat #3344-NG-050) and 20 ng/ml bFGF (Strathmann, 130-093-842). Over the next 21 days, spent medium was removed every 48 hours and fresh medium supplemented with 500 ng/ml Noggin and 20 ng/ml bFGF was added to the EBs. On day 21, spent medium was removed and fresh medium supplemented with 20 ng/ml bFGF only was added to the EBs. Reagents were sourced from Invitrogen unless otherwise stated. Neural EB formation was apparent in the culture.

Generation of Stock Candidate Cultures

To generate candidate cultures for clonal isolation, the above-mentioned EBs on day 22 (after one day FGF2-only culture) were dissociated with Accutase (Innovative Cell Technologies, AT-104) for 10 minutes at 37° C. followed by trituration to generate a single cell suspension. The cell suspension in PBS was divided into four tubes and each aliquot was diluted with NP(−) medium (as described above)+20 ng/ml bFGF (designated NP(+) medium herein). Cells were centrifuged at 180 g for 5 minutes and each pellet was seeded into one well of a 6-well tissue culture plate in the NP(+) medium. The medium was changed 24 hours after initial plating and then 3 times a week thereafter. Upon confluence, cells in the 6-well plate were dissociated using TrypLE (Invitrogen, Cat #12563-029) for 5 minutes at 37° C. and replated in progressively larger tissue culture vessels being: T25 flask, T75 flask and T225 flask in the NP(+) medium over a period of several weeks to reach a T225 expansion stage of confluent cells.

Candidate cultures of confluent cells in the T225 flask were then dissociated using TrypLE, counted and an aliquot of this single cell suspension was diluted to a concentration of 10,000 cells/ml in the NP(+) media that was used for culture to the T225 stage candidate culture stage. An aliquot of the single cell suspension was then plated at clonal dilution (500-7000 cells per 50 ml that went into the 15 cm dish) in 0.1% Gelatin-coated (Sigma, Cat #G1393) 15 cm dishes in the NP(+) medium. Remaining cells from the candidate cultures were cryopreserved (typically $3 \times 10^6$ to $5 \times 10^6$ cells/vial) using a controlled rate freezer program and freezing media for cryostorage and future use.

Generation of Clonal Embryonic Progenitor Cell Lines From Candidate Cultures

Cloning dishes were prepared by adding 50 ml of the above-mentioned NP(+) medium into Gelatin-coated (0.1%) 15 cm culture dishes. To each dish, a preparation of a single cell suspension from the candidate culture propagated in the NP(+) medium was then manually diluted by adding to the 15 cm culture dishes that volume of cells determined by counting a suspension of cells such that there were a selection of the following dilutions of cells; 500 cells/dish or, 1000 cells/dish or; 1500 cells/dish or; 3000 cells/dish, 5000 cells/dish or 7000 cells/dish to achieve different densities of the single cell suspension and to aid in the isolation of single colonies grown from a single cell. Alternatively, cells can be dispersed as single cells using an automatic cell deposition unit, or said automatic deposition can be used following flow sorting or other affinity purification techniques known in the art such as antibody-based selection, including monoclonal antibody-based immunoselection using flow cytometry or antibodies conjugated to magnetic beads to select cells to select cells enriched for antigens present on NP110SM cells. Such antigens may include Interleukin 13 Receptor, Alpha 2 (IL13RA2), also known as CD213A2, also known as Cancer/Testis Antigen 19.

In the case of manual dilution of cells, three separate dishes with any three of the above mentioned densities were optimised such that discrete, easily isolatable single colonies could be observed for isolation and expansion as embryonic progenitor cell lines. Seeded single cells of an appropriate dilution were distributed evenly in the dish by the sliding the 15 cm dish alternately in a clockwise, followed by counter-clockwise, then side to side (left to right) motion, followed by a forward and back motion repeatedly, for about 30 seconds inside the incubator. Dishes were then incubated in a $CO_2$ incubator (5% $CO_2$, 20% $O_2$) and left undisturbed without moving or feeding for 14 days to allow single cells to attach to the culture dish surface and for colonies to grow to sufficient size for isolation. NP(+) media previously conditioned by the NP110SM cells for 24-48 hours can be used to increase the number and rate of proliferation of the resulting colonies.

Dishes were visually inspected and well-separated cell colonies were picked with sterile cloning cylinders (Sigma, Cat #CLS31666, CLS31668 & CLS316610) using 25 ul TrypLE for a 6 mm cylinder, 50 ul TrypLE for an 8 mm cylinder and 100 ul TrypLE for a 10 mm cylinder. Each isolated cell colony was then plated into one well each of 0.1% Gelatin-coated 24 well plates (Nunc, 142475) containing 1 ml of Promocell Smooth Muscle Cell Growth Medium 2 or its equivalent medium (designated SM medium herein). In this instance of the method, isolated embryonic progenitor cells are further cultured in the SM media. Upon confluence, cells in the 24-well plate were dissociated using TrypLE for 5 minutes at 37° C. and replated in progressively larger tissue culture vessels being: one well of a 6-well plate, T25 flask, T75 flask and T225 flask(s) in the SM medium over several weeks (an average of 1-2 weeks between each passage). Confluent cells in the T225 flask(s) were cryopreserved and banked as an isolated Embryonic Progenitor Cell Lines and seeded for immunostaining and RNA isolation, such as for PCR amplification of the transcripts for HOXA5 and IL13RA2 as a first pass screen for cells with a pattern of gene expression like that of the clonal cell line NP110SM.

Methods of Screening Embryonic Progenitor Cells for Potential for Differentiation into Cellular Components of Brown Adipose Tissue Cells such as clonal pluripotent stem cell-derived embryonic progenitors or pooled populations of said clonal lines, or oligoclonal cultures of said progenitor cells are directly scalable cell cultures simply by serially passaging the cells in the original medium in which they were clonally expanded from a single cell and by disaggregating and replating the cells at a lower density such as a 1:2 or 1:4 split at passaging just before the cells reach confluence, thereby preventing undesired differentiation that may occur at high density. Said cells may then be exposed to differentiation conditions as described herein. By way of nonlimiting example, hES cell-derived clonal embryonic progenitor cell lines can be cultured in HyStem Bead Differentiation Condition as described herein wherein the Differentiation medium is supplemented with 1.0 µM rosiglitazone, and 2.0 nM triiodothyronine (T3) with or without additional 10 ng/ml BMP4. Plates were then placed in a humidified incubator at 37° C. with ambient $O_2$ and 10% $CO_2$, and the cells were fed three-times weekly for 14-21 days. For the last 4 hours prior to use, 10 µM CL-316,243 was added to the culture medium. Preferably the conditions and time of differentiation are constant with the diverse clonal embryonic progenitor cells. Differentiated cells can then be assayed for markers of differentiation by methods known in the art including gene expression reporter constructs, immunocytochemistry, and by the isolation of RNA and analysis of the mRNA transcripts in said samples by PCR or gene expression microarray. Samples that express FABP4 (accession number NM_001442.1, Illumina ID 150373) and CD36 (accession number NM_000072.2, Illumina ID 3310538) are considered to be differentiation into adipocytic lineages.

Said cell cultures that express adipocyte markers such as FABP4 and simultaneously express the gene BETATROPHIN (accession number NM_018687.3, Illumina ID 1430689) (also known as C19ORF80, LOC55908, and C19Orf80) can be considered as hits and are therefore candidates for progenitors of brown adipose tissue cells.

Methods of Differentiating Progenitor Cells

In certain embodiments the invention provides a method of differentiating a progenitor cell in vitro, such as a hEP cell, to a more differentiated state (e.g., such as one or more of the differentiated progeny of progenitor cells described infra), relative to the starting progenitor cell, comprising contacting the progenitor cell with one or more members of the TGFβ super family. In some embodiments the TGFβ superfamily member may be chosen from TGF-beta proteins including TGFβ3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Mülllerian Inhibiting Substance (MIS), Inhibins, and Nodal. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising contacting the progenitor cell with a retinol, such as retinoic acid. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising contacting the progenitor cell with a thyroid hormone such as T3 or T4. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising contacting the progenitor cell with an adrenergic agonist such as epinephrine, norepinephrine, or the highly selective beta 3-adrenergic agonist, CL316243 (J. D. Bloom, M. D. Dutia, B. D. Johnson, A. Wissner, M. G. Burns, E. E. Largis, J. A. Dolan, and T. H. Claus., *J. Med. Chem.* 35: 3081, 1992). The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising contacting the progenitor cell with physiologically-active concentrations of the growth factor FGF21. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising incubating the progenitor cell at temperatures substantially below that of normal body temperature. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides a method of differentiating a progenitor cell in vitro, such as a hEP cell, to a more differentiated state relative to the starting progenitor cell comprising contacting the progenitor cell with PPARγ agonists such as rosiglitazone. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In other embodiments the invention provides methods to extend the lifespan of fetal or adult-derived BAT cells or arterial smooth muscle cells such as coronary artery smooth muscle cells from individuals exposed to long-term alcohol consumption and resulting long-term exposure to relatively high levels of ketone bodies through the exogenous expression of the catalytic component of telomerase (TERT), wherein the cells can be expanded on an industrial scale and genetically modified to escape immune surveillance.

In other embodiments the invention provides a method of differentiating a progenitor cell in vitro, such as a hEP cell, to a more differentiated state relative to the starting progenitor cell comprising contacting the progenitor cell with combinations of: one or more members of the TGFβ superfamily such as TGF-beta proteins including TGFβ3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Mülllerian Inhibiting Substance (MIS), Inhibins, and Nodal, a retinol, such as retinoic acid, a thyroid hormone such as T3 or T4, an adrenergic agonist such as epinephrine, norepinephrine, or the highly selective beta 3-adrenergic agonist, CL316243, and a PPARγ agonist such as rosiglitazone. The progenitor cell may be any progenitor cell disclosed infra. In one embodiment the progenitor cell is chosen from the cell lines C4ELSR2, C4ELS5.1, E3, E72, E75, E163, NP110SM, NP88, NPCC SM19, NPCC SM23, NPCC SM28, NPCC SM31 and NPCC SM40 or cell lines with a pattern of gene expression of C4ELSR2, C4ELS5.1, E3, E72, E75, E163, NP110SM, NP88, NPCC SM19, NPCC SM23, NPCC SM28, NPCC SM31 and NPCC SM40 as described herein.

In one embodiment of the methods disclosed infra the progenitor cell is comprised of a micromass. In another embodiment the progenitor cell is differentiated by one or more differentiation conditions described herein and is in contact with a hydrogel. In some embodiments the progenitor cell is encapsulated within the hydrogel. The hydrogel may be comprised of hyaluronate. The hyaluronate may be thiolated. The hydrogel may be comprised of gelatin. The gelatin may be thiolated. Preferably, the hydrogel is comprised of thiolated hyaluronate or thiolated carboxymethylhyaluronate in combination with thiolated gelatin or thiolated carboxymethylgelatin. The hydrogel may comprise a crosslinker. The crosslinker may be comprised of an acrylate. In one embodiment the acrylate is PEG diacrylate.

In some embodiments the more differentiated cell expresses one or more genes described infra as being expressed by an in vitro differentiated progeny of a progenitor cell. In some embodiments the in vitro differentiated progeny express one or more genes expressed by a adipocyte, e.g. FABP4 and CD36. In some embodiments the in vitro differentiated progeny express one or more genes expressed by a BAT cell progenitor or a mature BAT cell, e.g. UCP1, ADIPOQ, or C19ORF80 (also known as BETATROPHIN). In some embodiments the differentiated progeny express one or more genes expressed by an adipose cell.

Progeny of Progenitor Cell Lines

In certain embodiments the invention provides the progeny of a progenitor cell line. The progenitor cell line may be an embryonic progenitor cell line such as a human embryonic progenitor cell line (hEP). The progeny of the progenitor cell line may be the in vitro progeny of the progenitor cell line and may include one or more cells that are more differentiated compared to the parental progenitor cell line. The differentiation state of a cell may be determined by analyzing one or more genes expressed by the progeny cell relative to the parental progenitor cell line and/or accessing a database containing information regarding gene expression of cells at various stages of development, such as the LifeMap database. The progeny of the progenitor cell line may be a cell expressing one or more genes typically expressed by a cell in a developing mammalian embryo, such as a primate (e.g. a human). For example the progeny of the progenitor cell line may express one or more genes corresponding to an adipocyte cell fate chosen from: FABP4, CD36, CIDEA, ADIPOQ, UCP1, C19orf80, NTNG1, and THRSP.

In certain embodiments the invention provides a cell culture comprising the in vitro progeny of a progenitor cell line such as a hEP cell line. In some embodiments the cell culture may comprise one or more growth factors, cytokines and/or mitogens. In certain embodiments the cell culture may comprise one or more members of the TGF-β superfamily. Exemplary members of the TGFβ superfamily include TGF-beta proteins including TGFβ3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Müllerian Inhibiting Substance (MIS), Inhibins, and Nodal. In certain embodiments the cell culture may comprise cells cultured in the presence of combinations of cytokines, factors, or conditions that induce the differentiation of brown fat cells including: culturing the cells in or without a hydrogel at temperatures substantially below normal body temperature, as described infra, with or without a differentiation agent such as a member of the TGFβ superfamily, retinoic acid, agonist of PPARγ, adrenergic agonist, and thyroid hormone. In certain embodiments the cell culture may comprise cells embedded in a hydrogel. Suitable hydrogels may comprise one or more polymers. The polymers may include any polymer known to form a hydrogel including hyaluronate, gelatin, acrylate and the like. In some embodiments the hydrogel is comprised of thiolated hyaluronate. In some embodiments the hydrogel is comprised of thiolated gelatin. In some embodiments the hydrogel is comprise of acrylate crosslinker such PEG diacrylate.

In some embodiments the invention provides a cell culture comprising the in vitro progeny of a progenitor cell line wherein the in vitro progeny of a progenitor cell line is an adipose cell precursor or a mature adipocyte. In certain embodiments of the invention the in vitro progeny of the progenitor cell line, e.g. an adipose precursor may comprise about 5% of the cells in culture, about 10% of the cells in culture, about 15% of the cells in culture, about 20% of the cells in culture, about 25% cells in culture, about 30% of the cells in culture, about 35% of the cells in culture, about 40% of the cells in culture, about 45% of the cells in culture, about 50% of the cells in culture, about 55% of the cells in culture, about 60% of the cells in culture, about 65% of the cells in culture, about 70% of the cells in culture, about 75% of the cells in culture, about 80% of the cells in culture, about 85% of the cells in culture, about 90% of the cells in culture, about 95% of the cells in culture, about 99% of the cells in culture.

Use of HyStem-C to Cryopreserve Cells in Beads and to Modify MYH11 and FABP4 Gene Expression in Human Cells.

HyStem-C (BioTime, Inc. Alameda, CA) is a matrix composed of thiol-modified gelatin and thiolated hyaluronan crosslinked in vivo or in vitro with (polyethylene glycol diacrylate (PEGDA). We observed that clonal human embryonic progenitor cell lines such as those described in the present invention, could be frozen and thawed within beads of polymerized HyStem-C (BioTime, Inc. Alameda, CA) such as 25 µl aliquots of $2.0 \times 10^7$ cells/mL (in FBS that is 10% DMSO) in 1% w/v HyStem-C (BioTime, Inc. Alameda, CA) (500,000 cells/bead). This facilitates the accumulation of large numbers of beads with large numbers of diverse hEP cell types that can be simultaneously thawed and assayed such as in high throughput robotic systems wherein the beads are exposed to diverse differentiation conditions and their differentiation assayed by gene expression microarray or other means known in the art. It also makes possible the thawing of large numbers of cryopreserved beads and the incubation of combinations of beads with diverse types of embedded cells and subsequent analysis of changes of differentiated state such as gene expression microarray or other means known in the art.

In addition, the incubation of hEP cell lines in HyStem-C (BioTime, Inc. Alameda, CA) allowed the accumulation of a large amount of data on the biological influence of HyStem-C (BioTime, Inc. Alameda, CA) on diverse cell types. With Illumina gene expression microarray data from more than 3,000 differentiation experiments, we searched for genes frequently up- and down-regulated in HyStem-C (BioTime, Inc. Alameda, CA) beads and compared those profiles to those obtained under micromass conditions. For example, we observed that cells cultured in HyStem-4D (Biotime, Inc. Alameda, CA) beads with BMP4 frequently exhibited a marked decrease in myofibroblast markers such as MYH11, and increased expression of adipocyte markers such as FABP4 and anti-inflammatory markers such as TIMP4. The cell line E15, which in other conditions was shown to have chondrogenic potential and the line W10 strongly induced MYH11 in micromass conditions supplemented with 10 ng/mL BMP4, but this induction was essentially ablated in HyStem-C (BioTime, Inc. Alameda, CA) culture supplemented with BMP4. Instead, in HyStem-C (BioTime, Inc. Alameda, CA) beads, the line markedly upregulated expression of DCN, a marker of meninges. This physiological effect on myofibroblastic differentiation seen in many lines cultured in HyStem-C (BioTime, Inc. Alameda, CA) beads (i.e., the strong reduction in MYH11 expression) has therapeutic implications in vivo, such as in inhibiting fibrosis or adhesions. It also is of benefit in surgical settings where cells could be transplanted to regenerate tissue function while inhibiting adhesions and related fibrotic process at the surgical site.

As previously described (see, U.S. patent application Ser. No. 14/048,910, incorporated by reference) diverse clonal embryonic progenitor cell lines show correspondingly diverse differentiation responses to growth factors such as members of the TGF-beta superfamily. In some cases, including but not limited to the culture of the cells in HyStem-C (BioTime, Inc. Alameda, CA) beads in the presence of BMP4, some cell lines strongly express markers of adipocytes such as FABP4 and CD36. Because the clonal progenitor cell lines capable of adipocyte differentiation represent mesenchymal anlagen of diverse anatomical origin, the corresponding adipocytes may represent fat-forming cells with diverse phenotypes. Some of these diverse phenotypes offer novel therapeutic opportunities as described herein.

The C19orf80-expressing adipocytes of the present invention, are also useful in treating type I and type II diabetes. In said therapeutic applications, the C19orf80-expressing adipocytes of the present invention may be injected into the body, by way of nonlimiting example, the cells in a concentration of 2.5×105 cells/ml to 1.0×108 cells/ml in HyStem-C (BioTime, Inc. Alameda, CA), preferably 1.0× 107 cells/ml, or at these concentrations in other matrices useful in promoting cell engraftment. The site of engraftment may vary, but by way of example, the cells may be injected subcutaneously at the normal site of brown fat cells in humans such as in the interscapular region of the back. The cells may or may not also be genetically-modified, with modifications to increase C19orf80 expression, such as those that down-regulate the insulin receptor gene, or allow the inducible apoptosis of the engrafted cells, or modification to promote the allogeneic histocompatibility of said cells.

In some applications, said C19orf80-expressing adipocytes are mitotically inactivated as described herein to limit their lifespan and lead to a transient expression of C19orf80 to transiently induce the proliferation of pancreatic beta cells.

In aged patients, pancreatic beta cell proliferation in response to the transplanted C19orf80-secreting adipocytes or alternatively, the pancreatic beta cell proliferation in response to administered C19orf80 protein, or simply the pancreatic beta cell proliferation in response hypoinsulinemia, can be facilitated by the extension of telomere length in the beta cells or beta cell precursors by the exogenous expression of the catalytic component of telomerase reverse transcriptase, such as human TERT. The telomerase catalytic component of telomerase may be introduced by varied methods known in the art such as viral gene therapy, including but not limited to adenoviral vectors.

Provided herein are improved methods and compositions comprising hEP cells and their differentiated progeny as well as methods for directing the differentiation of hEP cells to mature brown fat cells useful in research and for treating certain metabolic and vascular disorders.

Methods and Compositions for Cryo-Preserving Cells

In some embodiments the invention provides methods for cryo-preserving the cells described infra. In other embodiments the invention provides compositions comprising cryo-preserved cells, wherein the cell is one or more cells described infra.

In certain embodiments the invention provides a composition comprising a cryopreserved progenitor cell, such as hEP cell described infra. The composition may comprise at least 1 progenitor cell, at least 10, at least 100, at least 1,000, at least 10,000, at least 100,00, at least 1,000,000 viable cryo preserved progenitor cells. The composition may comprise about 1 progenitor cell, about 10, about 100, about 1,000, about 10,000, about 100,000, about 1,000,000 viable cryo preserved progenitor cells. The cryopreserved progenitor cell may further comprise a hydrogel wherein the progenitor cell is seeded within the hydrogel. The cryopreserved progenitor cell may include a suitable media containing one or more cryoprotectants, such as DMSO or FBS to facilitate freezing the cells. In one embodiment the invention provides a hEP cell cryopreserved in a hydrogel comprising hyaluronate. The hydrogel may further comprise gelatin. The hydrogel may further comprise an acrylate such as PEG acrylate. The acrylate may serve as a crosslinker. An example of a suitable media for cryo-preserving the cells in a hydrogel may comprise FBS that is 10% DMSO. The cells may be frozen at −80° C.

In other embodiments the invention provides a composition comprising a cryo-preserved in vitro differentiated progeny of a progenitor cell, such as hEP cell described infra. The composition may comprise at least 1, at least 10, at least 100, at least 1,000, at least 10,000, at least 100,00, at least 1,000,000 viable cryo preserved in vitro differentiated progeny of a progenitor cell. The composition may comprise about 1, about 100, about 1,000, about 10,000, about 100,00, about 1,000,000 viable cryo preserved in vitro differentiated progeny of a progenitor cell. The cryopreserved in vitro differentiated progeny of a progenitor cell may further comprise a hydrogel wherein the in vitro differentiated progeny of a progenitor cell is seeded within the hydrogel. The cryopreserved in vitro differentiated progeny of a progenitor cell may include a suitable media containing one or more cryoprotectants, such as DMSO or FBS to facilitate freezing the cells. In one embodiment the invention provides the in vitro differentiated progeny of an hEP cell cryopreserved in a hydrogel comprising hyaluronate. The hydrogel may further comprise gelatin. The hydrogel may further comprise an acrylate such as PEG acrylate. The acrylate may serve as a crosslinker. An example of a suitable media for cryo-preserving the cells in a hydrogel may comprise FBS that is 10% DMSO. The cells may be frozen at −80° C.

The cryopreserved compositions may be used in research and therapeutic applications. For example a subject in need of cell therapy may be treated with the cryopreserved composition described infra. The composition may be thawed and administer to a subject in need of treatment. The placement of the cells described infra in the hydrogel may facilitate both cropreserving the cell and enhancing transplantation of the cell into a subject.

In some embodiments the invention provides a method of cryo-preserving a cell comprising 1) contacting the cell with a hydrogel, 2) contacting the cell of 1) with a media comprising fetal bovine serum (FBS) and dimethyl sulfoxide (DMSO) and 3) freezing the cell of 2) at −80° C. thereby cryo-preserving the cell.

In some embodiments the invention provides a method of cryo-preserving a cell comprising 1) contacting the cell with a hydrogel, 2) contacting the cell of 1) with a media comprising fetal bovine serum (FBS) and glycerol and 3) freezing the cell of 2) at −80° C. thereby cryo-preserving the cell.

In some embodiments the method described in the previous paragraph is practiced using one or more of the cells described infra. Thus the cell may be a hEP cell or the in vitro differentiated progeny of a hEP cell. The cell may be contacted with the hydrogel before the hydrogel has had a chance to solidify, e.g. the may be contacted with one or more liquid preparations comprising the hydrogel and after contacting the cell with the one or more liquid preparations comprising the hydrogel the hydrogel may be allowed to polymerize. The hydrogel may comprise hyaluronate, gelatin and a crosslinker such as an acrylate or methacrylate, e.g., PEG acrylate. The hyaluronate may be thiolated. The gelatin may be thiolated. (See U.S. Pat. Nos. 7,928,069; 7,981,871). The hydrogel may be seeded with about 100 cells, about 500 cells, about 1,000 cells, about 10,000 cells, about 100,000 cells, about 1,000,000 cells, about 10,000,000 cells. In some embodiments the hydrogel is seeded with about 105-to about 107 cells.

The media used in the method of cryo-preserving cells described infra may comprise any known media and a suitable cryoprotectant. Examples of suitable cryoprotectants include FBS, DMSO, glycerol, glucose and the like. In one embodiment the media is comprised of FBS that is made 10% DMSO. In another embodiment the media consists of FBS that is made 10% DMSO.

General Techniques

Laboratory techniques useful in the practice of this invention can be found in standard textbooks and reviews in cell biology, tissue culture, and embryology. Stem cell biology and manipulation is described in Teratocarcinomas and embryonic stem cells: A practical approach, by E. J. Robertson ed., IRL Press Ltd. 1987; Guide to Techniques in Mouse Development, by P. M. Wasserman et al. eds., Academic Press 1993; and Embryonic Stem Cell Differentiation in Vitro, by M. V. Wiles, Meth. Enzymol. 225:900 1993.

Methods in molecular genetics and genetic engineering are described in Molecular Cloning: A Laboratory Manual, 2.sup.nd Ed., by Sambrook, et al. 1989; Oligonucleotide Synthesis, by M. J. Gait ed. 1984; Animal Cell Culture, by R. I. Freshney, ed. 1987; the series Methods in Enzymology, by Academic Press; Gene Transfer Vectors for Mammalian Cells, by J. M. Miller & M. P. Calos, eds. 1987; Current Protocols in Molecular Biology and Short Protocols in Molecular Biology, 3.sup.rd Edition, by F. M. Ausubel, et al. eds. 1987 & 1995; and Recombinant DNA Methodology II, by R. Wu ed., Academic Press 1995. Reagents, cloning vectors, and kits for genetic manipulation referred to in this disclosure are available from commercial vendors such as BioRad, Stratagene, Invitrogen, and ClonTech. General techniques used in raising antibodies, and the design and execution of immunoassays and immunohistochemistry, are found in the Handbook of Experimental Immunology, by D. M. Weir & C. C. Blackwell eds.; Current Protocols in Immunology, by J. E. Coligan, et al. eds. 1991; and R. Masseyeff, W. H. Albert, and N. A. Staines, eds., Methods of Immunological Analysis, by Weinheim: VCH Verlags GmbH 1993.

Applications

The disclosed methods for the culture of animal cells and tissues are useful in generating brown fat progenitors and differentiated brown fat cells for use in research and therapy. Research uses include the use of the cells in drug screening for agents useful in treating metabolic disorders and therapeutic uses include the use of the cells or progeny thereof in mammalian and human cell therapy, such as, but not limited to, generating human cells useful in treating metabolic disorders such as diabetes and obesity, vascular disorders such as hypertension and atherosclerosis, and Alzheimer's disease in humans and nonhuman animals.

The methods used in the present invention wherein the original pluripotent stem cells are used as master cell banks for the indefinite derivation on an industrial scale of differentiated cell types has commercial advantages in quality control and reproducibility. Of particular utility is the present invention wherein the master cell bank may be genetically modified to allow the resulting somatic cells to escape immune surveillance, and where an intermediate still relatively undifferentiated clonal embryonic progenitor cell type with relatively long telomere length is scaled up as the point of industrial scalability. Also of particular utility are the formulations described herein where the cells of the present invention are differentiated with factors that induce BAT cell differentiation in a hydrogel that has been demonstrated to be safely administered subcutaneously in humans, thereby providing a formulation to produce three-dimensional adipose tissue in vivo.

Drug Screening

The cells of this invention can be used to screen for factors (such as solvents, small molecule drugs, peptides, polynucleotides) or environmental conditions (such as culture conditions or manipulation) that affect the characteristics of both brown fat preadipocyte precursors and mature brown fat cells. In one example, pluripotent stem cells (undifferentiated or initiated into the differentiation paradigm) are used to screen factors that promote maturation into brown fat cells, or promote proliferation and maintenance of brown fat cells in long-term culture. For example, candidate maturation factors or growth factors are tested by adding them to cells in different wells, and then determining any phenotypic change that results, according to desirable criteria for further culture and use of the cells. This can lead to improved derivation and culture methods not only for pluripotent stem cell-derived brown fat cells, but for brown fat cell progenitors isolated from fetal or adult tissue.

Another example is the use of brown fat cell progenitors or differentiated brown fat cells of the present invention are used to measure the effect of small molecule drugs that have the potential to affect brown fat cell activity in their role of metabolizing lipoproteins, secreting adipokines, or heat regulation. To this end, the cells can be combined with test compounds in vitro, and the effect of the compound on gene expression or protein synthesis can be determined. The screening can also be done in vivo by measuring the effect of the compound on the behavior of the cells in an animal model.

Other screening methods of this invention relate to the testing of pharmaceutical compounds or a potential effect on brown fat cell growth, development, or toxicity. This type of screening is appropriate not only when the compound is designed to have a pharmacological effect on brown fat cells themselves, but also to test for brown fat cell-related side-effects of compounds designed for a primary pharmacological effect elsewhere. The reader is referred generally to the standard textbook "In vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [3H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

In certain embodiments of the invention, the differentiated progeny of hEP cells described infra, may be used as "feeder cells" to support the growth of other cell types, including pluripotent stem cells. The use of the differentiated progeny of hEP cells of the present invention as feeder cells alleviates the potential risk of transmitting pathogens from feeder cells derived from other mammalian sources to the target cells. The feeder cells may be inactivated, for example, by gamma ray irradiation or by treatment with mitomycin C, to limit replication and then co-cultured with the pluripotent stem cells.

In certain embodiments of the invention, the extracellular matrix (ECM) of the differentiated progeny of hEP cell disclosed infra, may be used to support less differentiated cells (see Stojkovic, et al., Stem Cells (2005) 23(3):306-14). Certain cell types that normally require a feeder layer can be supported in feeder-free culture on a matrix (Rosier, et al., Dev Dyn. (2004) 229(2):259-74). The matrix can be deposited by pre-culturing and lysing a matrix-forming cell line (see WO 99/20741), such as the STO mouse fibroblast line (ATCC Accession No. CRL-1503), or human placental fibroblasts.

In certain embodiments of the invention, the conditioned media of differentiated progeny of hEP cells may be collected, pooled, filtered and stored as conditioned medium. This conditioned medium may be formulated and used for research and therapy. The use of conditioned medium of cell cultures described infra may be advantageous in reducing the potential risk of exposing cultured cells to non-human animal pathogens derived from other mammalian sources (i.e. xenogeneic free).

In another embodiment of the invention, single cell-derived and oligoclonal cell-derived cells and their differentiated progeny described infra may be used as a means to identify and characterize genes that are transcriptionally activated or repressed as the cells undergo differentiation. For example, libraries of gene trap single cell-derived or oligoclonal cell-derived cells and/or their differentiated progeny may be made by methods of this invention, and assayed to detect changes in the level of expression of the gene trap markers as the cells differentiate in vitro and in vivo. The methods for making gene trap cells and for detecting changes in the expression of the gene trap markers as the cells differentiate are reviewed in Durick, et al. (Genome Res. (1999) 9:1019-25). The vectors and methods useful for making gene trap cells and for detecting changes in the expression of the gene trap markers as the cells differentiate are also described in U.S. Pat. No. 5,922,601 (Baetscher, et al.), U.S. Pat. No. 6,248,934 (Tessier-Lavigne) and in U.S. patent publication No. 2004/0219563 (West, et al.). Methods for genetically modifying cells, inducing their differentiation in vitro, and using them to generate chimeric or nuclear-transfer cloned embryos and cloned mice are developed and known in the art. To facilitate the identification of genes and the characterization of their physiological activities, large libraries of gene trap cells having gene trap DNA markers randomly inserted in their genomes may be prepared. Efficient methods have been developed to screen and detect changes in the level of expression of the gene trap markers as the cells differentiate in vitro or in vivo. In vivo methods for inducing single cell-derived or oligoclonal cell-derived cells or their differentiated progeny to differentiate further include injecting one or more cells into a blastocyst to form a chimeric embryo that is allowed to develop; fusing a stem cell with an enucleated oocyte to form a nuclear transfer unit (NTU), and culturing the NTU under conditions that result in generation of an embryo that is allowed to develop; and implanting one or more clonogenic differentiated cells into an immune-compromised or a histocompatible host animal (e.g., a SCID mouse, or a syngeneic nuclear donor) and allowing teratomas comprising differentiated cells to form. In vitro methods for inducing single cell-derived or oligoclonal cell-derived cells to differentiate further include culturing the cells in a monolayer, in suspension, or in three-dimensional matrices, alone or in co-culture with cells of a different type, and exposing them to one of many combinations of chemical, biological, and physical agents, including co-culture with one or more different types of cells, that are known to capable of induce or allow differentiation.

In another embodiment of the invention, cell types that do not proliferate well under any known cell culture conditions may be induced to proliferate such that they can be isolated clonally or oligoclonally according to the methods of this invention through the regulated expression of factors that overcome inhibition of the cell cycle, such as regulated expression of SV40 virus large T-antigen (Tag), or regulated E1a and/or E1b, or papillomavirus E6 and/or E7, or CDK4 (see, e.g., U.S. patent application Ser. No. 11/604,047 filed on Nov. 21, 2006 and titled "Methods to Accelerate the Isolation of Novel Cell Strains from Pluripotent Stem Cells and Cells Obtained Thereby", incorporated herein by reference).

In another embodiment of the invention, the factors that override cell cycle arrest may be fused with additional proteins or protein domains and delivered to the cells. For example, factors that override cell cycle arrest may be joined to a protein transduction domain (PTD). Protein transduction domains, covalently or non-covalently linked to factors that override cell cycle arrest, allow the translocation of said factors across the cell membranes so the protein may ultimately reach the nuclear compartments of the cells. PTDs that may be fused with factors that override cell cycle arrest include the PTD of the HIV transactivating protein (TAT) (Tat 47-57) (Schwarze and Dowdy, 2000 *Trends Pharmacol. Sci.* 21: 45-48; Krosl, et al. 2003 *Nature Medicine* (9): 1428-1432). For the HIV TAT protein, the amino acid sequence conferring membrane translocation activity corresponds to residues 47-57 (Ho et al., 2001, Cancer Research 61: 473-477; Vives et al., 1997, *J. Biol. Chem.* 272: 16010-16017). These residues alone can confer protein translocation activity.

BAT Cell Progenitors and MT Cells in Clinical Therapy

This invention also provides for the use of BAT precursor and fully differentiated BAT cells and their derivatives to retain or restore normal metabolism in a patient in need of such therapy. Any condition leading to impairment of fat, lipoprotein, blood pressure, or glucose metabolism may be considered. Included are conditions commonly associated with metabolic syndrome X. The cells of the invention can also be considered for treatment of Type I diabetes, wherein betatrophin-secreting cells are injected into the pancreas. Also contemplated is the use of the cells of this invention for the management of obesity and coronary disease.

In certain embodiments of the invention, single cell-derived and oligoclonal cell-derived cells and their differentiated progeny as described infra are utilized in the treatment of disorders relating to cell biology, adipocyte differentiation, and lipoprotein metabolism. For example the hEP cells and their differentiated progeny may be used to generate cDNA libraries which in turn could be used to study gene expression in developing tissue, such as fat, including brown fat cells expressing critical adipokines such as betatrophin or adiponectin and for studying the inherited expression levels of IL13RA2 as a risk factor for obesity and Type II diabetes. The hEP cells and their differentiated progeny can be used in drug screening. For example the cell, such as a differentiated progeny of hEP cell could be contacted with a test drug or compound and analyzed for toxicity by examining the cells under a microscope and observing their morphology or by studying their growth or survival in culture. The cells may also be screened for gene expression to determine the effects of the drug, in particular, for inducing the browning of fat by assaying for UCP1, ADIPOQ or C19ORF80 expression. For example, a comparison could be made between a differentiated progeny of hEP cell that has been contacted with the test drug or compound compared with the same differentiated progeny cell that has not been so contacted.

The differentiated progeny of hEP cells may be used to screen for the effects of growth factors, hormones, cytokines, mitogens and the like to determine the effects of these test compounds on the differentiation status of the differentiated progeny of the hEP cells.

In certain embodiments of the invention, the differentiated progeny of the hEP cells may be introduced into the tissues in which they normally reside in order to exhibit therapeutic utility or alternatively to coax the cells to differentiate further. In certain embodiments of the invention, the differentiated progeny of the hEP cells described infra, are utilized in inducing the differentiation of other pluripotent or multipotent stem cells. Cell-cell induction is a common means of directing differentiation in the early embryo. Cell types useful in the induction may mimic induction well known in the art to occur naturally in normal embryonic development.

Many potentially medically-useful cell types are influenced by inductive signals during normal embryonic development, including spinal cord neurons, cardiac cells, pancreatic beta cells, and definitive hematopoietic cells. Differentiated progeny of hEP cells may be cultured in a variety of in vitro, or in vivo culture conditions to induce the differentiation of other pluripotent stem cells to become desired cell or tissue types. Induction may be carried out in a variety of methods that juxtapose the inducer cell with the target cell. By way of nonlimiting examples, the inducer cells may be plated in tissue culture and treated with mitomycin C or radiation to prevent the cells from replicating further. The target cells are then plated on top of the mitotically-inactivated inducer cells. Alternatively, the differentiated progeny of hEP cells may be cultured on a removable membrane from a larger culture of cells or from an original single cell-derived colony and the target cells may be plated on top of the inducer cells or a separate membrane covered with target cells may be juxtaposed so as to sandwich the two cell layers in direct contact. The resulting bilayer of cells may be cultured in vitro, transplanted into a SPF avian egg, or cultured in conditions to allow growth in three dimensions while being provided vascular support (see, for example, international patent publication number WO/2005/068610, published Jul. 28, 2005, the disclosure of which is hereby incorporated by reference). The inducer cells may also be from a source of differentiated progeny of hEP cells, in which a suicide construct has been introduced such that the inducer cells can be removed at will. The cells of the present invention are optimally formulated for therapeutic use when combined with a biocompatible matrix such as HyStem-C (Renevia). BAT cells are prepared by growing in cell culture on tissue culture vessel surfaces or beads in a slurry, or alternatively on HyStem-C beads wherein they are frozen for use at the point of care. During surgery, the BAT cells are thawed, mixed with matrix components, and the cell-loaded matrix is injected into the area of desired placement.

BAT cells made pursuant to the instant invention may also be formulated with patient-specific adipose stromal vascular fraction such as that obtained in abdominal liposuction to provide cellular components of normal adipose tissue vasculature including vascular endothelial, and perivascular cells to aid in the vascularization and survival of the graft. In addition, the graft may be augmented with pluripotent stem cell-derived vascular progenitors expressing ITLN1 and ITLN2 such as that previously described (Compositions and methods relating to clonal progenitor cell lines, WO 2013036969 A1). As always, the ultimate responsibility for patient selection, mode of administration, and choice of support structures and surgical options is the responsibility of the managing clinician.

For purposes of commercial distribution, BAT cells of this invention are typically supplied in the form of a pharmaceutical composition, comprising an isotonic excipient prepared under sufficiently sterile conditions for human administration. For general principles in medicinal formulation of cell compositions, the reader is referred to Cell Therapy: Stem Cell Transplantation, Gene Therapy, and Cellular Immunotherapy, by G. Morstyn & W. Sheridan, eds, Cambridge University Press, 1996.

The composition may also contain a matrix for keeping the BAT cells in place during the first few months following therapy. Biocompatible matrices such as HyStem (BioTime) allow the mixture of cells with matrix, the injection of said cells and matrix in a liquid form, with polymerization forming in vivo. Besides HyStem, other possible matrixes include bioresorbable polymer fleece matrices (Rudert, et al., Cells Tissues Organs 167:95, 2000); hyaluronan derivatives (Grigolo, et al., Biomaterials 22:2417, 2001); sponge made from poly(L-lactideepsilon-caprolactone) (Honda et al., J. Oral Maxillofac. Surg. 58:767, 2000), and collagen-fibrin matrices (Clin. Exp. Rheumatol. 18:13, 2000).

The cells of the present invention may be transplanted to increase insulin sensitivity, to decrease total body fat, or to decrease coronary or stroke disease risk by transplanting the cells at a dosage, by way of nonlimiting example, in humans, cells may be administered in the intercostal region where BAT cells normally reside at birth and in the vicinity of sympathetic innervation of such BAT cells at a concentration of $2.5 \times 10^5$ cells/ml to $1.0 \times 10^8$ cells/ml in HyStem-C (BioTime, Inc. Alameda, CA), preferably $1.0-3.0 \times 10^7$ cells/ml, or at these concentrations in other matrices useful in promoting cell engraftment. The total dosage of said cells administered will vary based on the extent of the loss of BAT tissue and the severity of the disease. For example, patients with morbid obesity may require cells administered at the upper ranges described herein based on the judgement of the patient's physician. Individual doses will vary from $10-100 \times 10^6$ cells per injection (0.3 mL-10.0 ml per injection depending on concentration of cells). Effectiveness of the therapy can be assessed by monitoring serum adiponectin and/or betatrophin by ELISA or other means known in the art before and after treatment, or by PET scanning following administration in vivo of 2-[18F]fluoro-2-deoxyglucose (FDG) to assess uptake into BAT tissue.

The site of engraftment may vary, but by way of example, the cells may be injected subcutaneously at the normal site of brown fat cells in humans such as in the interscapular region of the back. The cells may or may not also be genetically-modified, with modifications to increase C19orf80 expression, such as those that down-regulate the insulin receptor gene, or allow the inducible apoptosis of the engrafted cells, or modification to promote the allogeneic histocompatibility of said cells.

In the prevention of atherosclerosis, such as coronary artery disease, the BAT cells of the present invention, formulated in HyStem-C at comparable concentrations disclosed herein, may be injected into the perivascular space surrounding arteries at risk for or displaying atherosclerosis. The presence of the BAT cells of the present invention will provide a therapeutic effect to the patient through the unique lipoprotein metabolism displayed by the cells as well as the secretion of adiponectin.

In the management of Type I and Type II diabetes, cells of the present invention, including without limitation, human ES cell-derived clonal embryonic progenitor cell lines expressing a pattern of genes conferring immunotolerance as described herein and a pattern of gene expression comparable to NP110SM and expressing relatively high levels of C19ORF80 in the differentiated state may be injected directly into the pancreas to induce beta cell proliferation. When said cells also overexpress localized immunosuppressive agents such as PD-L1, such cells can also be used to halt the immune-mediated destruction of pancreatic beta cells in Type I diabetes.

The composition or device is optionally packaged in a suitable container with written instructions for a desired purpose, such as the reconstruction of BAT tissue for the management of obesity, diabetes, and coronary disease.

It is understood that certain adaptations of the invention described in this disclosure as a matter of routine optimization for those skilled in the art, and can be implemented without departing from the spirit of the invention, or the scope of the appended claims. In another embodiment of the invention, the hEP cell line such as an hEP cell line capable of brown fat differentiation may be immortalized or have its cell lifespan extended by the permanent or temporary expression of the catalytic component of telomerase (TERT).

In another embodiment of the invention, the single cell-derived and oligoclonal cell-derived cells or their differentiated progeny may be used to generate ligands using phage display technology (see U.S. application No. 60/685,758, filed May 27, 2005, and PCT US2006/020552).

The expression of genes of the cells of this invention may be determined. Measurement of the gene expression levels may be performed by any known methods in the art, including but not limited to, microarray gene expression analysis, bead array gene expression analysis and Northern analysis. The gene expression levels may be represented as relative expression normalized to the ADPRT (Accession number NM_001618.2), GAPDH (Accession number NM_002046.2), or other housekeeping genes known in the art. The gene expression data may also be normalized by a median of medians method. In this method, each array gives a different total intensity. Using the median value is a robust way of comparing cell lines (arrays) in an experiment. As an example, the median was found for each cell line and then the median of those medians became the value for normalization. The signal from the each cell line was made relative to each of the other cell lines. Based on the gene expression levels, one would expect the expression of the corresponding proteins by the cells of the invention.

In another embodiment of the invention, the single cell-derived or oligoclonal cell-derived cells or their differentiated progeny described infra may express unique patterns of CD antigen gene expression, which are cell surface antigens. The differential expression of CD antigens on the cell surface may be useful as a tool, for example, for sorting cells using commercially available antibodies, based upon which CD antigens are expressed by the cells. The expression profiles of CD antigens of some cells of this invention are shown in West et al., 2008, Regen Med vol. 3(3) pp. 287-308, incorporated herein by reference, including supplemental information. There are several CD antigens that are expressed in the relative more differentiated cells of this invention, but are not expressed in ES cells (or in some cases at markedly reduced levels). The antigens that fall into this category include: CD73, CD97, CD140B, CD151, CD172A, CD230, CD280, CDw210b. These antigens may be useful in a negative selection strategy to grow ES cells or alternatively to isolate certain cells described infra.

In another embodiment of the invention, the single cell-derived and oligoclonal cell-derived cells or their differentiated progeny, may be injected into mice to raise antibodies to differentiation antigens. Antibodies to differentiation antigens would be useful for both identifying the cells to document the purity of populations for cell therapies, for research in cell differentiation, as well as for documenting the presence and fate of the cells following transplantation. In general, the techniques for raising antibodies are well known in the art.

In another embodiment of the invention, the single cell-derived and oligoclonal cell-derived cells or the differentiated progeny thereof may be used for the purpose of generating increased quantities of diverse cell types with less pluripotentiality than the original stem cell type, but not yet fully differentiated cells. mRNA or miRNA can then be prepared from these cell lines and microarrays of their relative gene expression can be performed as described herein.

In another embodiment of the invention, the single cell-derived and oligoclonal cell-derived cells or their differentiated progeny may be used in animal transplant models, e.g. transplanting escalating doses of the cells with or without other molecules, such as ECM components, to determine whether the cells proliferate after transplantation, where they migrate to, and their long-term differentiated fate in safety studies.

In another embodiment of the invention, the cells of the present invention when induced to differentiate into BAT cell components expressing betatrophin and adiponectin into the medium may be used as a means of manufacturing said proteins for research and therapeutic use using the spent media or using methods described herein for the mild urea extraction of secreted proteins or simply collecting spent media and purifying the proteins to varying levels of purity.

In another embodiment of the invention, the single cell-derived and oligoclonal cell-derived cells generated according to the methods of the present invention are useful for harvesting mRNA, microRNA, and cDNA from either single cells or a small number of cells (i.e., clones) to generate a database of gene expression information. This database allows researchers to identify the identity of cell types by searching for which cell types in the database express or do not express genes at comparable levels of the cell type or cell types under investigation. For example, the relative expression of mRNA may be determined using microarray analysis as is well known in the art. The relative values may be imported into a software program such as Microsoft Excel and gene expression values from the different cell lines normalized using various techniques well known in the art such as mean, mode, median, and quantile normalization. Hierarchical clustering with the single linkage method may be performed with the software such as *The R Project for Statistical Computing* as is well known in the art. An example of such documentation may be found online. A hierarchical clustering analysis can then be performed as is well known in the art. These software programs perform a hierarchical cluster analysis using a group of dissimilarities for the number of objects being clustered. At first, each object is put in its own cluster, then iteratively, each similar cluster is joined until there is one cluster. Distances between clusters are computed by Lance-Williams dissimilarity update formula (Becker, R. A., Chambers, J. M. and Wilks, A. R. (1988) The New S Language. Wadsworth & Brooks/Cole. (S version.); Everitt, B. (1974). Cluster Analysis. London: Heinemann Educ. Books). Typically the vertical axis of the dendograms displays the extent of similarity of the gene expression profiles of the cell clones. That is, the farther down they branch apart, the more similar they are. The vertical axis is a set of n−1 non-decreasing real values. The clustering height is the value of the criterion associated with the clustering method for the particular agglomeration. In order to determine if a new cell line is identical to existing cell lines, two types of replicates are performed: biological and technical replicates. Biological replicates require that new cell lines be grown, mRNA harvested, and then the analysis compared. Technical replicates, on the other hand, analyze the same RNA twice. A line cutoff is then drawn just above where the replicates branch such that cells branching below the cutoff line are considered the same cell type. Another source of data for the database described above may be microRNA profiles of the single cell-derived and oligoclonal cell-derived cells or their differentiated progeny described infra. MicroRNAs (miRNA) are endogenous RNAs of ~22 nucleotides that play important regulatory roles in animals & plants by targeting mRNAs for cleavage or translational repression. More than 700 miRNAs have been identified across species. Their expression levels vary among species and tissues. Low abundant miRNAs have been difficult to detect based on current technologies such as cloning, Northern hybridization, and the modified Invader® assay. In the present invention, an alternative approach using a new real-time quantitation method termed looped-primer RT-PCR was used for accurate and sensitive detection of miRNAs as well as other non-coding RNA (ncRNA) molecules present in human embryonic stem cells and in cell lines differentiated from human embryonic stem cells.

In another embodiment of the invention, gene expression analysis may be used to identify the developmental pathways and cell types for in vitro differentiated hES cells. Gene expression analysis of single cells or a small number of cells from human or nonhuman embryonic or fetal tissues provides another means to generate a database of unique gene expression profiles for distinct populations of cells at different stages of differentiation. Gene expression analysis on single cells isolated from specific tissues may be performed as previously described by Kurimoto et al., Nucleic Acids Research (2006) Vol. 34, No. 5, e42. Thus, cellular miRNA profiles on their own or in conjunction with gene expression profiles, immunocytochemistry, and proteomics provide molecular signatures that can be used to identify the tissue and developmental stage of differentiating cell lines. This technique illustrates that the database may be used to accurately identify cell types and distinguish them from other cell types. The cells of the present invention are also useful in providing a subset of gene expression markers that are expressed at relatively high levels in some cell lines while not be expressed at all in other cell lines as opposed to genes expressed in all cell lines but at different levels of expression. This subset of "all-or none" markers can be easily identified by comparing the levels of expression as measured for instance through the use of oligonucleotide probes or other means know in the art, and comparing the level of a gene's expression in one line compared to all the other lines of the present invention. Those genes that are expressed at relatively high levels in a subset of lines, and not at all in other lines, are used to generate a short list of gene expression markers. When applied to the cells and gene expression data described herein, where negative expression in Illumina 1 is <120 RFU and positive expression is >140 RFU.

Oil Red-O Staining

Oil Red-O staining is used to identify adipogenic differentiation. Oil Red-O was purchased from Sigma-Aldrich Cat #01391-500 ML. Cells, cells attached to cell culture vessels, or cell/matrix constructs such as HyStem beads containing cells are fixed with 4% paraformaldehyde for 30 minutes. Cells or the above-mentioned constructs are then rinsed with distilled water and stained for 10 minutes at room temperature with filtered working solution of Oil Red-O solution (3 parts 0.5% stock aqueous Oil Red-O diluted with 2 Parts $H_2O$), then filtered with Whatman paper. Stock solution of Oil Red-O is 0.5% (w/v) Oil Red-O in isopropanol. The cells or constructs are then rinsed with H2O at least 4 times before photography to document the percentage of cells displaying prominent cytoplasmic red lipid droplets.

Methods for Analyzing Gene Expression in Embryonic Progenitor Cells and Their Differentiated Progeny In some embodiments of the invention, described infra, the following methods may be useful in the analysis of gene expression in embryonic progenitor cells and their differentiated progeny, e.g., their in vitro differentiated progeny.

Isolation of RNA

RNA is prepared from cell lysates using the Rneasy mini kits (Qiagen) according to the manufacturer's instructions. Briefly, cell cultures are rinsed in PBS, then lysed in a minimal volume of the RLT lysis buffer. After incubation on ice, the cell debris is removed by centrifugation and the lysate is mixed with RLT buffer, after which ethanol is added to the mixture. The combined mixture is then loaded onto the Rneasy spin column and centrifuged; the loaded column is then washed and the purified RNA is released from the column with a minimal volume of DEPC-treated water (typically 100 µl or less). The concentration of RNA in the final eluate is determined by absorbance at 260 nm.

cDNA Synthesis cDNA synthesis is performed using the SuperScript First Strand cDNA kit (InVitrogen; Carlsbad, CA). Briefly, 1 µg of purified RNA is heat denatured in the presence of random hexamers. After cooling, the first strand reaction is completed using SuperSript reverse transcriptase enzyme and associated reagents from the kit. The resulting product is further purified using QlAquick PCR Purification kits (Qiagen) according to the manufacturer's instructions. Briefly, PB buffer is added to the first strand cDNA reaction products, then the mixture is loaded onto the QlAquick spin column and centrifuged. The column is washed with PE buffer and the purified cDNA is eluted from the column using 50 µl of water.

Quantitative Real-Time PCR (qRT-PCR) Analysis

Samples for testing (template) were prepared in standard Optical 96-well reaction plates (Applied Biosystems Carlsbad, CA, PN 4306737) consisting of 30 ng of RNA equivalent of cDNA, 0.8 uM per gene-specific custom oligonucleotide primer set (Life Technologies, Carlsbad, CA or Eurofins Genomics, Huntsville, AL), ultra-pure distilled water (Life Technologies Cat. #10977015), diluted 1:1 with 12.5 ul of Power SYBR Green PCR Master Mix (Applied Biosystems Carlsbad, CA, Cat. #4367659) incorporating AmpliTaq Gold DNA polymerase in a total reaction volume of 25 ul. Real-Time qPCR was run using Applied Biosystems 7500 Real-Time PCR System employing SDS2.0.5 software. Amplification conditions were set at 50° C. for 2 min. (stage 1), 95° C. for 10 min. (stage 2), 40 cycles of 95° C. for 15 sec then 60° C. for 1 min (stage 3), with a dissociation stage (stage 4) at 95° C. for 15 sec, 60° C. for 1 min, and 95° C. for 15 sec. Ct values of amplicons were normalized to the average Ct value of GAPDH.

qPCR Primers qPCR primer pairs are synthesized for each target gene. Briefly, primer pairs for a target gene are designed to amplify only the target mRNA sequence and optimally have annealing temperatures for their target sequences that lie in the range of 65-80'C and unique amplification products in the size range of 80-500 bp. Primer pairs are supplied at working concentrations (10 uM) to BioTrove, Inc. (Woburn, MA) for production of a custom qPCR Open Array plate. OpenArray plates are designed to accommodate 56-336 primer pairs and the final manufactured plate with dried down primer pairs is provided to the service provider. Purified cDNA reaction products and SYBR green master mix are loaded into individual wells of the OpenArray plate using OpenArray autolader device (BioTrove). The plate is sealed and the qPCR and loaded into the NT Imager/Cycler device (BioTrove) for amplification. Ct values for each sample are calculated using the OpenArray application software.

```
Primers used:
GAPDH (NM_002046.4)
f.
                                        [SEQ ID NO: 1]
GGCCTCCAAGGAGTAAGACC r.
                                        [SEQ ID NO: 2]
AGGGGTCTACATGGCAACTG (147 bp)

UCP1 (NM_021833.4)
f.
                                        [SEQ ID NO: 3]
AGGCGTGAAGAGCAAGGGAAA r.
                                        [SEQ ID NO: 4]
CCCCATCTTCACTCAGAGACTG (89 bp)

FABP4 (NM_001442.2)
f.
                                        [SEQ ID NO: 5]
GACCTGGACTGAAGTTCGCA 5- r.
                                        [SEQ ID NO: 6]
ACTTGCTTGCTAAATCAGGGA (94 bp)

LOC55908 (TD26, betatrophin, C19orf80)
(NM_018687.5)
f.
                                        [SEQ ID NO: 7]
CTACGGGACAGCGTGCAGC r.
                                        [SEQ ID NO: 8]
CAGCATGATTGGTCCTCAGTTCC (257 bp)
-This particular primer pair is referred to as
1422

LOC55908 (TD26, betatrophin, C19orf80)
(NM_018687.5)
f.
                                        [SEQ ID NO: 9]
GCTGACAAAGGCCAGGAACAGC r.
                                        [SEQ ID NO: 10]
ACCTCCCCCAGCACCTCAGC (180 bp)
-This particular primer pair is referred to as
1424

LOC55908 (TD26, betatrophin, C19orf80)
(NM_018687.5)
f.
                                        [SEQ ID NO: 11]
GCAAGCCTGTTGGAGACTCAG r.
                                        [SEQ ID NO: 12]
CTGTCCCGTAGCACCTTCT (110 bp)
-This particular primer pair is referred to as
1085
```

Secreted Protein Isolation Protocol 1—Conditioned Medium

Cells were grown in either their normal propagation medium (West et al., 2008, *Regen Med* vol. 3(3) pp. 287-308) or the differentiation conditions described herein. To obtain conditioned medium on a smaller scale (typically 1-2 L or less), the cells were grown in monolayer cultures in T150, T175 or T225 flasks (Corning or BD Falcon) in a 374C incubator with 10% CO2 atmosphere. For larger volume medium collections, the cells were typically grown either in 2 L roller bottles, on microcarrier suspensions (porous such as Cytodex varieties from Sigma-Aldrich, St. Louis, MO, or non-porous such as from SoloHill Engineering, Ann Arbor, MI) in spinner flasks or other bioreactors, or in hollow fiber cartridge bioreactors (GE Healthcare, Piscataway, NJ). Prior to conditioned medium collection, the cultures were rinsed twice with PBS and then incubated for 2 hours at 37° C. in the presence of serum-free medium wherein the medium is the same basal medium as described herein for the propagation or differentiation of the cells, in order to remove fetal serum proteins. The serum-free medium was then removed and replaced with fresh medium, followed by continued as described herein at 374C for 24-48 hours.

The culture-conditioned medium was then collected by separation from the cell-bound vessel surface or matrix (e.g., by pouring off directly or after sedimentation) and processed further for secreted protein concentration, enrichment or purification. As deemed appropriate for the collection volume, the culture medium was first centrifuged at 500 to 10,000×g to remove residual cells and cellular debris in 15 or 50 ml centrifuge tubes or 250 ml bottles. It was then passed through successive 1 µm or 0.45 µm and 0.2 µm filter units (Corning) to remove additional debris, and then concentrated using 10,000 MW cutoff ultrafiltration in a stirred cell or Centricon centrifuge filter (Amicon-Millipore) for smaller volumes, or using a tangential flow ultrafiltration unit (Amicon-Millipore) for larger volumes. The retained protein concentrate was then dialyzed into an appropriate buffer for subsequent purification of specific proteins, and further purified using a combination of isoelectric focusing, size exclusion chromatography, ion exchange chromatography, hydrophobic or reverse phase chromatography, antibody affinity chromatography or other well-known methods appropriate for the specific proteins. During the various steps in the purification process, collection fractions were tested for the presence and quantity of the specific secreted protein by ELISA (e.g., using BMP-2 or BMP-7 ELISA kits from R&D Systems, Minneapolis, MN). The purified proteins were then kept in solution or lyophilized and then stored at 4 or minus 20-80C.

Secreted Protein Isolation Protocol 2—Urea-Mediated Protein Extraction

In the case of some secreted proteins, interactions with the cell or ECM components may reduce the simple diffusion of factors into the medium as described above in Secreted Protein Isolation Protocol 1. A simple comparison of the yield in the two protocols will suffice to determine which protocol provides the highest yield of the desired factors. In the case of Secreted Protein Isolation Protocol 2, a low concentration of urea is added to facilitate the removal of factors. In the case of the examples provided, all urea extractions were performed two days subsequent to feeding. On the second day, cell monolayers in T-150 cell culture flasks were rinsed twice with CMF-PBS and then incubated for two hours at 379C in the presence of serum-free medium. The rinse with CMF-PBS and the incubation in serum-free medium together aid in the removal of fetal serum proteins from the surface of the cells. The serum-free medium was then removed and 10 ml/T150 of freshly made 200 mM urea in CMF-PBS was added. The flasks were then placed on a rocker at 37° C. for 6.0 hours. The urea solution was then removed and immediately frozen at −70° C.

Extracellular Matrix Isolation Protocol—DOC-Mediated Preparation

Extracellular matrix proteins can be extracted using the method of Hedman et al, 1979 (Isolation of the pericellular matrix of human fibroblast cultures. J. Cell Biol. 81: 83-91). Cell layers are rinsed three times with CMF-PBS buffer at ambient temperature and then washed with 30 mL of 0.5% sodium deoxycholate (DOC), 1 mM phenylmethylsulfonylfluride (PMSF, from 0.4M solution in EtOH), CMF-PBS buffer 3×10 min. on ice while on a rocking platform. The flasks were then washed in the same manner with 2 mM Tris-HCl, pH 8.0 and 1 mM PMSF 3×5 min. The protein remaining attached to the flask was then removed in 2 mL of gel loading buffer with a rubber policeman.

Screening of Secreted or Extracellular Matrix Proteins for Biological Activity

The cell lines and their differentiated progeny of the present invention are also useful as a means of screening diverse embryonic secretomes for varied biological activities. The cell lines of the present invention cultured at 18-21 doublings of clonal expansion express a wide array of secreted soluble and extracellular matrix genes (see US Patent Application Publication 2010/0184033 entitled "METHODS TO ACCELERATE THE ISOLATION OF NOVEL CELL STRAINS FROM PLURIPOTENT STEM CELLS AND CELLS OBTAINED THEREBY" filed on Jul. 16, 2009, incorporated herein by reference). At 21 or more doublings of clonal expansion, the cells of the present invention differentially express secreted soluble and extracellular matrix genes. These proteins, proteoglycans, cytokines, and growth factors may be harvested from the embryonic progenitor cell lines or their differentiated progeny of the present invention by various techniques known in the art including those described infra. These pools of secreted and extracellular matrix proteins may be further purified or used as mixtures of factors and used in varied in vitro or in vivo assays of biological activity as is known in the art. The secreted proteins could be used as an antigen to generate antibodies such as polyclonal or monoclonal antibodies. The antibodies in turn can be used to isolate the secreted protein. As an example, differentiated progeny expressing adipokine genes such as ADIPOQ or the gene for C19orf80 (betatrophin) could be used to isolate the adipokines from the cells or to generate antibodies specific to them. The adipokines could be used for research or therapy. The antibodies could be used to purify the adipokines from the cells described infra or other cells expressing them.

Routine Culture of the Cell Lines

Cells were thawed, cultured, and routinely dissociated with 0.25% trypsin diluted 1:3 with Ca Mg free PBS to single cells and plated onto gelatin-coated tissue culture plates. The cells lines were maintained in, and all subsequent experiments with the exception of HyStem-bead experiments, were carried out at 37° C. in a humidified atmosphere of 10% $CO_2$ and 5% $O_2$. The culture medium for said expansion of the lines NP88 SM, NP111 SM, NPCC SM19, NPCC SM23, NPCC SM28, NPCC SM31, NPCC SM36, NP92 SM, NP91 SM, NP93 SM, NP95 SM, and NP113 SM was MCDB131 medium with growth supplements: 5% fetal calf serum, 0.5 ng/ml EGF, 2.0 ng/ml basic FGF, and 5.0 µg/ml insulin. The culture medium for the expansion of the lines SK1 and ESI-004-EP SK8, was basal MCDB120 medium containing glutamax 2 mM, and pen/strep 10,000 U/ml, 5% FCS, 50 µg/mL bovine fetuin, 10 ng/mL recombinant EGF, 1.0 ng/mL recombinant bFGF, 10 µg/mL recombinant Insulin, 0.4 ug/mL dexamethasone, and 2.0 mM GlutaMAX-1 supplement. The cell lines NP77 EN, NP78 EN, NP80 EN and NP95 EN were cultured in Promocell MV2 endothelial cell culture media.

Adipogenesis Protocol 1

HyStem-C matrix (BioTime, Alameda, CA) is prepared as follows. The HyStem component (10 mg of thiol-modified hyaluronan) is dissolved in 1.0 ml of degassed deionized water for approximately 20 min to prepare a 1% w/v solution. The Gelin-S® component (10 mg of thiol modified gelatin (BioTime)) is dissolved in 1.0 ml of degassed deionized water to prepare a 1% w/v solution, and polyethylene glycol diacrylate (10 mg of PEGDA) is dissolved in 0.5 ml of degassed deionized water to prepare a 2% w/v solution. Then, HyStem (1 ml, 1% w/v) is mixed with Gelin-S (1 ml, 1% w/v) immediately before use. Pelleted cells of the present invention are resuspended in the recently prepared HyStem:Gelin-S (1:1 v/v) mix described above. Upon the addition of the PEGDA cross-linker, the cell suspension, at a final concentration of $2.0 \times 10^7$ cells/ml is aliquoted (25 µl/aliquot) into six-well plates (Corning® 3516; VWR, PA, USA) after partial gelation. Following complete gelation (20 min), Differentiation Medium is added to each well. Differentiation medium is high glucose DMEM (CellGro Cat. No. 15-013-CV) with Pyruvate, 1 mM (Gibco Cat. 11360), Pen:Strep 100U/ml:100 ug/ml (Gibco Cat. No. 504284), Glutamax 2 mM (Gibco Cat. No. 35050), Dexamethasone 0.1 uM (Sigma, St. Louis, MO, Cat. No.D1756-100), L-Proline 0.35 mM (Sigma Cat. No. D49752), 2-phospho-L-Ascorbic Acid 0.17 mM (Sigma, Cat. No. 49792, Fluka), and ITS Premix (BD, Franklin Lakes, NJ, sterile Cat. No. 47743-628) with a final concentration 6.25 ug/ml insulin, 6.25 ug/ml transferrin, 6.25 ng/ml selenious acid, serum albumin 1.25 mg/ml, 5.35 ug/ml linoleic acid. The Differentiation medium is supplemented with 1.0 µM rosiglitazone, and 2.0 nM triiodothyronine (T3) with or without 10 ng/ml BMP4. Plates were then placed in a humidified incubator at 37° C. with ambient $O_2$ and 10% $CO_2$, and the cells were fed three-times weekly. For the last 4 hours prior to use, 10 µM CL-316,243 was added to the culture medium. At the desired time point, hydrogel constructs were either fixed and processed for immunohistochemical analysis or lysed using RLT (Qiagen, CA, USA) with 1% beta-mercaptoethanol for total RNA to analyze transcript expression using quantitative real-time PCR (qRT-PCR) and/or whole-genome microarray, or cryopreserved for therapeutic use. The use of HyStem beads as a means of differentiation facilitates the accumulation of large numbers of beads with large numbers of diverse hEP cell types that can be simultaneously thawed and assayed such as in high throughput robotic systems wherein the beads are exposed to diverse differentiation conditions and their differentiation assayed by gene expression microarray or other means known in the art. It also makes possible the thawing of large numbers of cryopreserved beads and the incubation of combinations of beads with diverse types of embedded cells and subsequent analysis of changes of differentiated state such as gene expression microarray or other means known in the art.

Confluence Adipocyte Cell Differentiation Condition:

Cells were cultured in normal propagation media until reaching confluence, then shifted to different medium for 14 days with DMEM low glucose medium, 10% FBS, Penicillan/Streptomycin, GLX, ITS, Dexamethasone 1 uM, IBMX 0.5 mM, Indomethacin 60 uM. The ITS concentrations used was 6.25 ug/ml insulin, 6.25 ug/ml transferrin, 6.25 ng/ml selenious acid, serum albumin 1.25 mg/ml, 5.35 ug/ml linoleum acid. At the designated periods of time, RNA was extracted using Qiagen RNeasy kits (Qiagen, Valencia, CA, USA cat. #74104) according to the manufacturer's instructions. The RNA yield was maximized using Qiagen's QiaShredder (Qiagen, Valencia, CA, USA cat. #79654) to homogenize samples following the lysis of the micromasses with RLT buffer prior to RNA extraction.

Gene Expression Analysis

Total RNA was extracted directly from cells growing in 6-well plates or 10 cm tissue culture dishes using Qiagen RNeasy mini kits according to the manufacturer's instructions. RNA concentrations were measured using a Beckman DU530 or Nanodrop spectrophotometer and RNA quality was determined by denaturing agarose gel electrophoresis or using an Agilent 2100 bioanalyzer. Whole-genome expression analysis was carried out using Illumina Human Ref-8v3 or Human HT-12 v4 BeadArrays, and RNA levels for certain genes were confirmed by qRTPCR. For the Illumina BeadArrays, total RNA was linearly amplified and biotin-labeled using Illumina TotalPrep kits (Ufe Technologies, Temecula, CA, USA), and cRNA was quality controlled using an Agilent 2100 Bioanalyzer. The cRNA was hybridized to Illumina BeadChips, processed, and read using a BeadStation array reader according to the manufacturer's instructions (Illumina, San Diego, CA, USA). Values of less than 120 relative fluorescence units (RFUs) were considered as nonspecific background signal.

Comparative mRNA Expression in Undifferentiated hEP Cell Lines

A previously reported screen of 100 diverse hES-derived clonal hEP cell lines for collagen type II, alpha I (COL2A1) mRNA expression identified seven responsive lines: 4D20.8, 7PEND24, 7SMOO32, E15, MEL2, SK11, and SM30 with site-specific gene expression (Sternberg et al, *Regen Med.* 2013 March; 8(2):125-44. Seven diverse human embryonic stem cell derived chondrogenic clonal embryonic progenitor cell lines display site-specific cell fates. To screen for site-specific hEP cell lines capable of adipocyte differentiation, and in particular, to identify hEP cell lines capable of brown fat cell differentiation, diverse hEP cell lines were differentiated in conditions that may induce said BAT cell differentiation such as the culture of said progenitors in the presence of HyStem beads supplemented with BMP4 as described herein and screening for the expression of the adipokine C19ORF80, or conditions such as Adipocyte Differentiation Protocol 1 expected to induce UCP1 expression in cells capable of BAT cell differentiation and mRNA was analyzed by microarray analysis using Illumina Human HT-12 v4 bead array analysis. RFU values were rank invariant normalized and the resulting values compared as described herein. RFU values of 120 RFU or less were considered background RFU values associated with non-specific hybridization for the data presented in the present invention.

Kits and Media

In certain embodiments the invention provides a kit for differentiating progenitor cell, such as hEP cells described infra. In one embodiment the kit comprises a media supplemented with one or more exogenously added TGF-β superfamily member. The TGF-β superfamily member may include one or more of the following: TGF-beta proteins including TGF-β3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Mülllerian Inhibiting Substance (MIS), Inhibins, and Nodal.

In some embodiments the media is supplemented with a plurality of exogenously added TGF-β superfamily members. In one embodiment the media is supplemented with BMP4 and BMP7. In another embodiment, the progenitor cell line is cultured in combinations of conditions wherein the cells are cultured in a hydrogel at temperatures substantially below normal body temperature, as described infra, with or without a differentiation agent such as a member of the TGF-β superfamily, retinoic acid, agonist of PPARγ, adrenergic agonist, and thyroid hormone. One or more of the TGF-β superfamily members described in the preceding paragraph may be provided in the media at a concentration of about 1 ng/ml, 5 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1,000 ng/ml. In some embodiments of the invention the TGF-β superfamily members described in the preceding paragraph may be provided in the media at a concentration of greater than 1,000 ng/ml. The TGF-β superfamily members may be chosen from TGF-beta proteins including TGF-β3, Bone Morphogenetic Proteins (BMPs) including BMP2, 4, 6, and 7, Growth Differentiation Factors (GDFs) including GDF5, Glial-derived Neurotrophic Factors (GDNFs), Activins, Lefty, Mülllerian Inhibiting Substance (MIS), Inhibins, and Nodal.

In some embodiments the kit may comprise a media supplemented with an exogenously added retinol, such as retinoic acid. The exogenously added retinoic acid may be provided at a concentration of about 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 µM. In some embodiments the concentration of the exogenously added retinoic acid is greater than 5.0 µM.

In some embodiments the kit may further comprise a hydrogel. The hydrogel may be comprised of hyaluronate, gelatin and an acrylate. The hyaluronate may be thiolated. The gelatin may be thiolated. The acrylate may be a PEG acrylate such as PEG diacrylate.

In certain embodiments of the invention the kit may further comprise a cell described infra. Thus, in some embodiments, the kit may further comprise a progenitor cell, such as a hEP cell. The hEP cell may have chondrogenic potential. In other embodiments, the kit may further comprise a differentiated progeny of a progenitor cell, such as an in vitro differentiated progeny of a progenitor cell described infra. The kits of the present invention may further comprise instructions for use.

EXEMPLIFICATION

Figure 2:
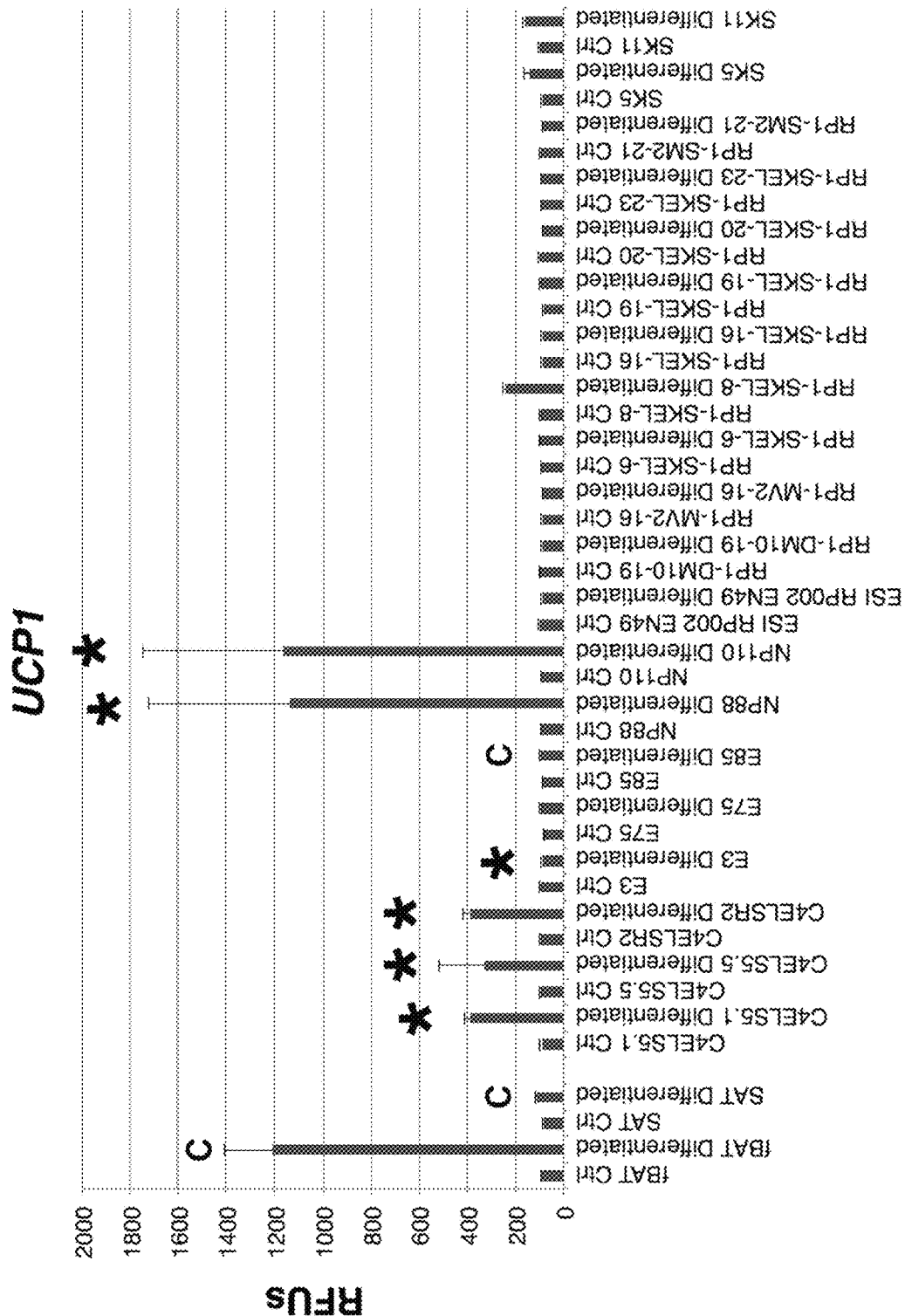
FIG. 2 shows a graph showing Illumina microarray RFU values for the expression of UCP1 in selected cells in the progenitor state (Ctrl) samples and those exposed to differentiation in BMP4, Rosiglitazone, T3, and CL-CL-316243 (Differentiated). (RFU values>130RFU being considered positive) ("*" Identifies CITED1 positive definitive adipocytes).
Figure 3:
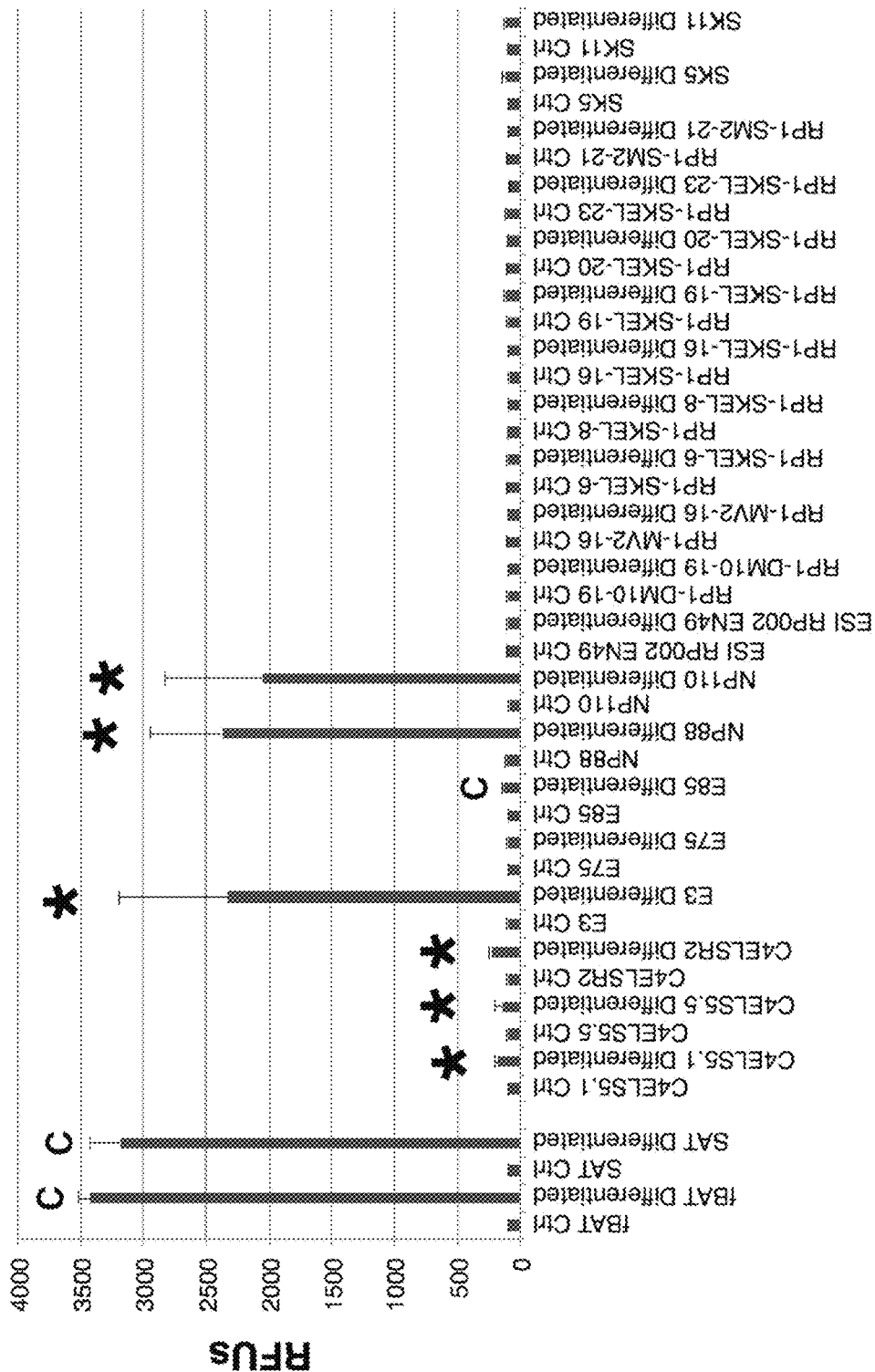
FIG. 3 shows a graph showing Illumina microarray RFU values for the expression of ADIPOQ in selected cells in the progenitor state (Ctrl) samples and those exposed to differentiation in BMP4, Rosiglitazone, T3, and CL-CL-316243 (Differentiated). (RFU values>130RFU being considered positive) ("*" Identifies CITED1 positive definitive adipocytes).
Figure 4:
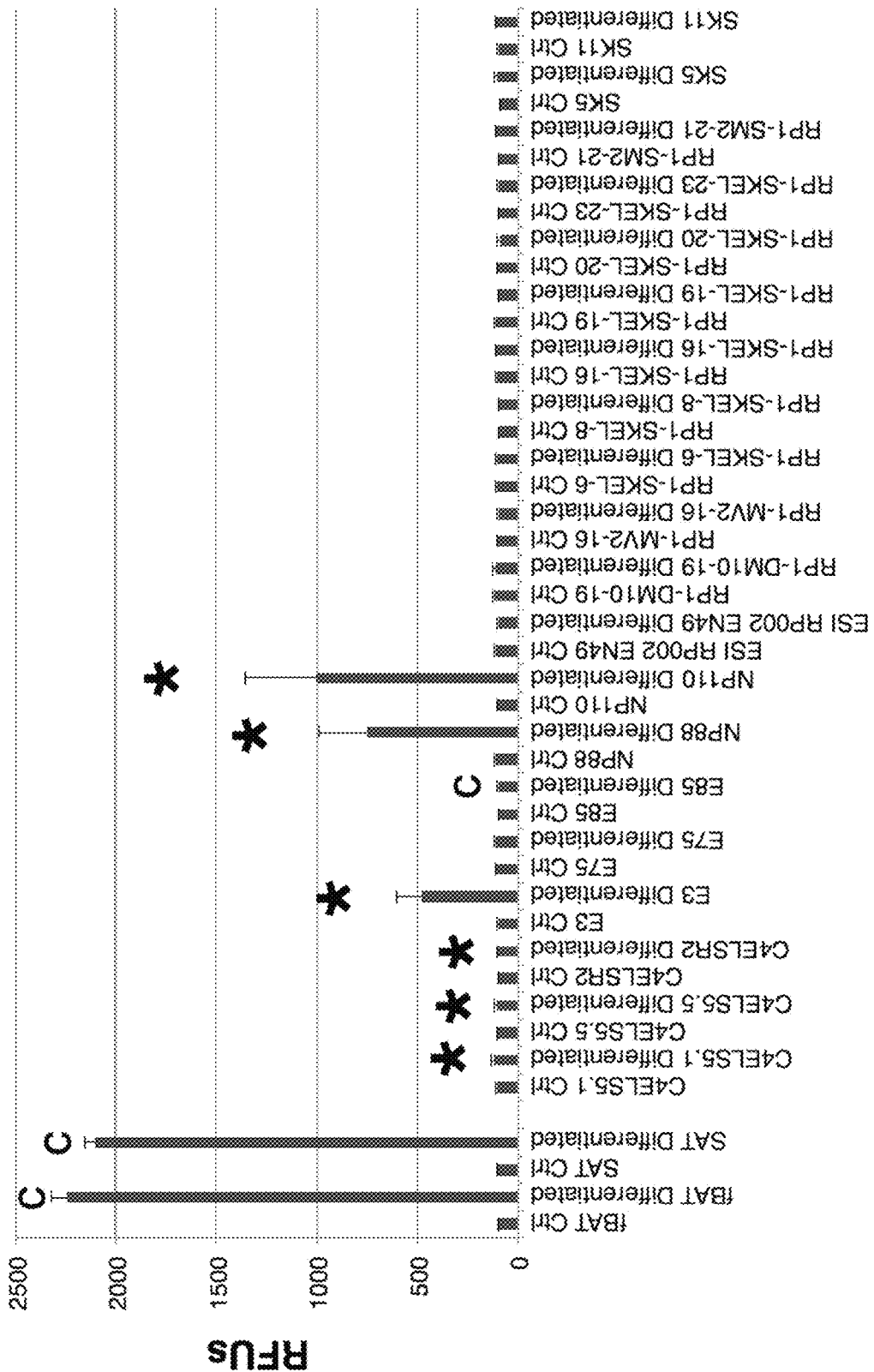
FIG. 4 shows a graph showing Illumina microarray RFU values for the expression of LIPASIN in selected cells in the progenitor state (Ctrl) samples and those exposed to differentiation in BMP4, Rosiglitazone, T3, and CL-CL-316243 (Differentiated). (RFU values>130RFU being considered positive) ("*" Identifies CITED1 positive definitive adipocytes).
Figure 5:
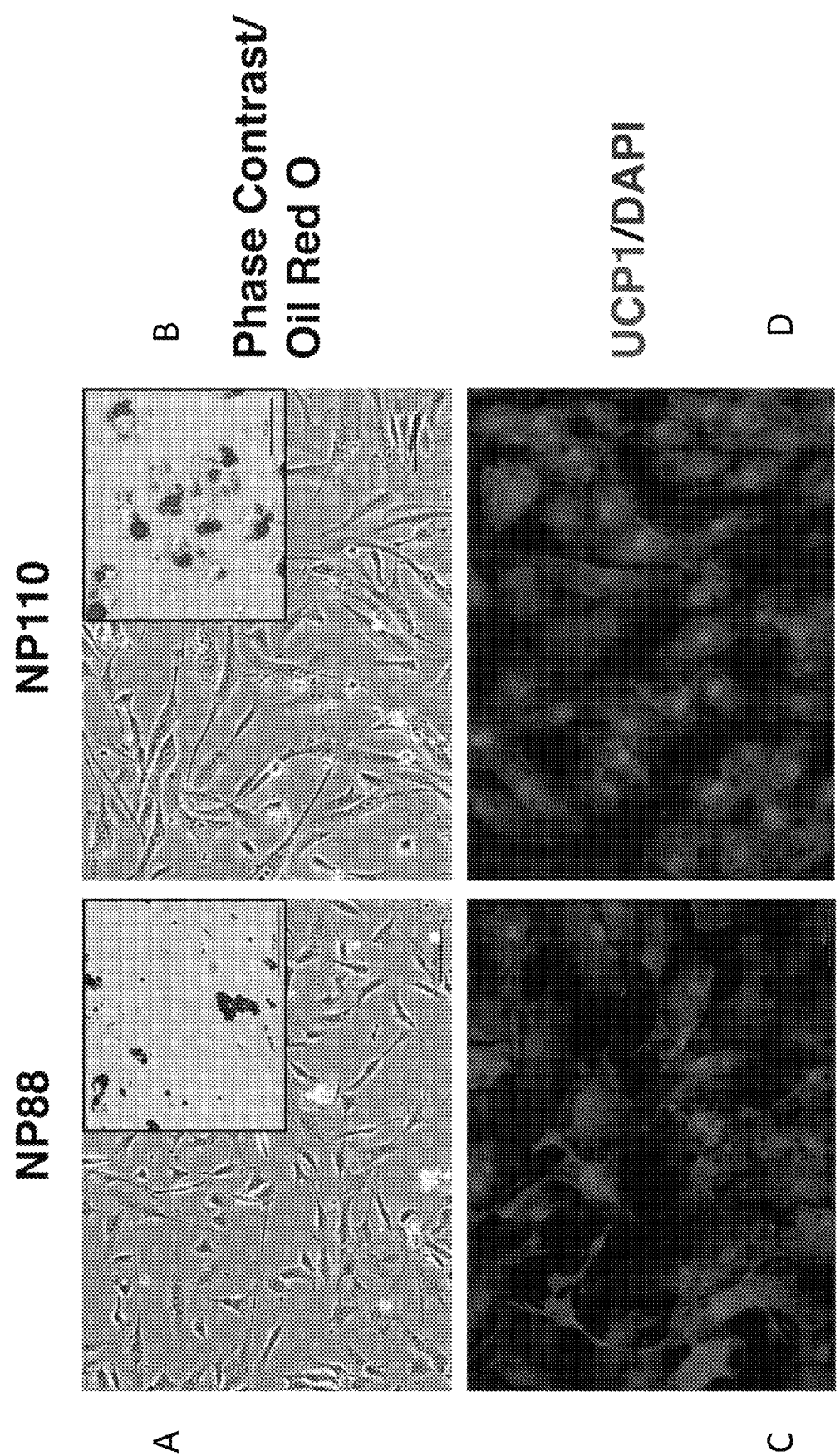
FIG. 5 shows phase contrast photographs of the clonal progenitor cell lines NP88 (A) and NP110 (B) with an inset showing Oil Red-O staining of intracellular lipid as well as immunocytochemical staining of UCP1 protein with DAPI counterstain (C & D).
Figure 6:
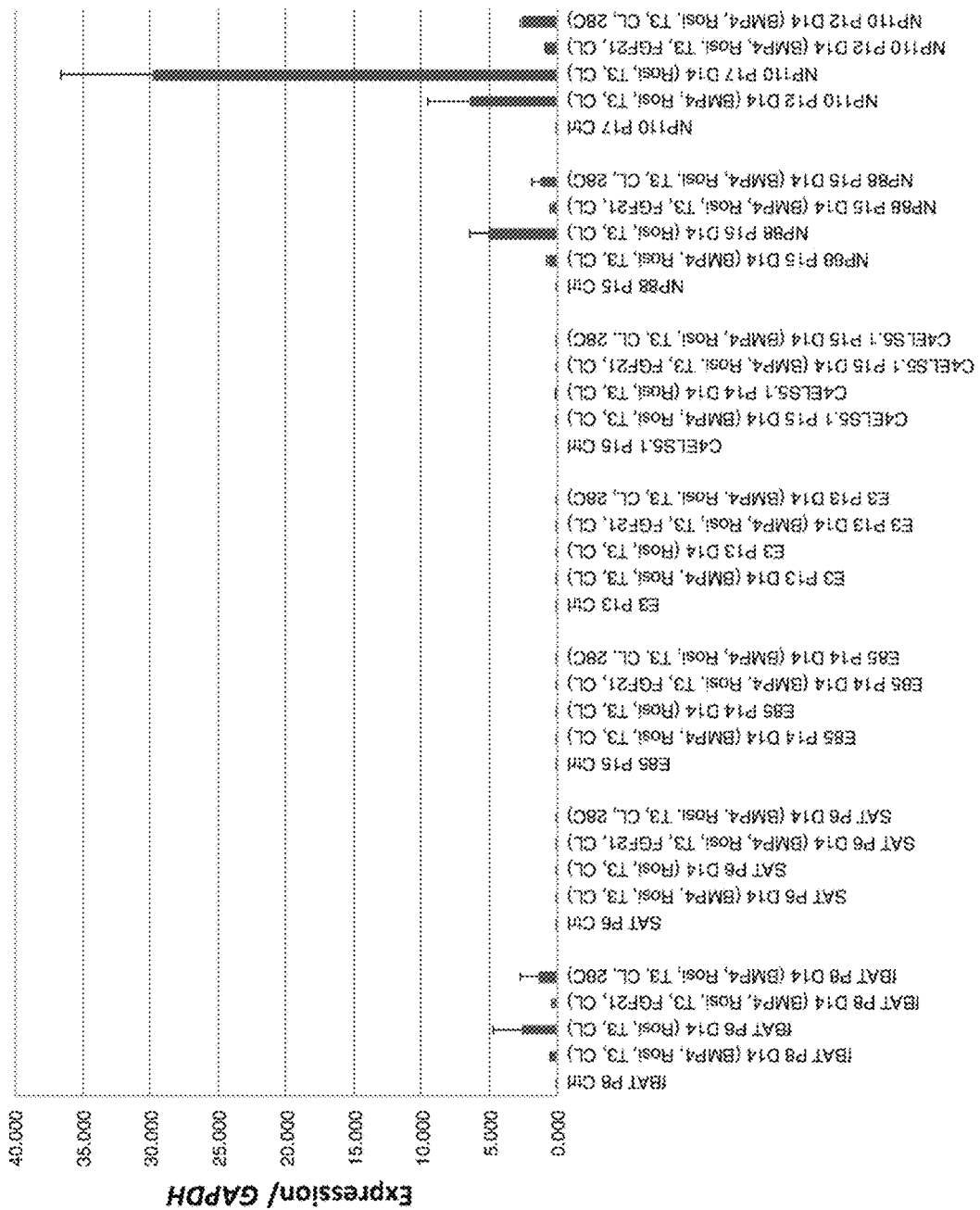
FIG. 6 shows a graph showing qPCR quantitation of UCP1 expression in fBAT and SAT control cells as well as diverse clonal embryonic progenitor cells in differing differentiation conditions to identify optimum conditions for inducing UCP1 expression.

EXAMPLE 1: Analysis of Effects of Adipocyte Differentiation Conditions Diverse Clonal Embryonic Progenitor Cell Lines As shown in FIG. 1, many diverse clonal embryonic progenitor cell lines (CtrI) expressed increased levels of the adipocyte marker FABP4 when cultured in HyStem beads supplemented with 10 ng/ml BMP4, 1.0 µM rosiglitazone, 2.0 nM triiodothyronine (T3), and for the last 4 hours prior to use, 10 µM CL316243 (Differentiated). As shown in FIGS. 2-4, only a subset of these diverse clonal hEP cell lines exhibited an up-regulation of UCP1, BETATROPHIN (also known as C19ORF80, LOC55908, and C19Orf80) or ADIPOQ. While cultured fetal brown fat tissue (fBAT)-derived preadipocytes and subcutaneous adipose tissue (SAT)-derived preadipocytes showed only a minority of cells staining with the adipocyte marker Oil Red-O as described herein, and a minority of cells staining for UCP1, essentially all cells stained for the markers in differentiated cultures of the NP88 and NP110 lines (FIG. 5). As shown in FIG. 6, optimum UCP1 expression was observed in HyStem beads in the condition where the cells were differentiated in the presence of 1.0 µM rosiglitazone, 2.0 nM triiodothyronine (T3), and for the last 4 hours prior to use, 10 µM CL316243. In addition, ELISA analysis confirmed a robust up-regulation of adiponectin and lipasin production in the above-described lines.

Example 2. BAT Cells Manufactured from Universal Donor cGMP Human ES Cell Lines Clinical grade cGMP-compatible human ES cell lines are genetically modified to constitutively express CTLA4-Ig and PD-L1 (Z. Rong, et al, An Effective Approach to Prevent Immune Rejection of Human ESC-Derived Allografts, *Cell Stem Cell*, 14: 121-130 (2014) incorporated herein by reference. In brief, the human ES cell lines described by J. Crook et al, The Generation of Six Clinical-Grade Human Embryonic Stem Cell Lines, *Cell Stem Cell* 1, November 2007, are genetically-modified to constitutively express the genes CTLA4-Ig and PDLI using a BAC-based targeting vector such as the HPRT BAC clone RP11-671P4 (Invitrogen) and the targeting vector is constructed using recombineering as described (Rong et al, A scalable approach to prevent teratoma formation of human embryonic stem cells, *J. Biol. Chem.* 287: 32338-32345; Song et al, Modeling disease in human ESCs using an efficient BAC-based homologous recombination system, *Cell Stem Cell* 6: 80-89.) incorporated herein by reference. The pCAG/CTLA4-Ig/IRES/PD-L1/poly A expression cassette is placed 600 bp downstream of the HPRT1 stop codon and the Loxp-flanked selection cassette pCAG/Neo/IRES/Puro/polyA was placed between the HPRT1 stop codon and its polyA site and Cre-mediated deletion of the selection cassette then yielded the normal expression of HPRT.

The genetic modifications are performed in cGMP conditions and the genome of the hES cells is sequenced to document the insertion site of the exogenous genes and to document the normality of the cells as described (Funk, W. D., Evaluating the genomic and sequence integrity of human ES cell lines; comparison to normal genomes *Stem Cell Research* (2012) 8, 154-164). Master cell banks and working cell banks are established and the working cell banks are differentiated into the BAT cellular components described herein, including betatrophin and adiponectin-expressing adipocytes as well as UCP1-expressing adipocytes, and vascular endothelial cells in combination as described herein.

Example 3. Characterization of Additional Diverse Embryonic BAT Cell Progenitors Derived from hESCs A number of specific human ES cell-derived clonal embryonic progenitor cell lines are disclosed for the first time herein. Specifically, these cell lines have been given the following designations: NP88, NPCC SM19, NPCC SM23, NPCC SM28, NPCC SM31, NPCC SM36, NP111 SM, NP77 EN, NP78 EN, NP80 EN, NP91 SM, NP92 SM, NP93 SM, NP85 EN, NP113 SM, NPCC SM27, and SK1 All clonal embryonic progenitor cell lines were derived from the pluripotent cell stem cell line Envy (Costa et al., The hESC line Envy expresses high levels of GFP in all differentiated progeny, *NAT Methods* 2(4): 259-260 (2005)) with the exception of line SK1 which was derived from hESC cell line H9 (WA09) using methods described under the heading "Novel Uses of Cells With Prenatal Patterns of Gene Expression"; U.S. patent application Ser. No. 11/604,047 filed on Nov. 21, 2006 and entitled "Methods to Accelerate the Isolation of Novel Cell Strains from Pluripotent Stem Cells and Cells Obtained Thereby"; and U.S. patent application Ser. No. 12/504,630 filed on Jul. 16, 2009 and entitled "Methods to Accelerate the Isolation of Novel Cell Strains from Pluripotent Stem Cells and Cells Obtained Thereby"); U.S. patent application Ser. No. 14/048,910 entitled "Differentiated Progeny of Clonal Progenitor Cell Lines," incorporated herein by reference. Clonal, oligoclonal, and pooled populations of clonal and oligoclonal embryonic progenitors were screened for adipogenic and BAT cell differentiation potential as described in (U.S. patent application Ser. No. 13/683,241, entitled "Methods of Screening Embryonic Progenitor Cell Lines", more specifically, U.S. patent application Ser. No. 14/554,019, entitled "Methods for Generating Pluripotent Stem Cell-Derived Brown Fat Cells."

Briefly, the hES cell line hES3 (Envy) was incubated with 1 mg/ml Collagenase for 60 minutes after which the dish was gently tapped to release the hES cell colonies into suspension. These colonies were collected and triturated to generate small clumps which were plated into ultra-low attachment plates (CoStar, Corning, Cat #3471) for embryoid body (EB) formation. The EBs were formed in neural differentiation medium consisting of DMEM/F12 with Glutamax I (Invitrogen, Cat #10565-018) and 1× B27 supplement without Vitamin A (Invitrogen, Cat #12587-010) (referred to as "NP(−)" medium henceforth) and supplemented with 500 ng/ml recombinant human Noggin (R & D systems, Cat #3344-NG-050) and 20 ng/ml bFGF (Strathmann, 130-093-842). Over the next 21 days, spent medium was removed every 48 hours and fresh medium supplemented with 500 ng/ml Noggin and 20 ng/ml bFGF was added to the EBs. On day 21, spent medium was removed and fresh medium supplemented with 20 ng/ml bFGF only was added to the EBs. Reagents were sourced from Invitrogen unless otherwise stated. Neural EB formation was apparent in the culture.

Generation of Stock Candidate Cultures

To generate candidate cultures for clonal isolation, the above-mentioned EBs on day 22 (after one day FGF2-only culture) were dissociated with Accutase (Innovative Cell Technologies, AT-104) for 10 minutes at 37° C. followed by trituration to generate a single cell suspension. The cell suspension in PBS was divided into four tubes and each aliquot was diluted with NP(−) medium (as described above)+20 ng/ml bFGF (designated NP(+) medium herein). Cells were centrifuged at 180 g for 5 minutes and each pellet was seeded into one well of a 6-well tissue culture plate in the NP(+) medium. The medium was changed 24 hours after initial plating and then 3 times a week thereafter. Upon confluence, cells in the 6-well plate were dissociated using TrypLE (Invitrogen, Cat #12563-029) for 5 minutes at 37° C. and replated in progressively larger tissue culture vessels being: T25 flask, T75 flask and T225 flask in the NP(+) medium over a period of several weeks to reach a T225 expansion stage of confluent cells. Candidate cultures of confluent cells in the T225 flask were then dissociated using TrypLE, counted and an aliquot of this single cell suspension was diluted to a concentration of 10,000 cells/ml in the NP(+) media that was used for culture to the T225 stage candidate culture stage. An aliquot of the single cell suspension was then plated at clonal dilution (500-7000 cells per 50 ml that went into the 15 cm dish) in 0.1% Gelatin-coated (Sigma, Cat #G1393) 15 cm dishes in the NP(+) medium. Remaining cells from the candidate cultures were cryopreserved (typically $3 \times 10^6$ to $5 \times 10^6$ cells/vial) using a controlled rate freezer program and freezing media for cryostorage and future use.

Generation of Clonal Embryonic Progenitor Cell Lines From Candidate Cultures

Cloning dishes were prepared by adding 50 ml of the above-mentioned NP(+) medium into Gelatin-coated (0.1%) 15 cm culture dishes. To each dish, a preparation of a single cell suspension from the candidate culture propagated in the NP(+) medium was then manually diluted by adding to the 15 cm culture dishes that volume of cells determined by counting a suspension of cells such that there were a selection of the following dilutions of cells; 500 cells/dish or, 1000 cells/dish or; 1500 cells/dish or; 3000 cells/dish, 5000 cells/dish or 7000 cells/dish to achieve different densities of the single cell suspension and to aid in the isolation of single colonies grown from a single cell. Seeded single cells of an appropriate dilution were distributed evenly in the dish by the sliding the 15 cm dish alternately in a clockwise, followed by counterclockwise, then side to side (left to right) motion, followed by a forward and back motion repeatedly, for about 30 seconds inside the incubator. Dishes were then incubated in a CO2 incubator (5% $CO_2$, 20% $O_2$) and left undisturbed without moving or feeding for 14 days to allow single cells to attach to the culture dish surface and for colonies to grow to sufficient size for isolation.

Dishes were visually inspected and well-separated cell colonies were picked with sterile cloning cylinders (Sigma, Cat #CLS31666, CLS31668 & CLS316610) using 25 ul TrypLE for a 6 mm cylinder, 50 ul TrypLE for an 8 mm cylinder and 100 ul TrypLE for a 10 mm cylinder. Each isolated cell colony was then plated into one well each of 0.1% Gelatin-coated 24 well plates (Nunc, 142475) containing 1 ml of Promocell Smooth Muscle Cell Growth Medium 2 or its equivalent medium (designated SM medium herein). In this instance of the method, isolated embryonic progenitor cells are further cultured in the SM media. Upon confluence, cells in the 24-well plate were dissociated using TrypLE for 5 minutes at 37° C. and re-plated in progressively larger tissue culture vessels being: one well of a 6-well plate, T25 flask, T75 flask and T225 flask(s) in the SM medium over several weeks (an average of 1-2 weeks between each passage). Confluent cells in the T225 flask(s) were cryopreserved and banked as an isolated Embryonic Progenitor Cell Lines and seeded for immunostaining and RNA isolation, such as for PCR amplification of transcripts described herein. The cell line NP88 was derived and characterized herein.

Re-Derivation of Clonal Embryonic Progenitors of Brown Fat Cells from Cryopreserved Candidate Cultures A cryopreserved candidate culture produced under the conditions described in this example was thawed and additional clonal embryonic progenitor cell lines were isolated as described in this example above. A subset of these lines was designated NPCC SM19, NPCC SM23, NPCC SM28, NPCC SM31 and NPCC SM40.

When RNA was extracted from these clonal embryonic progenitor cell lines at passage 10 and introduced into quiescence for 5 days, a condition sometimes referred to as "control" or "Ctrl" herein, the cells displayed the gene expression marker profile described in Table 1 below. For purposes of Example 3, microarray determined transcript expression above background, defined in Example 3 as values greater than 130 RFUs, is characterized as "expressed." Array analysis yielding transcript expression data of 120 RFUs or less is characterized as unexpressed in Example 3.

Figure 7:
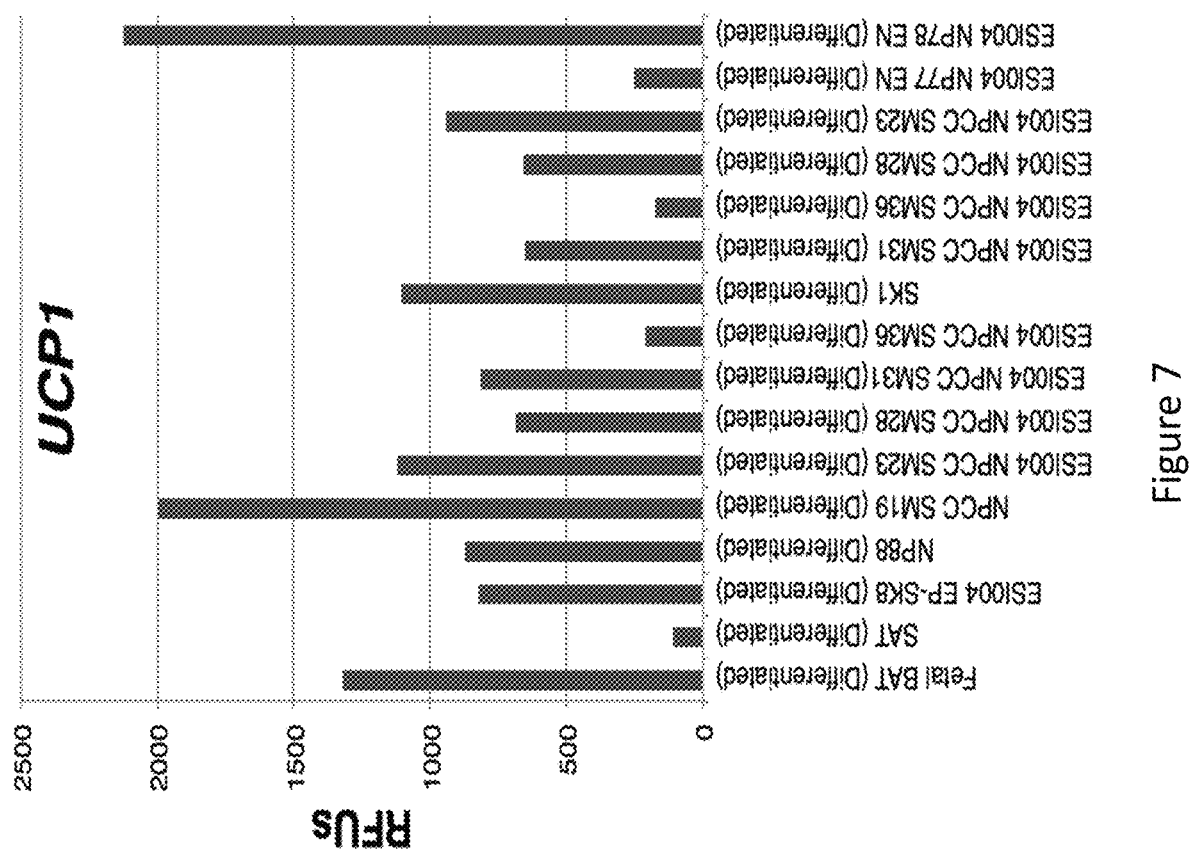
FIG. 7 shows a graph showing Illumina microarray RFU values for the expression of UCP1 in additional selected cells differentiated in BMP4, Rosiglitazone, T3, and CL-CL-316243 (Differentiated). (RFU values>130RFU being considered positive).
Figure 8:
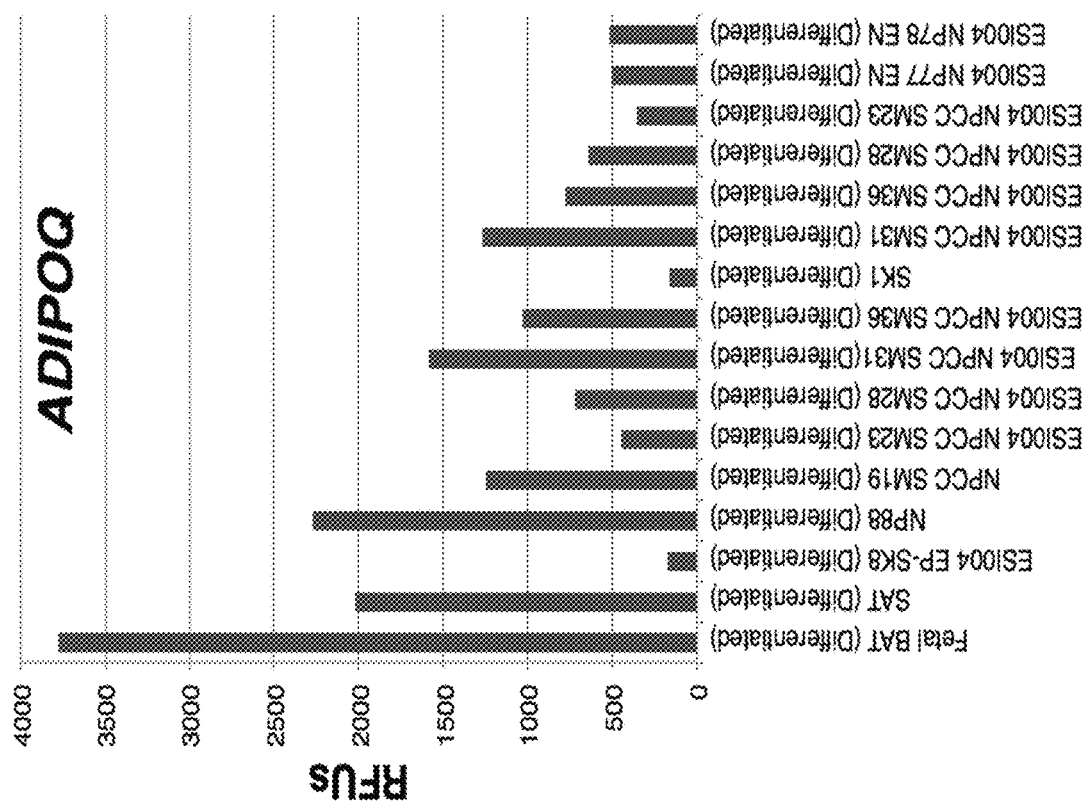
FIG. 8 shows a graph showing Illumina microarray RFU values for the expression of ADIPOQ in additional selected cells differentiated in BMP4, Rosiglitazone, T3, and CL-CL-316243 (Differentiated). (RFU values>130RFU being considered positive).
Figure 9:
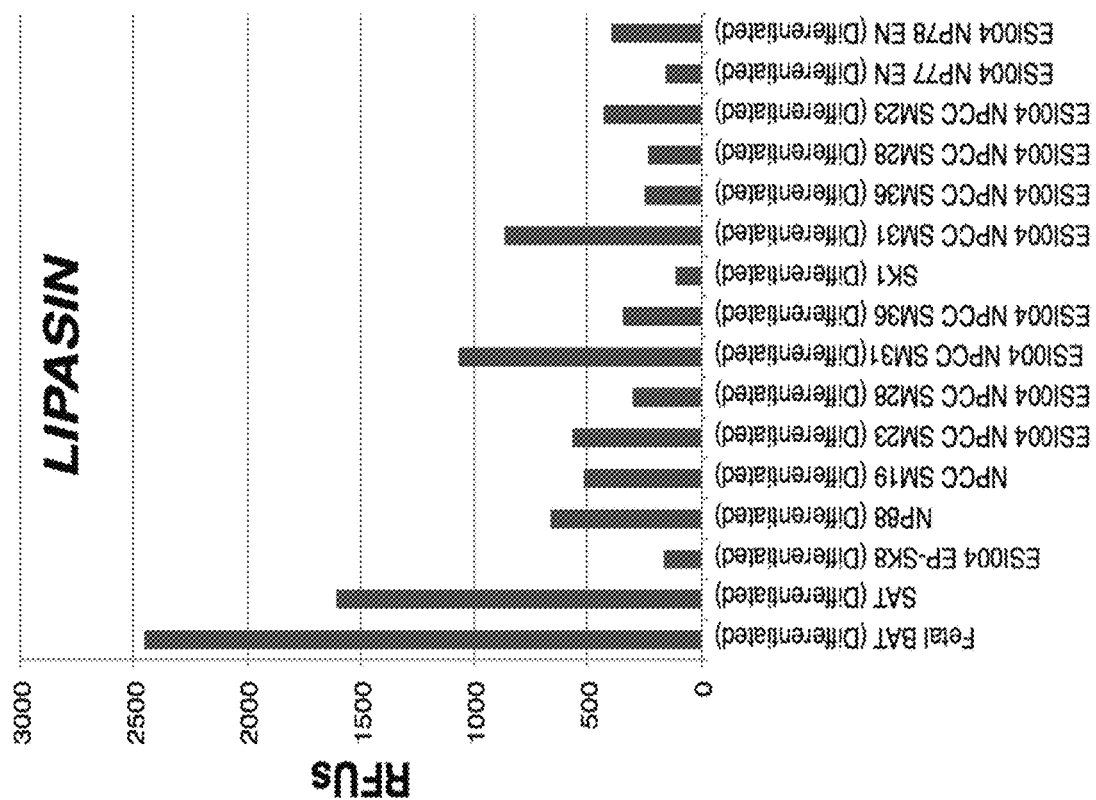
FIG. 9 shows a graph showing Illumina microarray RFU values for the expression of LIPASIN in additional selected cells differentiated in BMP4, Rosiglitazone, T3, and CL-CL-316243 (Differentiated). (RFU values>130RFU being considered positive).

As shown in FIG. 7, each of these lines expressed UCP1 when differentiated 14 days in Hystem beads supplemented with 10 ng/ml BMP4, 1.0 µM rosiglitazone, 2.0 nM triiodothyronine (T3), and for the last 4 hours prior to use, 10 µM CL316243 (Differentiated). As shown in FIG. 8, the lines also expressed ADIPOQ and as shown in FIG. 9, each line additionally expressed LIPASIN.

TABLE 1, below, shows gene expression levels in RFU values of select markers quantitated on Illumina bead arrays for the diverse clonal embryonic progenitor cell lines of the present invention in the undifferentiated progenitor state. (RFU values>130RFU being considered positive while RFU values<120RFU being considered negative).

TABLE 1

| ProbeID | Accession | Symbol | ES1004-EP SKB P11 ctrl | ES1004 NP111 5M P12 ctrl | ES1004 NP77 EN P8 ctrl | PS1004 NP80 EN P8 ctrl | ES1004 NP95 EN P8 ctrl | NP85 (P12) Ctrl | NPCC SM19(P5) Ctrl | NPCC 5M28 PS ctrl | ES1004 NPCC SM36 P5 ctrl |
|---|---|---|---|---|---|---|---|---|---|---|---|
| 5390138 | NM_001864.2 | COX7A1 | 93 | 87 | 88 | 94 | 89 | 90 | 92 | 88 | 91 |
| 60136 | NM_031311.3 | CPVL | 83 | 88 | 92 | 100 | 98 | 89 | 90 | 94 | 96 |
| 610437 | NM_013230.2 | CD24 | 135 | 87 | 96 | 98 | 90 | 130 | 104 | 317 | 449 |
| 2760739 | NM_005807.3 | PRG4 | 301 | 481 | 448 | 470 | 495 | 103 | 99 | 91 | 101 |
| 2510132 | NM_004378.1 | CRABP1 | 133 | 1119 | 4010 | 632 | 5648 | 97 | 99 | 119 | 96 |
| 5310364 | NM_173462.3 | PAPLN | 119 | 298 | 735 | 541 | 946 | 167 | 95 | 94 | 92 |
| 3440253 | NM_130811.1 | SNAP25 | 187 | 322 | 1082 | 619 | 795 | 109 | 103 | 143 | 102 |
| 1940747 | NM_181505.1 | PPP1R18 | 226 | 401 | 2186 | 198 | 687 | 267 | 95 | 96 | 95 |
| 6180348 | NM_001362.2 | DIO3 | 107 | 837 | 1188 | 117 | 148 | 654 | 118 | 96 | 112 |
| 6510259 | NM_003836.4 | DLK1 | 97 | 5160 | 271 | 724 | 4783 | 6713 | 1374 | 201 | 121 |
| 3370767 | NM_005221.5 | DLX5 | 99 | 94 | 94 | 95 | 95 | 90 | 91 | 761 | 92 |
| 6400044 | NM_017549.3 | EPOR1 | 118 | 101 | 100 | 101 | 97 | 654 | 92 | 95 | 105 |
| 6330270 | NM_001448.2 | GPC4 | 89 | 91 | 120 | 309 | 114 | 1212 | 94 | 92 | 97 |
| 4260692 | NM_006735.3 | HOXA2 | 103 | 100 | 97 | 92 | 99 | 105 | 446 | 537 | 361 |
| 6620437 | NM_019102.2 | HOXA5 | 96 | 100 | 89 | 94 | 92 | 92 | 629 | 100 | 99 |
| 6480204 | NM_006288.2 | THY1 | 1756 | 114 | 487 | 1559 | 530 | 613 | 578 | 271 | 2557 |
| 3460097 | NM_002145.3 | HOX82 | 110 | 95 | 94 | 92 | 96 | 99 | 283 | 210 | 99 |
| 5420386 | NM_000640.2 | IL13RA2 | 100 | 93 | 91 | 96 | 98 | 101 | 95 | 112 | 100 |
| 1660767 | NM_005382.1 | NEFM | 109 | 100 | 92 | 121 | 123 | 105 | 3565 | 97 | 98 |
| 6940053 | NM_014917.2 | NTNG1 | 93 | 95 | 85 | 94 | 87 | 116 | 89 | 94 | 92 |
| 6650731 | NM_002899.2 | RBP1 | 103 | 97 | 91 | 101 | 94 | 100 | 1334 | 105 | 683 |
| 4480477 | NM_198538.1 | SBSN | 187 | 266 | 351 | 244 | 166 | 801 | 102 | 194 | 99 |
| 4210403 | NM_004172.3 | SLC1A3 | 99 | 309 | 585 | 160 | 254 | 343 | 137 | 148 | 120 |
| 5090289 | NM_004093.2 | EFN82 | 118 | 98 | 110 | 157 | 121 | 140 | 109 | 139 | 251 |
| 510368 | NM_007129.2 | ZIC2 | 305 | 4211 | 4108 | 427 | 3737 | 511 | 102 | 1386 | 373 |

| ProbeID | Accession | Symbol | ES1004 NPCC SM31 PS crtl | ES1004 NPCC SM23 PS crtl | ES1004 NPCC SM27 P5 crtl | ES8004 NP78 EN P7 ctrl | SK1 P15 ctrl | ES1004 NP92 SM P8 ctrl | ES1004 NP91 SM P8 ctrl | ES1004 NP95 SM P9 ctrl | ES1004 NP113 SM P10 ctrl |
|---|---|---|---|---|---|---|---|---|---|---|---|
| 5390138 | NM_001864.2 | COX7A1 | 97 | 93 | 88 | 95 | 99 | 100 | 87 | 89 | 86 |
| 60136 | NM_031311.3 | CPVL | 96 | 89 | 91 | 88 | 97 | 93 | 95 | 114 | 907 |
| 610437 | NM_013230.2 | CD24 | 287 | 109 | 847 | 102 | 286 | 111 | 127 | 154 | 103 |
| 2760739 | NM_005807.3 | PRG4 | 916 | 104 | 100 | 126 | 130 | 102 | 124 | 428 | 169 |
| 2510132 | NM_004378.1 | CRABP1 | 106 | 104 | 97 | 101 | 103 | 89 | 92 | 86 | 99 |
| 5310364 | NM_173462.3 | PAPLN | 169 | 98 | 97 | 651 | 733 | 91 | 86 | 230 | 157 |
| 3440253 | NM_130811.1 | SNAP25 | 321 | 100 | 106 | 533 | 190 | 85 | 103 | 518 | 105 |
| 1940747 | NM_181505.1 | PPP1R1B | 120 | 99 | 98 | 298 | 184 | 99 | 105 | 118 | 101 |
| 6180348 | NM_001362.2 | DIO3 | 119 | 110 | 102 | 128 | 106 | 109 | 258 | 108 | 102 |
| 6510259 | NM_003836.4 | DLK1 | 6931 | 96 | 98 | 2440 | 145 | 1180 | 7246 | 670 | 209 |
| 3370767 | NM_005221.5 | DLXS | 1598 | 101 | 88 | 88 | 101 | 465 | 93 | 171 | 95 |
| 6400044 | NM_017549.3 | EPOR1 | 93 | 102 | 99 | 224 | 105 | 98 | 971 | 104 | 131 |
| 6330270 | NM_001448.2 | GPC4 | 98 | 87 | 97 | 434 | 99 | 1498 | 1289 | 1491 | 174 |
| 4260692 | NM_006735.3 | HOXA2 | 563 | 306 | 656 | 159 | 100 | 99 | 92 | 98 | 95 |
| 6620437 | NM_019102.2 | HOXA5 | 94 | 109 | 104 | 636 | 95 | 94 | 98 | 96 | 94 |
| 6480204 | NM_006288.2 | THY1 | 91 | 1139 | 108 | 1271 | 651 | 1545 | 152 | 579 | 2975 |
| 3460097 | NM_002145.3 | HOX82 | 100 | 113 | 105 | 104 | 129 | 98 | 93 | 93 | 94 |
| 5420386 | NM_000640.2 | IL13RA2 | 94 | 91 | 89 | 120 | 114 | 141 | 93 | 91 | 140 |
| 1660767 | NM_005382.1 | NEFM | 100 | 101 | 96 | 99 | 93 | 109 | 108 | 105 | 129 |
| 6940053 | NM_014917.2 | NTNG1 | 92 | 116 | 88 | 132 | 122 | 221 | 109 | 93 | 156 |
| 6650731 | NM_002899.2 | RBP1 | 122 | 169 | 462 | 97 | 1334 | 99 | 100 | 111 | 94 |
| 4480477 | NM_19853 8.1 | S8SN | 102 | 103 | 126 | 237 | 102 | 252 | 199 | 571 | 503 |
| 4210403 | NM_004172.3 | SLC1A3 | 138 | 114 | 98 | 181 | 158 | 242 | 411 | 123 | 224 |
| 5090289 | NM_004093.2 | EFN82 | 157 | 316 | 179 | 135 | 280 | 101 | 223 | 92 | 117 |
| 510368 | NM_007129.2 | ZIC2 | 719 | 394 | 1084 | 454 | 101 | 105 | 96 | 182 | 1467 |

We claim:

1. A method of producing brown adipocytes comprising:
   a. differentiating a human pluripotent stem cell in a neural differentiation medium consisting of DMEM/F12, B27 supplement, and basic Fibroblast Growth Factor (bFGF), thereby forming an embryoid body;
   b. producing a clonal embryonic progenitor cell line from the embryoid body, wherein said clonal embryonic progenitor cell line expresses DIO3, SLC1A3, SBSN, DLK1 and ZIC2, but does not express COX7A1, DLX5, HOXA5, IL13RA2, CRABP1, NEFM, PRG4, and RBP1;
   c. differentiating the clonal embryonic progenitor cell line in the presence of a PPARgamma (PPARγ) agonist, a thyroid hormone, and a TGFβ family member polypeptide, thereby producing a differentiated progeny from the clonal embryonic progenitor cell line;
   d. screening the differentiated progeny from the clonal embryonic progenitor cell line for the expression of a brown adipocyte marker comprising UCP1; and
   e. isolating UCP1 expressing brown adipocytes.

2. The method of claim 1, wherein the PPARgamma agonist is rosiglitazone.

3. The method of claim 1, wherein the UCP1 expressing brown adipocytes are further characterized by the expression of one or more of ADIPOQ, C19orf80, FABP4 or CD36.

4. A method of producing brown adipocytes comprising:
   a. differentiating a human pluripotent stem cell in a neural differentiation medium consisting of DMEM/F12, B27 supplement, and basic Fibroblast Growth Factor (bFGF), thereby forming an embryoid body;
   b. producing a clonal embryonic progenitor cell line from the embryoid body, wherein said clonal embryonic progenitor cell line expresses HOXA2, HOXB2, NEFM, RBP1 and DLK1, but does not express COX7A1, IL13RA2, ZIC2, DLX5, PRG4, CRABP1 and SBSN;
   c. differentiating the clonal embryonic progenitor cell line in the presence of a PPARgamma (PPARγ) agonist, a thyroid hormone, and a TGFβ family member polypeptide, thereby producing a differentiated progeny from the clonal embryonic progenitor cell line;
   d. screening the differentiated progeny from the clonal embryonic progenitor cell line for the expression of a brown adipocyte marker comprising UCP1; and
   e. isolating UCP1 expressing brown adipocytes.

5. The method of claim 4, wherein the PPARgamma agonist is rosiglitazone.

6. The method of claim 4, wherein the UCP1 expressing brown adipocytes are further characterized by the expression of one or more of ADIPOQ, C19orf80, FABP4 or CD36.

7. A method of producing brown adipocytes comprising:
   a. differentiating a human pluripotent stem cell in a neural differentiation medium consisting of DMEM/F12, B27 supplement, and basic Fibroblast Growth Factor (bFGF), thereby forming an embryoid body;
   b. producing a clonal embryonic progenitor cell line from the embryoid body, wherein said clonal embryonic progenitor cell line expresses RBP1, ZIC2 and HOXA2, but does not express COX7A1, HOXB2, HOXA5, NEFM, PRG4, DLX5, IL13RA2, CRABP1, and SBSN;
   c. differentiating the clonal embryonic progenitor cell line in the presence of a PPARgamma (PPARγ) agonist, a thyroid hormone, and a TGFβ family member polypeptide, thereby producing a differentiated progeny from the clonal embryonic progenitor cell line;

d. screening the differentiated progeny from the clonal embryonic progenitor cell line for the expression of a brown adipocyte marker comprising UCP1; and e. isolating UCP1 expressing brown adipocytes.

8. The method of claim 7, wherein the PPARgamma agonist is rosiglitazone.

9. The method of claim 7, wherein the UCP1 expressing brown adipocytes are further characterized by the expression of one or more of ADIPOQ, C19orf80, FABP4 or CD36.

10. The method of claim 1, wherein the TGFβ family member polypeptide is BMP4.

11. The method of claim 4, wherein the TGFβ family member polypeptide is BMP4.

12. The method of claim 7, wherein the TGFβ family member polypeptide is BMP4.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Homo sapiens

```
<400> SEQUENCE: 1
ggcctccaag gagtaagacc                                              20

<210> SEQ ID NO 2
<211> LENGTH: 20
<212> TYPE: DNA
<213> ORGANISM: Homo sapiens

<400> SEQUENCE: 2
aggggtctac atggcaactg                                              20

<210> SEQ ID NO 3
<211> LENGTH: 21
<212> TYPE: DNA
<213> ORGANISM: Homo sapiens

<400> SEQUENCE: 3
aggcgtgaag agcaagggaa a                                            21

<210> SEQ ID NO 4
<211> LENGTH: 22
<212> TYPE: DNA
<213> ORGANISM: Homo sapiens

<400> SEQUENCE: 4
ccccatcttc actcagagac tg                                           22

<210> SEQ ID NO 5
<211> LENGTH: 20
<212> TYPE: DNA
<213> ORGANISM: Homo sapiens

<400> SEQUENCE: 5
gacctggact gaagttcgca                                              20

<210> SEQ ID NO 6
<211> LENGTH: 21
<212> TYPE: DNA
<213> ORGANISM: Homo sapiens

<400> SEQUENCE: 6
acttgcttgc taaatcaggg a                                            21

<210> SEQ ID NO 7
<211> LENGTH: 19
<212> TYPE: DNA
<213> ORGANISM: Homo sapiens

<400> SEQUENCE: 7
ctacgggaca gcgtgcagc                                               19

<210> SEQ ID NO 8
<211> LENGTH: 23
<212> TYPE: DNA
<213> ORGANISM: Homo sapiens

<400> SEQUENCE: 8
cagcatgatt ggtcctcagt tcc                                          23

<210> SEQ ID NO 9
<211> LENGTH: 22
<212> TYPE: DNA
```

```
<213> ORGANISM: Homo sapiens

<400> SEQUENCE: 9
gctgacaaag gccaggaaca gc                                            22

<210> SEQ ID NO 10
<211> LENGTH: 20
<212> TYPE: DNA
<213> ORGANISM: Homo sapiens

<400> SEQUENCE: 10
acctccccca gcacctcagc                                               20

<210> SEQ ID NO 11
<211> LENGTH: 21
<212> TYPE: DNA
<213> ORGANISM: Homo sapiens

<400> SEQUENCE: 11
gcaagcctgt tggagactca g                                             21

<210> SEQ ID NO 12
<211> LENGTH: 19
<212> TYPE: DNA
<213> ORGANISM: Homo sapiens

<400> SEQUENCE: 12
ctgtcccgta gcaccttct                                                19
```